(12) United States Patent
Traynor et al.

(10) Patent No.: US 11,707,421 B2
(45) Date of Patent: *Jul. 25, 2023

(54) COMPOSITIONS CONTAINING A FLEXIBLE DERIVED CAPSULE WITH AN ACTIVE AGENT

(71) Applicant: CoLabs International Corporation, Las Vegas, NV (US)

(72) Inventors: Daniel H. Traynor, Sarasota, FL (US); Laura E. Cohen, Huntington Beach, CA (US)

(73) Assignee: CoLabs Int'l Corp., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/490,812

(22) Filed: Apr. 18, 2017

(65) Prior Publication Data

US 2017/0216164 A1 Aug. 3, 2017

Related U.S. Application Data

(63) Continuation-in-part of application No. 15/430,416, filed on Feb. 10, 2017, now Pat. No. 10,322,301, and a continuation-in-part of application No. PCT/US2017/017556, filed on Feb. 10, 2017, said application No. 15/430,416 is a continuation of application No. 14/702,615, filed on May 1, 2015, (Continued)

(51) Int. Cl.
| | |
|---|---|
| *A61K 8/11* | (2006.01) |
| *A61Q 17/04* | (2006.01) |
| *A61Q 19/10* | (2006.01) |
| *A61Q 17/02* | (2006.01) |
| *A61K 8/92* | (2006.01) |
| *A01N 25/28* | (2006.01) |
| *A61Q 5/02* | (2006.01) |
| *A61K 8/37* | (2006.01) |
| *B01J 13/14* | (2006.01) |
| *A61K 8/35* | (2006.01) |
| *A61K 8/895* | (2006.01) |
| *A61Q 5/12* | (2006.01) |
| *A61K 8/44* | (2006.01) |
| *A61K 8/46* | (2006.01) |
| *A61Q 19/00* | (2006.01) |
| *A61K 8/73* | (2006.01) |
| *A61K 8/31* | (2006.01) |
| *A61K 8/40* | (2006.01) |
| *A61Q 5/06* | (2006.01) |
| *A61K 8/81* | (2006.01) |
| *A01N 25/30* | (2006.01) |
| *A01N 65/28* | (2009.01) |
| *C11D 17/00* | (2006.01) |
| *C11D 3/48* | (2006.01) |
| *A61Q 17/00* | (2006.01) |

(52) U.S. Cl.
CPC ............. *A61K 8/11* (2013.01); *A01N 25/28* (2013.01); *A01N 25/30* (2013.01); *A01N 65/28* (2013.01); *A61K 8/31* (2013.01); *A61K 8/35* (2013.01); *A61K 8/37* (2013.01); *A61K 8/375* (2013.01); *A61K 8/40* (2013.01); *A61K 8/442* (2013.01); *A61K 8/463* (2013.01); *A61K 8/466* (2013.01); *A61K 8/731* (2013.01); *A61K 8/8158* (2013.01); *A61K 8/895* (2013.01); *A61K 8/922* (2013.01); *A61Q 5/02* (2013.01); *A61Q 5/06* (2013.01); *A61Q 5/12* (2013.01); *A61Q 17/02* (2013.01); *A61Q 17/04* (2013.01); *A61Q 19/007* (2013.01); *A61Q 19/10* (2013.01); *B01J 13/14* (2013.01); *C11D 3/48* (2013.01); *C11D 17/0039* (2013.01); *A61K 2800/412* (2013.01); *A61Q 17/005* (2013.01); *Y02A 50/30* (2018.01)

(58) Field of Classification Search
None
See application file for complete search history.

(56) References Cited

U.S. PATENT DOCUMENTS

| 1,478,208 A | 12/1923 | Duddleson et al. |
| 3,462,479 A | 8/1969 | Strobel et al. |

(Continued)

FOREIGN PATENT DOCUMENTS

| CN | 1341012 A | 3/2002 |
| EP | 0025379 B1 | 6/1984 |

(Continued)

OTHER PUBLICATIONS

Specos, MM Miró, et al. "Microencapsulated citronella oil for mosquito repellent finishing of cotton textiles." Transactions of the Royal Society of Tropical Medicine and Hygiene 104.10 (2010): 653-658.*

(Continued)

*Primary Examiner* — David J Blanchard
*Assistant Examiner* — Sarah J Chickos
(74) *Attorney, Agent, or Firm* — UltimatEdge IP Law Group, P.C.; Dean G. Stathakis

(57) ABSTRACT

The present specification discloses compositions comprising one or more encapsulates comprising one or more agents and methods and uses for the disclosed agents. A composition disclosed herein can be incorporated into a body wash, an after shower body lotion, a shampoo, a conditioner, a soap, a gel, a hand sanitizer, a cream, a spray, a mouse, a lotion, an ointment, a make-up product, a lip balm, a hair spray product, an arachnid/insect repellent or a medicinal product.

19 Claims, 3 Drawing Sheets

Related U.S. Application Data now Pat. No. 9,592,184, which is a continuation of application No. 14/072,926, filed on Nov. 6, 2013, now Pat. No. 9,456,966.

(60) Provisional application No. 62/293,703, filed on Feb. 10, 2016, provisional application No. 61/769,758, filed on Feb. 27, 2013, provisional application No. 61/722,870, filed on Nov. 6, 2012.

(56) References Cited

U.S. PATENT DOCUMENTS

| | | | |
|---|---|---|---|
| 3,691,270 | A | 9/1972 | Charle et al. |
| 4,402,977 | A | 9/1983 | Grollier et al. |
| 4,540,507 | A | 9/1985 | Grollier |
| 4,542,125 | A | 9/1985 | Gorman et al. |
| 4,663,155 | A | 5/1987 | Murray et al. |
| 4,663,156 | A | 5/1987 | Clum et al. |
| 4,683,134 | A | 7/1987 | Palinczar |
| 4,686,099 | A | 8/1987 | Palinczar |
| 4,699,779 | A | 10/1987 | Palinczar |
| 4,701,321 | A | 10/1987 | Bernstein |
| 4,749,501 | A | 6/1988 | Nakagawa et al. |
| 4,803,195 | A | 2/1989 | Holzner |
| 4,874,538 | A | 10/1989 | Dawson et al. |
| 4,904,524 | A | 2/1990 | Yoh |
| 4,933,174 | A | 6/1990 | Bernstein |
| 4,985,170 | A | 1/1991 | Dawson et al. |
| 5,071,706 | A | 12/1991 | Soper et al. |
| 5,089,269 | A | 2/1992 | Noda et al. |
| 5,132,117 | A * | 7/1992 | Speaker .............. A61K 9/5089 264/4.1 |
| 5,169,624 | A | 12/1992 | Ziegler et al. |
| 5,292,801 | A | 3/1994 | Avnir et al. |
| 5,300,564 | A | 4/1994 | Avnir et al. |
| 5,306,485 | A | 4/1994 | Robinson et al. |
| 5,455,048 | A | 10/1995 | Lahmani et al. |
| 5,476,660 | A | 12/1995 | Somasundaran et al. |
| 5,508,259 | A | 4/1996 | Holzner et al. |
| 5,543,136 | A | 8/1996 | Aldous |
| 5,589,177 | A | 12/1996 | Herb et al. |
| 5,614,217 | A | 3/1997 | Chiprich et al. |
| 5,599,555 | A | 4/1997 | El-Nokaly |
| 5,620,692 | A | 4/1997 | Potter et al. |
| 5,643,341 | A | 7/1997 | Hirsch et al. |
| 5,661,189 | A | 8/1997 | Grieveson et al. |
| 5,674,912 | A | 10/1997 | Martin |
| 5,683,716 | A | 11/1997 | Hata et al. |
| 5,716,920 | A | 2/1998 | Glenn et al. |
| 5,733,531 | A | 3/1998 | Mitchnick et al. |
| 5,759,524 | A | 6/1998 | Tanner et al. |
| 5,770,556 | A | 6/1998 | Farrell et al. |
| 5,785,979 | A | 7/1998 | Wells |
| 5,849,273 | A | 12/1998 | Bonda et al. |
| 5,876,755 | A | 2/1999 | Perring et al. |
| 5,900,394 | A | 5/1999 | Goel et al. |
| 5,904,917 | A | 5/1999 | Mattai et al. |
| 5,914,101 | A | 5/1999 | Mattai et al. |
| 5,948,416 | A | 9/1999 | Wagner et al. |
| 5,955,409 | A | 9/1999 | Farrell et al. |
| 5,989,529 | A | 11/1999 | Kaplan |
| 5,989,536 | A | 11/1999 | Deckner et al. |
| 6,024,942 | A | 2/2000 | Tanner et al. |
| 6,043,204 | A | 3/2000 | Kaufman et al. |
| 6,057,275 | A | 5/2000 | Fair et al. |
| 6,074,630 | A | 6/2000 | Devillez et al. |
| 6,096,697 | A | 8/2000 | Wells |
| 6,110,888 | A | 8/2000 | Lupo, Jr. et al. |
| 6,159,453 | A | 12/2000 | Avnir et al. |
| 6,217,852 | B1 | 4/2001 | Gildenberg et al. |
| 6,224,852 | B1 | 5/2001 | Morgan et al. |
| 6,238,650 | B1 | 5/2001 | Lapidot et al. |
| 6,248,364 | B1 | 6/2001 | Sengupta et al. |
| 6,248,703 | B1 | 6/2001 | Finucane et al. |
| 6,255,264 | B1 | 7/2001 | Fleurot et al. |
| 6,303,149 | B1 | 10/2001 | Magdassi et al. |
| 6,348,218 | B1 | 2/2002 | Hed et al. |
| 6,362,146 | B1 | 3/2002 | MacAulay |
| 6,391,287 | B1 | 5/2002 | Baldo et al. |
| 6,395,269 | B1 | 5/2002 | Fuller et al. |
| 6,399,045 | B1 | 6/2002 | Morgan et al. |
| 6,412,658 | B1 | 7/2002 | Bartholomew et al. |
| 6,436,375 | B1 | 8/2002 | Lapidot et al. |
| 6,468,509 | B2 | 10/2002 | Lapidot et al. |
| 6,471,975 | B1 | 10/2002 | Banovetz et al. |
| 6,485,713 | B1 | 11/2002 | Bonda et al. |
| 6,491,902 | B2 | 12/2002 | Shefer et al. |
| 6,500,791 | B2 | 12/2002 | Pereira et al. |
| 6,524,594 | B1 | 2/2003 | Santora et al. |
| 6,555,095 | B1 | 4/2003 | Garrison |
| 6,576,228 | B1 | 6/2003 | Crookham et al. |
| 6,607,713 | B1 | 8/2003 | Chodorowski et al. |
| 6,696,067 | B2 | 2/2004 | Brandt et al. |
| 6,699,824 | B1 | 3/2004 | Dawson et al. |
| 6,740,631 | B2 | 5/2004 | Shefer et al. |
| 6,770,270 | B2 | 8/2004 | Bonda |
| 6,825,161 | B2 | 11/2004 | Shefer et al. |
| 6,855,335 | B2 | 2/2005 | Seok et al. |
| 6,913,825 | B2 | 7/2005 | Ostafin et al. |
| 6,998,113 | B1 | 2/2006 | Traynor et al. |
| 7,001,592 | B1 | 2/2006 | Traynor et al. |
| 7,025,952 | B1 | 4/2006 | Traynor et al. |
| 7,037,513 | B1 | 5/2006 | Traynor et al. |
| 7,053,034 | B2 | 5/2006 | Shefer et al. |
| 7,074,747 | B1 | 7/2006 | Lukenbach et al. |
| 7,098,032 | B2 | 8/2006 | Trubetskoy et al. |
| 7,138,382 | B2 | 11/2006 | Wolff et al. |
| 7,226,582 | B2 | 6/2007 | Traynor et al. |
| 7,226,607 | B2 * | 6/2007 | Uchiyama .............. A61L 9/012 424/401 |
| 8,039,015 | B2 | 10/2011 | Speaker |
| 2002/0028235 | A1 | 3/2002 | Reed et al. |
| 2002/0034487 | A1 | 3/2002 | Maubru et al. |
| 2002/0064541 | A1 | 5/2002 | Lapidot et al. |
| 2002/0077256 | A1 | 6/2002 | Niemiec et al. |
| 2002/0131939 | A1 | 9/2002 | Djerassi et al. |
| 2002/0167404 | A1 | 11/2002 | Jordan |
| 2003/0032593 | A1 | 2/2003 | Wender et al. |
| 2003/0059382 | A1 | 3/2003 | Brandt et al. |
| 2003/0059383 | A1 | 3/2003 | SaNogueira et al. |
| 2003/0108580 | A1 | 6/2003 | Hasenzahl et al. |
| 2003/0134761 | A1 | 7/2003 | Sebillotte-Arnaud et al. |
| 2003/0147818 | A1 | 8/2003 | Dubief et al. |
| 2003/0171230 | A1 | 9/2003 | Shana'a et al. |
| 2003/0176303 | A1 | 9/2003 | Niemiec et al. |
| 2003/0187665 | A1 | 10/2003 | Boyd |
| 2004/0005278 | A1 | 1/2004 | Reinhart et al. |
| 2004/0028709 | A1 | 2/2004 | Dueva et al. |
| 2004/0047826 | A1 | 3/2004 | Brown |
| 2004/0101498 | A1 | 5/2004 | Koshti et al. |
| 2004/0120905 | A1 | 6/2004 | Gall et al. |
| 2004/0167046 | A1 | 8/2004 | Lukenbach et al. |
| 2004/0169298 | A1 | 9/2004 | Fukasawa et al. |
| 2004/0234558 | A1 | 11/2004 | O'Conner et al. |
| 2004/0247536 | A1 | 12/2004 | Chaudhuri |
| 2004/0247543 | A1 | 12/2004 | Huerta et al. |
| 2005/0065047 | A1 | 3/2005 | Shefer et al. |
| 2005/0123611 | A1 | 6/2005 | Barbe et al. |
| 2005/0255055 | A1 | 11/2005 | Wagner et al. |
| 2006/0018966 | A1 | 1/2006 | Lin et al. |
| 2006/0073106 | A1 | 4/2006 | Berg-Schultz et al. |
| 2006/0135645 | A1 | 6/2006 | Glassel et al. |
| 2007/0028400 | A1 | 2/2007 | Wolber et al. |
| 2007/0292676 | A1 | 12/2007 | Naigertsik et al. |
| 2008/0112904 | A1 | 5/2008 | Traynor et al. |
| 2008/0317795 | A1 | 12/2008 | Traynor et al. |
| 2009/0280149 | A1 | 11/2009 | Tajima et al. |
| 2009/0324655 | A1 | 12/2009 | Polonka et al. |
| 2010/0015188 | A1 | 1/2010 | Izu et al. |
| 2010/0092410 | A1 | 4/2010 | Cockerell et al. |
| 2010/0135936 | A1 | 6/2010 | Dueva-Koganov et al. |
| 2011/0020253 | A1 | 1/2011 | Doyle et al. |
| 2011/0150795 | A1 | 6/2011 | Loing et al. |
| 2011/0206793 | A1 | 8/2011 | Hines et al. |

(56) References Cited

U.S. PATENT DOCUMENTS

| | | | |
|---|---|---|---|
| 2012/0141395 | A1 | 6/2012 | Chaudhuri et al. |
| 2012/0148644 | A1 | 6/2012 | Popplewell et al. |
| 2012/0207804 | A1 | 8/2012 | Traynor et al. |
| 2014/0127275 | A1 | 8/2014 | Cohen |
| 2017/0216165 | A1 | 8/2017 | Traynor et al. |
| 2018/0125980 | A1 | 5/2018 | Finley et al. |

FOREIGN PATENT DOCUMENTS

| | | |
|---|---|---|
| EP | 0254447 B1 | 3/1993 |
| EP | 0399911 B1 | 7/1993 |
| EP | 1162942 B1 | 6/2004 |
| WO | 1992016195 A1 | 10/1992 |
| WO | 9845036 A1 | 10/1998 |
| WO | 9943296 A2 | 9/1999 |
| WO | 9943296 A3 | 11/1999 |
| WO | 0042985 A1 | 7/2000 |
| WO | 0057850 A1 | 10/2000 |
| WO | 2005009602 A2 | 2/2005 |
| WO | 2005009602 A3 | 1/2006 |
| WO | 2008144734 A1 | 11/2008 |
| WO | 2010000587 A2 | 1/2010 |
| WO | 2012074250 A2 | 6/2012 |
| WO | 2013087548 A2 | 6/2013 |
| WO | 2013107354 A1 | 7/2013 |
| WO | 2014074555 A1 | 5/2014 |
| WO | 2014132261 A2 | 9/2014 |
| WO | 2017139701 A2 | 8/2017 |

OTHER PUBLICATIONS

Karr, Jennifer I., Tycho J. Speaker, and Gerald B. Kasting. "A novel encapsulation of N, N-diethyl-3-methylbenzamide (DEET) favorably modifies skin absorption while maintaining effective evaporation rates." Journal of controlled release 160.3 (2012): 502-508. Especially Figure 1.*
Boissiere, et al. "Turning biopolymer particles into hybrid capsules: the example od silica/alginate nanocomposites" J. Mater. Chem. 2006; 16:1178-1182.
Business Wire, Oct. 5, 1999, Business Wire, Leading Cosmetics Industry Chemist Joins Skin Innovator; Performance Brands Names Michael Dulak to Board of Directors Best Availabe Copy.
Copyrightkids.org, http://web.archive.org/web/20030919013921 /http://www.copyrightkids.org/definitions. html, Retrieved via WayBack Machine with archive date of Sep. 19, 2003.
Datachem Software Developers of CertiStep, License Agreements, http://web.archive.org/web/20031109074418/http://www.datachemsoftware.com/licenses.htm, retrieved via Wayback Machine with archive date of Nov. 9, 2003.
Donahue "Intellectual Property Licensing: a crib sheet for deal makers", copyright 1998, http://teklaw.com/iplicens.htm.
Ford "Sunscreen How Products Are Made" Find Articles at BNET, vol. 2, 1994, Retrieved from http://www.findarticles.com.
Ghosh "Functional Coatings and Microencapsulation: A general perspective" Wiley-VCH Verlag GmbH & Co KgaA, Weinheim ISBN 3-527-31296-X; 2006:1-28.
International Search Report, PCT/US2013/068651, dated Mar. 5, 2014.
UCLA Trademarks and Licensing, http://web.archive.org/web/20030811091818/http://www.asucla.ucla.edu/licensing/index.asp, Retrieved via Wayback Machine with archive date of Aug. 11, 2003.
Written Opinion and International Search Report, PCT/US06/03365, dated May 24, 2006.
Yeh, et al. "Synthesis of Hollow Silica Spheres with Mesostructed Shell Using Cationic-Anionic-Neutral Block Copolymer Ternary Surfactants" Langmuier 2006; 22(1): 6-9.
Donaldson et al., "Ultrafine particles," Occupational and Environmental Medicine, (2001), vol. 58, No. 3, pp. 211-216.
Klykken et al., "Silicone Film-Forming Technologies for Health Care Applications," Dow Corning [online], Jun. 16, 2009.
Karr, et al., A Novel Encapsulation of N,N-diethyl-3-methylbenzamide (DEET) Facorably Modifies Skin Absorption while Maintaining Effective Evaporation Rates, J. Controlled Release 160:502-508 (2012).
PCT Form ISA 237, Written Opinion, PCT/US2013/068651, dated Mar. 5, 2014.
PCT Form IB 373, International Preliminary Report on Patentability, PCT/US2013/068651, dated May 12, 2015.
PCT Form ISA 210, International Search Report, PCT/US2017/017556, dated Feb. 10, 2017.
PCT Form ISA 237, Written Opinion, PCT/US2017/017556, dated Feb. 10, 2017.
EPO, Supplemental Search Report, dated Apr. 15, 2016.
Xiong, et al., Complex Coacervation of Ovalbumin-Carboxymethylcellulose Assessed by Isothermal Titration Calorimeter and Rheology: Effect of Ionic Strength and Charge Density of Polysaccharides, Food Hydrocolloids 73: 41-50 (2017).
PCT Form ISA 210, International Search Report, PCT/US2018/017720, dated May 14, 2018.
PCT Form ISA 210, International Search Report, PCT/US2018/017722, dated Jun. 5, 2018.
PCT Form ISA 237, Written Opinion, PCT/US2018/017720, dated May 14, 2018.
PCT Form ISA 237, Written Opinion, PCT/US2018/017722, dated Jun. 5, 2018.
Sanar, website (2016).
Mcpartland, Cannabis as Repellent and Pesticide, pp. 17 (1997).

* cited by examiner

FIG. 3A
FIG. 3B
FIG. 3C
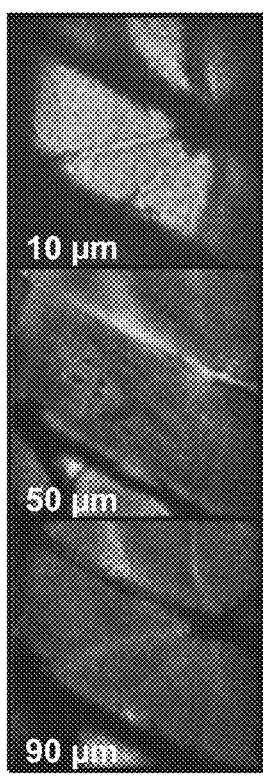
FIG. 3D
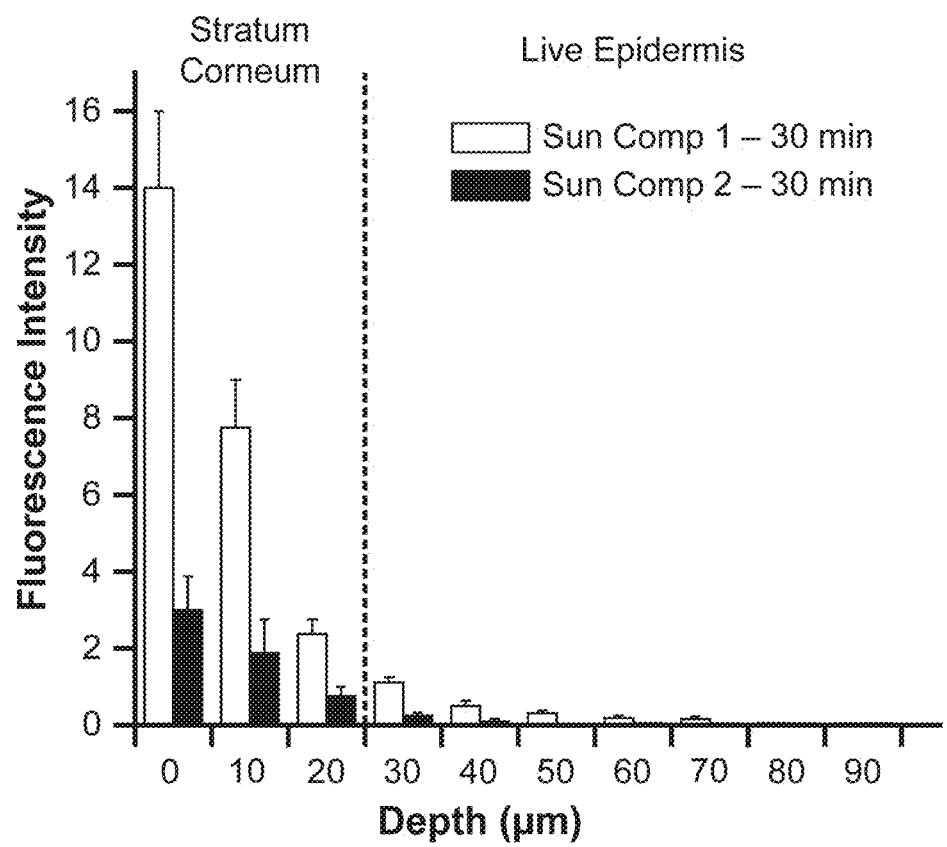

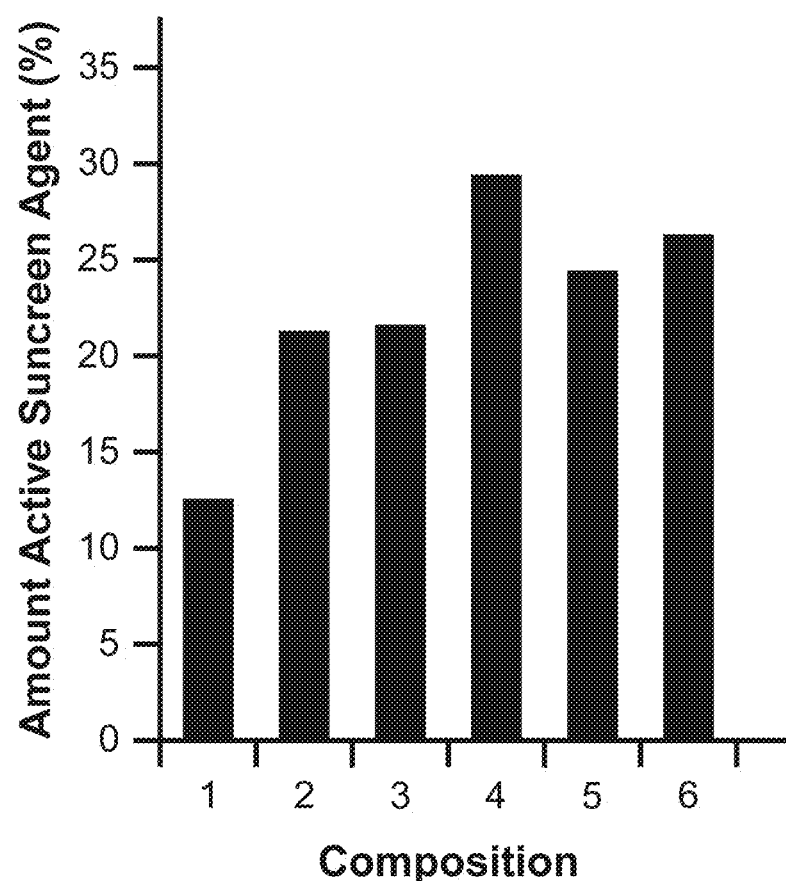

COMPOSITIONS CONTAINING A FLEXIBLE DERIVED CAPSULE WITH AN ACTIVE AGENT

This continuation-in-part application claims the benefit of priority and the filing date pursuant to 35 U.S.C. § 120 to U.S. Non-Provisional Ser. No. 15/430,416, filed Feb. 10, 2017, a continuation-in-part application that claims priority pursuant to 35 U.S.C. § 119(e) to U.S. Provisional Patent Application 62/293,703, filed Feb. 10, 2016 and that claims priority to U.S. Non-Provisional Ser. No. 14/702,615, filed May 1, 2015, now U.S. Pat. No. 9,592,184, a continuation application that claims priority to U.S. Non-Provisional Ser. No. 14/072,926, filed Nov. 6, 2013, now U.S. Pat. No. 9,456,966, which claims priority pursuant to 35 U.S.C. § 119(e) to U.S. Provisional Patent Application 61/769,758, filed Feb. 27, 2013 and U.S. Provisional Patent Application 61/722,870, filed Nov. 6, 2012; and this continuation-in-part application claims the benefit of priority and the filing date pursuant to 35 U.S.C. § 120 to International Patent Application PCT/US2017/017556, filed Feb. 10, 2017, a PCT application that claims priority to U.S. Provisional Patent Application 62/293,703, filed Feb. 10, 2016, each of which is hereby incorporated by reference in its entirety.

Compositions comprising microcapsules enclosing one or more agents for the purpose of controlling their release is known in the pharmaceutical, medical, cosmetics, and other industries. The microcapsules may additionally be surrounded by one or more agents. Existing microcapsules tend to be rigid, such that application of mechanical force will cause the microcapsules to break, releasing the agents contained therewithin. In the case of a cosmetic, therapeutic, or other products applied to the body, breakage of the microcapsules may reduce the effectiveness of the composition and release encapsulated agents. The released agents may thereafter be undesirably absorbed into the body (e.g., through the skin) or absorbed all at once when a there is a need to absorb the active ingredients over a period of time. Further, once broken, existing microcapsules tend to more easily rinse off or have an oily or other unacceptable feel on the skin, hair, etc. In addition to the loss of coverage due to perspiration, absorption, and rinsing, existing encapsulation compositions also suffer from uneven application.

In spite prior attempts, there remains an unmet need for an effective encapsulated product that provides an effective means to apply an agent to the body, particularly an encapsulated product that remains effective even after rinsing one or more times following application as well as having a gentle or acceptable feel on the human skin, as opposed to an oily feel. What is needed is a microcapsule that is able to contain one or more agents without substantial breakage or with controlled breakage over a period of time or through activity, and yet, has a gentle or acceptable feel on the human skin. The present invention addresses one or more of these needs by utilizing encapsulation technologies, milder surfactant systems, and good adhesive polymers that provide a strong binding capability, making it more efficient for deposition of the one or more agents contained therein and/or therearound. The disclosed capsules also lay down on the skin surface in a manner that result in packing and spreading of the agent over the skin surface or other portion of an individual. The disclosed capsules also provide a means for formulating various agents that can result in a greater amount of active agent after application through such products as shampoo, body wash, conditioner, lotion, mousse, spray, hand sanitizer, cream and gel.

SUMMARY

Aspects of the present specification disclose compositions comprising one or more encapsulates comprising one or more agents and methods and uses for the disclosed agents. The disclosed encapsulates can be cellulose derived encapsulates and/or sol-gel encapsulates. In aspects, the one or more agents include one or more arachnid/insect repellents. A composition disclosed herein may further comprise one or more flexible capsules comprising one or more polyquarterniums, one or more surfactants, one or more film formers, one or more emollients, one or more thickening agents, one or more soap bases, one or more polymers, one or more fragrances, or any combination thereof. A composition disclosed herein may be incorporated into a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product.

BRIEF DESCRIPTION OF THE FIGURES

FIG. 3A shows a fluorescent image of dye penetration into human skin at 10 µm from the skin surface; FIG. 3B shows a fluorescent image of dye penetration into human skin at 50 µm from the skin surface; FIG. 3C shows a fluorescent image of dye penetration into human skin at 90 µm from the skin surface; FIG. 3D shows a bar graph of dye penetration into human skin using fluorescence intensity of dye versus penetration depth of dye.

FIG. 4 shows a bar graph comparing the amount of agent needed to achieve an SPF value of 50.

DETAILED DESCRIPTION

Figure 1:
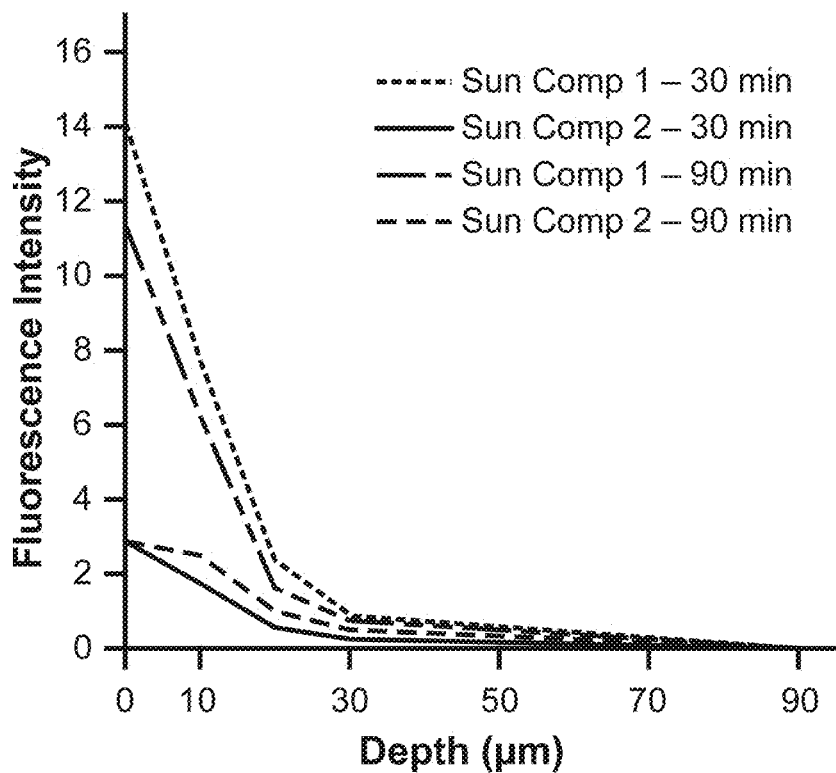
FIG. 1 shows a graph of dye penetration into human skin using fluorescence intensity of dye versus penetration depth of dye. Measurements were taken 30 minutes and 90 minutes after application of a composition.

The present specification encompasses compositions comprising one or more agents enclosed in a capsule (also referred to as "an encapsulate"). An agent, includes, without limitation, an active agent and/or an additional agents disclosed herein. Generally, encapsulation of an agent involves trapping the agent into a vesicle, such as, e.g., a microsphere (or microcapsule) or nanosphere (or nanocapsule). Encapsulation increases the stability of the composition by protecting the encapsulated agent. In addition, encapsulation increases the effectiveness of the composition by creating a encapsulate layer that physically shield the skin layer and provides more complete coverage and even application. Furthermore, encapsulation also minimizes the absorption of an agent disclosed herein into the dermis and subsequent systemic distribution in the body.

A capsule disclosed herein can have a flexible shell. A flexible shell enables for the tight packing of the capsules on the surface of the skin to form an encapsulate layer, prevents breakage or rupture of the capsules upon friction or other external force and/or enables capsule to have high load rates. For example, applications involving a non-encapsulated agent is absorbed directly into the skin within about 1 hour. This is often undesirable or even detrimental because the benefits may be quickly lost and repeated applications are required to maintain adequate coverage of the agent. In addition, absorption of some agents can be toxic to some degree and create health problems for the user. Flexible capsules containing one or more agents form an encapsulation layer on top of the skin surface that acts as a protective barrier. The flexibility of the capsules enable dense packing of the capsules to form a strong cohesive encapsulate layer. Among other things, this encapsulate layer acts like a shield to physically protect a skin surface from harmful environmental exposure, such as, e.g., sunlight, wind, dryness. In addition, since the agents are contained within capsules, absorption into the skin is minimized. This encapsulate layer appears to be maintained on the surface of skin for upwards of 8 or more hours.

In addition, a capsule disclosed herein is designed so as to experience minimal or no leakage of a agent disclosed herein, or decomposition when applied to the skin. A capsule disclosed herein is eventually removed from the skin through repeated washing and/or normal sloughing of the external skin cell layers. Especially for agents used for one-time or very few exposures, such as can occur for personnel engaged in combating or containing terrorist attacks or in warfare, the invention provides a means to deliver a last line of defense on the skin of personnel where the active used in the microcapsules may be one that is not appropriate for long-term use, but that is appropriate for a limited number of applications in order to protect the wearer from a greater risk (e.g., cellulose derived capsule and/or sol-gel capsules, including, without limitation, microcapsules, encapsulating lead to protect against a radiation attack).

Further, the mechanical properties at least some or all of the capsules may be selected to provide an exfoliating effect by acting as an exfoliant in the composition. Exfoliant compounds act an abrasive for sloughing away the outermost layer of dead skin cells from the epidermis, which may smooth the skin, promote blood circulation, and/or increase the turnover of surface skin cells. At least some of the capsule materials are selected to be sufficiently hard to achieve removal of the dead skin through mechanical exfoliation (e.g., by scrubbing, etc.).

The compositions may also be formulated with cationic polymer in a manner that causes the encapsulated agent to adhere or be trapped in a polymer complex to a skin surface, hair shaft, or any substrate which can accept an opposing charge forming a protective layer on the skin or other substrate. The adhesive nature of the encapsulated agent enables the composition to remain on the skin's surface or other surface for longer periods of time relative to conventional compositions without the encapsulates and its packing capability, even after exposure to water or other liquids. In addition, because the active agent remained encapsulated, protection is not lost due to absorption of the active agent into the skin.

A composition disclosed herein can be manufactured as a solid, a liquid, a colloidal, or an aerosol. In addition, a composition disclosed herein can be manufactured into, without limitation, a body wash, a shampoo, a conditioner, a soap, a gel, a hand sanitizer, a cream, a spray, a mouse or a lotion. As such, the disclosed compositions may be easily and conveniently applied during normal hygienic activities, such as, e.g., washing, showering, bathing, after bathing or showering while the skin is still wet, or during routine moisturizing or other hygiene activities, resulting in the application of an effective level of an encapsulated active agent to a skin surface, even after activities that would remove conventional active agents, such as, e.g., washing, rinsing, or swimming.

A capsule can be a cellulose derived capsule and/or a sol-gel capsule. A composition disclosed herein may comprise a cellulose derived capsule comprising one or more agents disclosed herein. A composition disclosed herein may comprise a sol-gel capsule comprising one or more agents disclosed herein. A composition disclosed herein may comprise a cellulose derived capsule, a sol-gel capsule, each comprising one or more agents disclosed herein.

A cellulose derivative for use in a cellulose derived capsule includes without limitation, a cellulose ether or a cellulose ester. Non-limiting examples of a cellulose ether include ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, or any salt therefrom. Non-limiting examples of a cellulose ester include cellulose acetate, cellulose acetate phthalate, cellulose acetate butyrate, cellulose acetate trimelitate, hydroxupropylmethyl cellulose phthalate, or any salt therefrom. Additional cellulose derivatives are described in, e.g., Cellulose: Structure and Properties, Derivatives and Industrial Uses, eds. Lejeune and Deprez, pp. 528 (2010); Cellulose and Cellulose Derivatives, Kenji Kamide, (2005); Doelker, Cellulose Derivatives, pp. 199-265, Advances in Polymer Science, vol. 107 (2005), each of which is hereby incorporated by reference in its entirety. A cellulose derived capsule can be prepared in large quantities without a high reaction time and drying step and the preparation and purification of cellulose derived capsules are well known to a person skilled in the art, see, e.g., U.S. Pat. Nos. 8,039,015 and 8,685,425, each of which is incorporated by reference in its entirety.

In an aspect of this embodiment, a composition contains cellulose derived capsules comprising cellulose, a cellulose ether derivative, a cellulose ester derivative, any salt therefrom, or any combination therefrom. In another aspect of this embodiment, the cellulose derivative a composition contains cellulose derived capsules comprising cellulose, ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, cellulose acetate, cellulose acetate phthalate, cellulose acetate butyrate, cellulose acetate trimelitate, hydroxupropylmethyl cellulose phthalate, any salt therefrom, or any combination therefrom. In an aspect of this embodiment, the cellulose derivative a composition contains cellulose derived capsules comprising cellulose, a cellulose ether derivative, any salt therefrom, or any combination therefrom. In another aspect of this embodiment, the cellulose derivative a composition contains cellulose derived capsules comprising cellulose, ethyl cellulose, methyl cellulose, ethylmethyl cellulose, hydroxyethyl cellulose, hydroxypropyl cellulose, hydroxyethylmethyl cellulose, hydroxypropylmethyl cellulose, ethyl hydroxyethyl cellulose, carboxymethyl cellulose, any salt therefrom, or any combination therefrom. In an aspect of this embodiment, the cellulose derivative a composition contains cellulose derived capsules comprising cellulose, a cellulose ester derivative, any salt therefrom, or any combination therefrom. In another aspect of this embodiment, the cellulose derivative a composition contains cellulose derived capsules comprising cellulose, cellulose acetate, cellulose acetate phthalate, cellulose acetate butyrate, cellulose acetate trimelitate, hydroxupropylmethyl cellulose phthalate, any salt therefrom, or any combination therefrom. In an aspect of this embodiment, the cellulose derivative used in a cellulose derived capsule is hydroxypropylcellulose or a salt therefrom. In an aspect of this embodiment, the cellulose derivative used in a cellulose derived capsule is carboxymethylcellulose or a salt therefrom, such as, e.g., sodium carboxymethyl cellulose.

A sol-gel capsules are prepared by emulsifying hydrophobic solution comprising sol-gel precursors and at least one active agents in an aqueous solution under high shear forces and mixing and stirring the obtained emulsion with a second aqueous solution at a suitably selected pH to obtain the sol-gel capsules. The size of the microcapsules so obtained can be controlled, by selecting suitable reaction conditions. The sol-gel precursors can be a metal or a semi-metal alkoxide monomers, or a partially hydrolyzed and partially condensed polymer thereof, or a mixture thereof. The sol-gel precursors can be selected from metal or semi-metal alkoxide monomers, or metal ester monomers, or semi-metal ester monomers or monomers of the formula $M(R)_n(P)_m$, wherein M is a metallic or semi metallic element, R is a hydrolyzable substituent, n is an integer from 2 to 6, P is a non polymerizable substituent and m is and integer from 0 to 6, or partially hydrolyzed and partially condensed polymer thereof, or any mixture thereof. The methods of encapsulation of sol-gel encapsulation are well known to a person skilled in the art, see, e.g., U.S. Pat. Nos. 6,238,650; 6,436,375, 6,303,149; 6,468,509; 7,037,513; 8,974,709; and 9,192,548; and US Patent Application Publications US 2008/0317795 and US 2011/0256304, each of which is incorporated by reference in its entirety.

In an embodiment, a capsule disclosed herein has sufficient size to form a protective or desired layer on top of a skin surface after application of a composition disclosed herein. If capsules are too large, its size will reduce or disrupt the formation of an encapsulate layer, thereby reducing the packing of encapsulates which in turn will reduce coverage on the skin or other part of the body. In aspects of this embodiment, a capsule disclosed herein has a diameter of, e.g., at least 200 nm, at least 250 nm, at least 300 nm, at least 350 nm, at least 400 nm, at least 450 nm, at least 500 nm, at least 550 nm, at least 600 nm, at least 650 nm, at least 700 nm. In other aspects of this embodiment, a cellulose derived capsule has a diameter of, e.g., at most 200 nm, at most 250 nm, at most 300 nm, at most 350 nm, at most 400 nm, at most 450 nm, at most 500 nm, at most 550 nm, at most 600 nm, at most 650 nm, at most 700 nm.

In aspects of this embodiment, a capsule disclosed herein has a diameter of, e.g., about 200 nm to about 250 nm, about 200 nm to about 300 nm, about 200 nm to about 350 nm, about 200 nm to about 400 nm, about 200 nm to about 450 nm, about 200 nm to about 500 nm, about 200 nm to about 550 nm, about 200 nm to about 600 nm, about 200 nm to about 650 nm, about 200 nm to about 700 nm, about 250 nm to about 300 nm, about 250 nm to about 350 nm, about 250 nm to about 400 nm, about 250 nm to about 450 nm, about 250 nm to about 500 nm, about 250 nm to about 550 nm, about 250 nm to about 600 nm, about 250 nm to about 650 nm, about 250 nm to about 700 nm, about 300 nm to about 350 nm, about 300 nm to about 400 nm, about 300 nm to about 450 nm, about 300 nm to about 500 nm, about 300 nm to about 550 nm, about 300 nm to about 600 nm, about 300 nm to about 650 nm, about 300 nm to about 700 nm, about 350 nm to about 400 nm, about 350 nm to about 450 nm, about 350 nm to about 500 nm, about 350 nm to about 550 nm, about 350 nm to about 600 nm, about 350 nm to about 650 nm, about 350 nm to about 700 nm, about 400 nm to about 450 nm, about 400 nm to about 500 nm, about 400 nm to about 550 nm, about 400 nm to about 600 nm, about 400 nm to about 650 nm, about 400 nm to about 700 nm, about 450 nm to about 500 nm, about 450 nm to about 550 nm, about 450 nm to about 600 nm, about 450 nm to about 650 nm, about 450 nm to about 700 nm, about 500 nm to about 550 nm, about 500 nm to about 600 nm, about 500 nm to about 650 nm, about 500 nm to about 700 nm, about 550 nm to about 600 nm, about 550 nm to about 650 nm, about 550 nm to about 700 nm, about 600 nm to about 650 nm, about 600 nm to about 700 nm or about 650 nm to about 700 nm.

In an embodiment, a capsule disclosed herein can comprise one layer. In another embodiment, a capsule disclosed herein can comprise multiple layers. In aspects of this embodiment, a capsule disclosed herein comprises two or more layers, three or more layers, four or more layers, or five or more layers.

In an embodiment, a capsule disclosed herein is designed to not have one or more agents contained therein to be absorb or otherwise penetrate, or minimize such absorption/penetration, into the epidermal layer of the skin. In an embodiment, a capsule disclosed herein is designed to not have one or more agents contained therein absorbed or otherwise penetrate through the epidermal layer of the skin. In aspects of this embodiment, a capsule disclosed herein is designed to not have one or more agents contained therein to be substantially absorbed or otherwise penetrate through the stratum corneum into the live epidermal layer of the skin. In aspects of this embodiment, a capsule disclosed herein is designed to have only, e.g., at most 1%, at most 5%, at most 10%, at most 15%, at most 20% or at most 25% of the one or more agents absorbed or otherwise penetrate through the stratum corneum into the live epidermal layer of the skin.

In aspects of this embodiment, an agent disclosed herein may be absorbed or otherwise penetrate the epidermal layer of the skin by only, e.g., about 0.1 μm, about 0.5 μm, about 1 μm, about 5 μm, about 10 μm, about 15 μm, about 20 μm, about 30 μm, about 40 μm, about 50 μm, about 60 μm, about 70 μm, about 80 μm, about 90 μm or about 100 μm. In other aspects of this embodiment, an agent disclosed herein may be absorbed or otherwise penetrate the epidermal layer of the skin by only, e.g., at most about 0.1 μm, at most 0.5 μm, at most 1 μm, at most 5 μm, at most 10 μm, at most 15 μm, at most 20 μm, at most 30 μm, at most 40 μm, at most 50 μm, at most 60 μm, at most 70 μm, at most 80 μm, at most 90 μm or at most 100 μm. In yet other aspects of this embodiment, an agent disclosed herein may be absorbed or otherwise penetrate the epidermal layer of the skin by only, e.g., about 0.1 mm to about 1 μm, about 0.1 mm to about 5 μm, about 0.1 mm to about 10 μm, about 0.1 mm to about 15 μm, about 0.1 mm to about 20 μm, about 0.1 mm to about 25 μm, about 0.1 mm to about 30 μm, about 0.1 mm to about 40 μm, about 0.1 mm to about 50 μm, about 0.1 mm to about 60 μm, about 0.1 mm to about 70 μm, about 0.1 mm to about 80 μm, about 0.1 mm to about 90 μm, about 0.1 mm to about 100 μm, about 0.5 mm to about 1 μm, about 0.5 mm to about 5 μm, about 0.5 mm to about 10 μm, about 0.5 mm to about 15 μm, about 0.5 mm to about 20 μm, about 0.5 mm to about 25 μm, about 0.5 mm to about 30 μm, about 0.5 mm to about 40 μm, about 0.5 mm to about 50 μm, about 0.5 mm to about 60 μm, about 0.5 mm to about 70 μm, about 0.5 mm to about 80 μm, about 0.5 mm to about 90 μm, about 0.5 mm to about 100 μm, about 1 mm to about 5 μm, about 1 mm to about 10 μm, about 1 mm to about 15 μm, about 1 mm to about 20 μm, about 1 mm to about 25 μm, about 1 mm to about 30 μm, about 1 mm to about 40 μm, about 1 mm to about 50 μm, about 1 mm to about 60 µm, about 1 mm to about 70 µm, about 1 mm to about 80 µm, about 1 mm to about 90 µm, about 1 mm to about 100 µm, about 5 mm to about 10 µm, about 5 mm to about 15 µm, about 5 mm to about 20 µm, about 5 mm to about 25 µm, about 5 mm to about 30 µm, about 5 mm to about 40 µm, about 5 mm to about 50 µm, about 5 mm to about 60 µm, about 5 mm to about 70 µm, about 5 mm to about 80 µm, about 5 mm to about 90 µm, about 5 mm to about 100 µm, about 10 mm to about 15 µm, about 10 mm to about 20 µm, about 10 mm to about 25 µm, about 10 mm to about 30 µm, about 10 mm to about 40 µm, about 10 mm to about 50 µm, about 10 mm to about 60 µm, about 10 mm to about 70 µm, about 10 mm to about 80 µm, about 10 mm to about 90 µm or about 10 mm to about 100 µm.

A capsule disclosed herein may be designed to be stable or unstable. Stability includes mechanical stability as well as photostability (providing stabilization of photosensitive drugs). Mechanical stability refers to the degree of encapsulate breakage or disintegrate following exposure to physical forces. Photostability refers to the degree of encapsulate breakage or disintegrate following exposure to the sun or UV radiation. Upon breakage of encapsulates their internal contents, including, an active agent, and/or a photostabilizing agent, and/or an additional agent disclosed herein are released onto a skin surface.

In an embodiment, a capsule disclosed herein is prepared so to experience no or minimal breakage when applied to a skin surface. In another embodiment, a capsule disclosed herein is prepared so to experience various degrees of breakage, on average, when applied to a skin. In an aspect of this embodiment, a capsule disclosed herein is formulated so as to break open in response to conditions that occur on a skin surface, so that after application the capsules act to release their contents in a time-release or controlled manner. For example, skin or hair conditions can vary with the user's environment, a variation which can trigger breakage of capsules, include, without limitation, dryness of the skin surface, dryness of hair, pH, temperature, friction, exposure to light and exposure to air.

In an embodiment, a capsule disclosed herein may be prepared so as to experience about 0% breakage, or breakage in a range of from about 1% to about 100%. In aspects of this embodiment, a capsule disclosed herein may be prepared so as to experience breakage of, e.g., at least 10%, at least 20%, at least 30%, at least 40%, at least 50%, at least 60%, at least 70, at least 80%, at least 90%, or at least 95% after application to a skin surface. In other aspects of this embodiment a capsule disclosed herein may be prepared so as to experience breakage of, e.g., at most 10%, at most 20%, at most 30%, at most 40%, at most 50%, at most 60%, at most 70, at most 80%, at most 90%, or at most 95% after application to a skin surface. In yet other aspects of this embodiment, a capsule disclosed herein may be prepared so as to experience breakage in a range of, e.g., about 10% to about 20%, about 10% to about 30%, about 10% to about 40%, about 10% to about 50%, about 10% to about 60%, about 10% to about 70%, about 10% to about 80%, about 10% to about 90%, about 10% to about 100%, about 20% to about 30%, about 20% to about 40%, about 20% to about 50%, about 20% to about 60%, about 20% to about 70%, about 20% to about 80%, about 20% to about 90%, about 20% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, about 90% to about 100% after application to a skin surface.

Aspects of the present specification, disclose a moisturizing agent. A moisturizing agent prevents loss of moisture and/or hydrates the skin and/or increases the water content of the skin and/or replaces the oils contained in the skin. A moisturizing agent includes, without limitation, an occlusive, which works by forming a thin film on the surface of the skin to prevent moisture loss, a humectant, which attracts water vapor from the air to moisturize the skin, and a restoration agent, which restore natural moisturizing factors to the skin. A moisturizing agent includes, without limitation, an emollient, which works by softening or soothing the skin. A moisturizing agent can be used as an after-care treatment of excessive sun exposure or sunburn. A moisturizing agent includes, without limitation, glycerin, chamomile, *aloe*, cetyl alcohol, grape seed oil, dimethicone, an alpha hydroxy acid, a silicone-based agent, a petrolatum-based agent and an antioxidant. A silicone-based agent includes, without limitation, cyclopentasiloxane, cyclohexasiloxane, cyclomethicone, dimethicone and phenyl trimethicone.

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

Other examples of moisturizing agents that can be used with the compositions of the present invention include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canol a oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera bien-*

*nis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, Macadamia *ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

An alpha hydroxy acid includes, without limitation, glycolic acid, lactic acid, malic acid, citric acid and tartaric acid. An antioxidant includes, without limitation, 6-Hydroxymelatonin, acetyl-L-carnitine, a carotene, curcumin, edaravone, glutathione, hydroxytyrosol, L-carnitine, ladostigil, a lipoic acid like alpha-lipoic acid, melatonin, mofegiline, N-acetylcysteine, N-acetylserotonin, oleocanthal, oleuropein, a polyphenol, rasagiline, resveratrol, selegiline, selenium, tirlazad, tyrosol, uric acid, ubiquinol, ubiquinone, a vitamin A like a carotenoid, a vitamin C like an ascorbic acid, and a vitamin E like a tocopherol and a tocotrienol.

The benefit of an encapsulated moisturizing active agent (such as glycerin) over a free moisturizing agent (non-encapsulated) is that it improves the moisturizing properties. The encapsulates form a layered barrier on the skin that prevents drying and keeps moisture within the skin. In addition, as a portion of the encapsulates break through, e.g., through surface friction, the breakage releases the moisturizing active agent contained within the ruptured encapsulate.

In an embodiment, one or more one or more moisturizing agents disclosed herein are encapsulated. In aspects of this embodiment, one or more moisturizing agents disclosed herein are encapsulated in a cellulose derived capsule. In other aspects of this embodiment, one or more moisturizing agents disclosed herein are encapsulated in a cellulose derived capsule and one or more moisturizing agents disclosed herein are not encapsulated. In aspects of this embodiment, one or more moisturizing agents disclosed herein are encapsulated in a sol-gel capsule. In other aspects of this embodiment, one or more moisturizing agents disclosed herein are encapsulated in a sol-gel capsule and one or more moisturizing agents disclosed herein are not encapsulated.

In an embodiment, a moisturizing agent and/or an additional agent disclosed herein is encapsulated in a cellulose derived capsule. In another embodiment, one or more moisturizing agents and/or additional agents and disclosed herein are encapsulated in a cellulose derived capsule and one or more moisturizing agents and/or one or more additional agents disclosed herein are not encapsulated. In another embodiment, one or more additional agents disclosed herein are not encapsulated. In another embodiment, one or more one or more moisturizing agents disclosed herein are encapsulated, but one or more additional agents disclosed herein are not encapsulated.

In an embodiment, a moisturizing agent and/or an additional agent disclosed herein is encapsulated in a sol-gel capsule. In another embodiment, one or more moisturizing agents and/or additional agents and disclosed herein are encapsulated in a sol-gel capsule and one or more moisturizing agents and/or one or more additional agents disclosed herein are not encapsulated. In another embodiment, one or more additional agents disclosed herein are not encapsulated. In another embodiment, one or more one or more moisturizing agents disclosed herein are encapsulated, but one or more additional agents disclosed herein are not encapsulated.

In an embodiment, a moisturizing agent and/or an additional agent disclosed herein is encapsulated in a cellulose derived capsule and a sol-gel capsule. In another embodiment, one or more moisturizing agents and/or additional agents and disclosed herein are encapsulated in a cellulose derived capsule and a sol-gel capsule and one or more moisturizing agents and/or one or more additional agents disclosed herein are not encapsulated. In another embodiment, one or more additional agents disclosed herein are not encapsulated. In another embodiment, one or more one or more moisturizing agents disclosed herein are encapsulated, but one or more additional agents disclosed herein are not encapsulated. In yet another embodiment, a moisturizing agent and, optionally, an additional agent disclosed herein is encapsulated in a cellulose derived capsule; and an additional agent disclosed herein is encapsulated in a sol-gel capsule. In another embodiment, a moisturizing agent and, optionally, an additional agent disclosed herein is encapsulated in a sol-gel capsule; and an additional agent disclosed herein is encapsulated in a cellulose derived capsule. In a further embodiment, a first moisturizing agent and, optionally, an additional agent disclosed herein is encapsulated in a cellulose derived capsule; and at least a second moisturizing agent and, optionally, an additional agent disclosed herein is encapsulated in a sol-gel capsule.

Aspects of the present specification, disclose an arachnid/insect repellent. An arachnid/insect repellent includes, without limitation, a synthetic chemical compound or a compound purified from a natural source. Non-limiting examples of an arachnid/insect repellent that is a synthetic chemical compound, include, without limitation, N,N-Diethyl-m-toluamide (DEED, dimethyl phthalate, ethyl hexanediol, indalone, di-n-propylisocinchoronate, bicycloheptene, dicarboximide, dimethyl carbate, dimethyl phthalate, metofluthrin, indalone, permethrin, icaridin, nepetalactone, tetrahydrofuraldehyde ethyl butylacetylaminopropionate (IR-3535), p-menthane-3,8-diol (PMD), tricyclodecenyl allyl ether, ethylhexanediol, SS220 ((1S,2'S)-Methylpiperidinyl-3-cyclohexen-1-carboxamide), an anthranilate-based arachnid/insect repellent, such as, e.g., methyl anthranilate, N,N-dimethylanthranilic acid (DMA), ethyl anthranilate (EA), and butyl anthranilate (BA) and hydroxyethyl isobutyl piperidine carboxylate.

Non-limiting examples of an arachnid/insect repellent that is a compound purified from a natural source includes plant-derived materials and sea-life including fish. Plant-derived materials with arachnid/insect repellent activity include, without limitation, plant oils derived from, e.g., *achillea, Andrographis paniculata*, anise, basil, bay, bergamot (e.g., *Monardia fistulosa, Monarda didyma, Citrus bergamia, Monarda punctata*), bitter orange peel, black pepper, calamus, camphor, *cananga* (e.g., java), cardamom, carnation (e.g., *dianthus caryophyllus*), *cassia*, castor, cedar (e.g., hinoki), cedarwood, celery, chamomile, cinnamon, *Citrus aurantium amara, Citrus aurantium dulcis, Citrus unshiu*, clary sage, clove (e.g., *Eugenia caryophyllus*), clove bud, coriander, corn, cotton seed, *Cymbopogon martini, eucalyptus*, lemon *eucalyptus*, evening primrose, fennel, garlic, *geranium*, ginger, grapefruit, guaiacwood, gurjun balsam, hiba, jasmine, jojoba, juniper berry, lavender, lemon grass, lemon, lime, linseed, *Litsea cubeba*, marigold, marjoram, mint, mustard, neem, nutmeg, orange, orris root (e.g., *Iris florentina*), patchouli (e.g., *Pogostemon cablin*), pepper, peppermint (e.g., *Mentha piperita*), pimento berry, pimento leaf, pine needle, pine, rose, rosemary (e.g., *Rosmarinus officinalis*), ryu, sage, sandalwood (e.g., *Santalum album*), sassafras, sesame, soybean, spearmint, spice, spike lavender, starflower, tangerine, tea seed, tea tree, thyme, thulasi, tomato, turmeric, white cedar, white grapefruit, wintergreen and yellow nightshade.

A plant oil or derivative thereof may be extracted from a natural source or synthetically made and include racemic mixtures, enantiomers, diastereomers, hydrates, salts, solvates and metabolites, etc. Such oils generally contains as a major constituent an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of suitable plant oils disclosed herein include, without limitation, α- or β-pinene; α-campholenic aldehyde; α-citronellol; α-isoamyl-cinnamic; α-pinene oxide; α-cinnamic terpinene; α-terpineol (e.g., 1-methyl-4-isopropyl-1-cyclohexen-8-ol); α-terpinene; λ-terpinene; aldehyde C16 (pure); α-phellandrene; amyl cinnamic aldehyde; amyl salicylate; anethole; anisic aldehyde; benzyl acetate; benzyl alcohol; borneol; callicarpenal; carvacrol; carveol; cineole; cinnamaldehyde; cinnamic alcohol; cis-pinane; citral (e.g., 3,7-dimethyl-2,6-octadienal); citronella; citronellal; citronellol, citronellol dextro (e.g., 3-7-dimethyl-6-octen-1-ol); citronellol; citronellyl acetate; citronellyl nitrile; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin, 3-ethoxy-4-hydrobenzaldehyde; p-menthane-3,8-diol; eucalyptol (e.g., cineole); *eucalyptus citriodora; eucalyptus globulus*; eugenol (e.g., 2-methoxy-4-allyl phenol); fenchol; ferniol; florazon (e.g., 4-ethyl-α, α-dimethyl-benzenepropanal); galaxolide; geraniol (e.g., 2-trans-3,7-dimethyl-2,6-octadien-8-ol); geranyl acetate; geranyl nitrile; guaiacol; heliotropin; herbanate (e.g., 3-(1-methyl-ethyl) bicyclo(2,2,1) hept-5-ene-2-carboxylic acid ethyl ester); hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; lavandin; limonene; linalool oxide; linalool; linalool; linalyl acetate; I-methyl acetate; longifolene; mandarin; *mentha*; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate, mineral; musk ambrette; musk ketone; musk xylol; allylisothio-cyanate); myrcene; nerol; neryl acetate; nonyl aldehyde; *myristica fragrans*; para-cymene; para-hydroxy phenyl butanone crystals (e.g., 4-(4-hydroxyphenyl)-2-butanone); passion palmarosa oil; p-cymene; pennyroyal oil; perillaldehyde; petitgrain; phenyl ethyl alcohol (e.g., 1-phenyl ethyl alcohol and 2-phenyl ethyl alcohol); phenyl ethyl propionate (e.g., 1-phenyl ethyl propionate and 2-phenyl ethyl propionate); phenyl ethyl-2-methylbutyrate; pinane hydroperoxide; pinanol; pine ester; pinene; piperonal; piperonyl acetate; piperonyl alcohol; plinol; plinyl acetate; pseudo ionone; pyrethrum; rhodinol; rhodinyl acetate; rosalinsandenol; spirantol; terpinen-4-ol, terpenoid; terpineol; terpinolene; terpinyl acetate; tert-butylcyclohexyl acetate; tetrahydrolinalool; tetrahydrolinalyl acetate; tetrahydromyrcenol; thymol; trans-2-hexenol; trans-anethole and metabolites thereof; turpentine; vanillin (e.g., 4-hydroxy-3-methoxy benzaldehyde); vetiver; vitalizair; and the like.

In an embodiment, an arachnid/insect repellent and/or an additional agent disclosed herein is encapsulated in a capsule. In another embodiment, one or more arachnid/insect repellents and/or additional agents and disclosed herein are encapsulated in a cellulose derived capsule. In another embodiment, one or more arachnid/insect repellents and/or additional agents and disclosed herein are encapsulated in a cellulose derived capsule and one or more arachnid/insect repellents and/or one or more additional agents disclosed herein are not encapsulated. In another embodiment, one or more additional agents disclosed herein are not encapsulated.

In an embodiment, an arachnid/insect repellent and/or an additional agent disclosed herein is encapsulated in a cellulose derived capsule. In another embodiment, one or more arachnid/insect repellents and/or additional agents and disclosed herein are encapsulated in a cellulose derived capsule and one or more arachnid/insect repellents and/or one or more additional agents disclosed herein are not encapsulated. In another embodiment, one or more one or more arachnid/insect repellents disclosed herein are encapsulated, but one or more additional agents disclosed herein are not encapsulated.

In an embodiment, an arachnid/insect repellent and/or an additional agent disclosed herein is encapsulated in a sol-gel capsule. In another embodiment, one or more arachnid/insect repellents and/or additional agents and disclosed herein are encapsulated in a sol-gel capsule and one or more arachnid/insect repellents and/or one or more additional agents disclosed herein are not encapsulated.

In an embodiment, an arachnid/insect repellent and/or an additional agent disclosed herein is encapsulated in a sol-gel capsule. In another embodiment, one or more arachnid/insect repellents and/or additional agents and disclosed herein are encapsulated in a sol-gel capsule and one or more arachnid/insect repellents and/or one or more additional agents disclosed herein are not encapsulated. In another embodiment, one or more additional agents disclosed herein are not encapsulated. In another embodiment, one or more one or more arachnid/insect repellents disclosed herein are encapsulated, but one or more additional agents disclosed herein are not encapsulated.

In an embodiment, an arachnid/insect repellent and/or an additional agent disclosed herein is encapsulated in a cellulose derived capsule and a sol-gel capsule. In another embodiment, one or more arachnid/insect repellents and/or additional agents and disclosed herein are encapsulated in a cellulose derived capsule and a sol-gel capsule and one or more moisturizing agents and/or one or more additional agents disclosed herein are not encapsulated. In another embodiment, one or more additional agents disclosed herein are not encapsulated. In another embodiment, one or more one or more arachnid/insect repellents disclosed herein are encapsulated, but one or more additional agents disclosed herein are not encapsulated. In yet another embodiment, an arachnid/insect repellent and, optionally, an additional agent disclosed herein is encapsulated in a cellulose derived capsule; and an additional agent disclosed herein is encapsulated in a sol-gel capsule. In another embodiment, a arachnid/insect repellent and, optionally, an additional agent disclosed herein is encapsulated in a sol-gel capsule; and an additional agent disclosed herein is encapsulated in a cellulose derived capsule. In a further embodiment, a first arachnid/insect repellent and, optionally, an additional agent disclosed herein is encapsulated in a cellulose derived capsule; and at least a second arachnid/insect repellent and, optionally, an additional agent disclosed herein is encapsulated in a sol-gel capsule.

A composition disclosed herein comprises a cationic polymer to enhance the overall positive charge of the one or more active agents and/or additional agents encapsulated in a cellulose derived capsule or a sol-gel capsule. The overall net positive charge of encapsulates promote and facilitate an electrostatic binding or attachment of encapsulates to a negatively charged molecule or surface, such as, e.g., charged components of skin and/or hair. A cationic polymer disclosed herein is not encapsulated by a cellulose derived capsule or a sol-gel capsule disclosed herein.

A cationic polymer useful in a composition disclosed herein include, without limitation, POLYMER JR (Union Carbide Corp.), a cationic cellulose ether derivative, JAGUAR® (Celanese-Stein Hall), cationic guar gums, GAFQUA™ (GAF Corporation), quaternary vinylpyrrolidone copolymer, CAE (Anjinomoto Co., Inc.), a DL-pyrrolidone carboxylic acid salt of L-cocoyl arginine ethyl ester, and MERQUAT™ (Merck & Co.), including MERQUAT™ 100, a highly charged cationic polymer prepared with dimethyldiallylammonium chloride homopolymer, and MERQUAT™ 550, a highly charged cationic copolymer prepared with dimethyldiallylammonium chloride and acrylamide.

In an embodiment, a cationic polymer includes, without limitation, a quaternium or a polyquarternium. Non-limiting examples of a polyquarternium-1, polyquarternium-2, polyquarternium-4 (CELQUAT L-200), polyquarternium-5, polyquarternium-6, polyquarternium-7, polyquarternium-10, polyquarternium-11, polyquarternium-15, polyquarternium-16, polyquarternium-22, polyquarternium-28, polyquarternium-32, polyquarternium-37, polyquarternium-39, polyquarternium-40, polyquarternium-41, polyquarternium-42, polyquarternium-44, polyquarternium-45, polyquarternium-46, polyquarternium-47 and polyquarternium-64.

A cationic polymer useful in a composition disclosed herein are also described in, e.g., U.S. Pat. Nos. 6,224,852; 3,816,616; 4,272,515; 4,298,494; 4,080,310; 4,048,301; 4,009,256; and 3,186,911, each of which is hereby incorporated by reference in its entirety.

A composition disclosed herein comprises a cationic polymer in an amount sufficient to confer an overall positive charge of the one or more active agents and/or additional agents encapsulated in a cellulose derived capsule or a sol-gel capsule that promotes and facilitates an electrostatic binding or attachment of the encapsulates to a negatively charged molecule or surface, such as, e.g., charged components of skin and/or hair. In aspects of this embodiment, a composition disclosed herein comprises a cationic polymer in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a cationic polymer in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a cationic polymer in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition disclosed herein comprises a film former. As used herein, a film former creates a hydrophobic layer on a skin surface and/or hair that acts as a barrier which promotes and enhances the retention of the one or more encapsulated active agents and/or additional agents, even after exposure to water or other liquids, such as, e.g., by washing, rinsing, or swimming. A film former disclosed herein is not encapsulated by a cellulose derived capsule or a sol-gel capsule disclosed herein. Non-limiting examples of a film former include an acrylic co-polymer, butylated hydroxytoluene (BHT), dimethicone, a lanolin derivative, petrolatum, a polyethylene, a polymer, a silicon derivative, a superfatted oil, a water-insoluble emollient, and a keratin or other protein derivative in an amino acid complex such as cysteine.

Non-limiting examples of a lanolin derivative include, without limitation, an acetylated lanolin.

Non-limiting examples of a water-insoluble emollient include, without limitation, fatty acids such as, e.g., oleic and stearic; fatty alcohols such a as, e.g., s cetyl, and hexadecyl (ENJAY); cocoa butter; shea oil; emollient esters such as, e.g., diisopropyl adipate, benzoic acid esters of $C_9$-$C_{15}$ alcohols, and isononyl iso-nonanoate; alkanes such as, e.g., mineral oil; silicones; such as, e.g., dimethyl polysiloxane and emollient ethers such as, e.g., polyoxypropylene butyl ethers and polyoxypropylene cetyl ethers.

Non-limiting examples of a polyethylene include, without limitation, PERFORMALENE® 400 (New Phase Technologies), a polyethylene having a molecular weight of 400 and PERFORMALENE® 2000 (New Phase Technologies) a polyethylene having a molecular weight of 2000.

Additional non-limiting examples of a film former include acacia gum, cellulose derivatives, guar derivatives, acrylamides copolymer, acrylamide/sodium acrylate copolymer, acrylate/acrylamide copolymer, acrylate/ammonium methacrylate copolymer, acrylates copolymer, acrylates/diacetoneacrylamide copolymer, acrylic/acrylate copolymer, adipic acid/dimethylaminohydroxypropyl diethlenetnamine copolymer, adipic acid/epoxypropyl/diethlenetriamine copolymer, albumen, allyl stearate/VA copolymer, aminoethylacrylate phosphate/acrylate copolymer, ammonium acrylates copolymer, ammonium alginate, ammonium vinyl acetate/acrylates copolymer, AMP acrylates/diacetoneacrylamide copolymer, balsam canada, balsam oregon, balsam peru, balsam tolu, benzoi acid/phthalic anhydride/pentaerythritol/neopentyl glycol/palmitic acid copolymer, benzoin extract, butadiene/acrylonitrile copolymer, butylated urea-formaldehyde resin, butyl benzoic acid/phthalic anhydride trimethylolethane copolymer, butyl ester of ethylene maleic anhydride copolymer, butyl ester of PVM/MA copolymer, calcium carrageenan, calcium/sodium PVM/MA copolymer, carboxymethyl hydroxyethyl cellulose, cellulose gum, collodion, copal, corn starch/aciylainide/sodium acrylate copolymer, damar, diethylene glycolamine/epichlorohydrin/piperazine copolymer, DMJ-IF, dodecandoic acid/cetearyl alcoholglycol copolymer, ethylcellulose, ethylene/acrylate copolymer, ethylene/maleic anhydride copolymer, ethylene/vinyl acetate copolymer, ethyl ester of PVM/fvIA copolymer, flexible collodion, gum benzoin, gutta percha, hydroxybutyl methylcellulose, hydroxyethylcellulose, hydroxyethyl ethyl cellulose, hydroxypropylcellulose, hydroxypropyl guar, hydroxypropyl methylcellulose, isopropyl ester of PVM/MA copolymer, maltodextrin, melamine/formaldehyde resin, methacryloyl ethyl betainelmethacrylates copolymer, nitrocellulose, octylacrylamide/acrylates/butylaminoethylmethaciylate copolymer, octylacrylamide/acrylates copolymer, phthalic anhydride/glycerin/glycidyl decanoate copolymer, phthalic/trimellitic/glycols copolymer, polyacrylamide, polyaciylamidomethylpropane sulfone acid, polyacrylic acid, polybutylene terephthalate, polychlorotrifluoroethylene, polyethylacrylate, polyethylene, polyethylene terephthalate, polyisobutene, polystyrene, polyvinyl acetate, polyvinyl alcohol, polyvinyl butyral, polyvinyl imidazolinium acetate, polyvinyl laurate, polyvinyl methyl ether, potassium carrageenan, PVM/MA copolymer, PVP, PVP/dimethylaminoethymethacrylate copolymer, PVP/eicosene copolymer, PVP/ethyl methacrylate/methacrylic acid copolyerm, PVP/hexadecene copolymer, PVP/VA copolymer, PVP/vinyl acetate/itaconic acid copolymer, rosin, serum albumin, shellac, sodium acrylate/vinyl alcohol, copolymer, sodium carrageen, sodium polymethacrylate, sodium polystyrene sulfonate, starch/ acrylates/acrylamide copolymer, starch diethylaminoethyl ether, steaxyvinyl ether/maleic anhydride copolymer, styrene/acrylate/acrylonitrile copolymer, styrene/acrylate/ammonium methacrylate copolymer, styrene/maleic anhydride copolymer, styrene/PVP copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, toluenesulfonamide/formaldehyde resin, tragacanth gum, vinyl acetate/crotonates copolymer, vinyl acetate/crotonic acid copolymer, vinyl acetate/crotonic acid/methacryloxybenzophenon-1 copolymer, vinyl acetate/crotonic aid/vinyl neodecanoate copolymer, and zein.

A film former useful in a composition disclosed herein include, without limitation, petroleum, an acrylate copolymer (DERMACRYL® 2.0, DERMACRYL® 79, DERMACRYL® AQF, DERMACRYL® C, DERMACRYL® E), a synthetic wax of branched polyalpha olefin polymers (PERFORMA® V 103, 260, 343, 825, 6038), a C28-052 olefin/undecylenic acid copolymer (PERFORMA® V 6112) or MOISTUREGUARD™ (Engelhard), a film former comprising petrolatum, dimethicone, stearamidopropyl dimethylamine, stearate and tocopheryl acetate. A film former useful in a composition disclosed herein are also described in, e.g., U.S. Pat. Nos. 6,838,419, 6,838,088, 6,780,422, 6,531,118, and 5,916,541, each of which is incorporated herein by reference in its entirety.

A composition disclosed herein comprises a film former in an amount sufficient to create a hydrophobic layer on a skin surface and/or hair that acts as a barrier which promotes and enhances the retention of the one or more encapsulated active agents and/or additional agents, even after exposure to water or other liquid. In aspects of this embodiment, a composition disclosed herein comprises a film former in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25%, at least 30%, at least 35% or at least 40% of the total weight of the composition. In other aspects of this embodiment, a composition disclosed herein comprises a film former in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25%, at most 30%, at most 35% or at most 40% of the total weight of the composition.

In other aspects of this embodiment, a composition disclosed herein comprises a film former in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35% or about 20% to about 40% of the total weight of the composition.

In an embodiment, a composition disclosed herein comprises can further comprise a surfactant metal complex to enhance the reflective property or create a reflective property of a composition disclosed herein. A surfactant metal complex disclosed herein is not encapsulated by a cellulose derived capsule disclosed herein.

A composition disclosed herein comprises a surfactant metal complex in an amount sufficient to promote or facilitate the reflection of UV light. In aspects of this embodiment, a composition disclosed herein comprises a surfactant metal complex in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant metal complex in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant metal complex in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

A composition comprising one or more active agents may further include one or more photostabilizing agents. Some active agents are photosensitive and are susceptible to photochemically-initiated degradation reactions, e.g., such as a sunscreen active agent. A photostabilizing agent stabilizes against light-induced degradation and help prevent and active agent disclosed herein from losing its effectiveness or integrity.

One type of photostabilizing agent helps stabilize and active agent disclosed herein structurally and geometrically through electrostatic and van der Waals interactions, which insulate the active agent from being altered during the chemical reaction. Another type of photostabilizing agent protects an active agent disclosed herein by dissipating the energy from UV radiation more quickly, thus reducing or even eliminating the possibility of a chemical reaction. This process is called energy transfer, and it can take place when an active agent disclosed herein and photostabilizing agent exchange electrons.

A photostabilizing agent enables the use of less of certain active agents, for example, sunscreen active agents, which increases the safety of a composition disclosed herein by reducing the amount of the active agent is used, thereby reducing the amount of the active agent that can be absorbed into the body and systemically distributed. In addition, reducing the amount of the active agent also reduces the overall cost of making a composition disclosed herein. Non-limiting examples of a photostabilizing agent include 4-methylbenzylidene camphor (MBC), an alpha olefin copolymer, Bemotrizinol (BTZ), Galangal extract, ethylhexyl methoxycrylene (SOLASTAY® S1), a hindered amine light stabilizer [HALS, 2,2,6,6-tetramethyl piperidine-based compounds including TINUVIN® compounds (BASF), CHIMASSORB® compounds (BASF) and LA compounds (Amfine)], hexylresorcinol, Polyester-25 (a bis-Methoxycrylene/octyldodecyl adipic acid/methylpropanediol copolymer)(SOLASTAY® P1), octasalicyalte (octasalate), trimethoxybenzylidene pentanedione (SYNOXYL® HSS, Sytheon, Ltd.), polyester-8. Photostabilizing agents useful in a composition disclosed herein are also described in, e.g., U.S. Pat. No. 5,801,244 and U.S. Patent Publications 2009/0074684 and 2013/0059924, each of which is incorporated herein by reference in its entirety.

A composition comprising one or more active agents may further include one or more other additional agents. Generally, an additional agents disclosed herein provides a benefit different than or complementary to the one or more active agents, and/or provides a minimally similar benefit.

An additional agent disclosed herein includes, without limitation, a sunscreen agent, an analgesic agent, an aesthetic agent, an anti-acne agent, an anti-allergenic agent, an anti-cellulite agent, an anti-inflammatory agent, an antioxidant, an anti-pruritic agent, an anti-skin aging agent, an anti-skin wrinkling agent, an anti-microbial agent (e.g., antifungals, antibacterials, and antiparasitics), an anti-viral agent, a jellyfish repellent agent, a chelating agent, a deodorant, a dye, an essential oil, a hair growth promoter, a hair growth inhibitor, a hair bleaching agent, an anti-lice agent, an arachnid/insect repellent, a lipid, a medicinal agent (e.g., a biologic, a pharmaceutically active ingredient), a moisturizing agent, a pest repellent, a preservative, a silicone containing compound, a liquid hydrocarbon, a fragrance, a camouflage agent, a colorant, soothing agent (e.g. a cooling agent or a heating agent), skin whitening agent (e.g., a skin bleaching agent and a skin lightening agent), a skin nourishing agent, a structuring agent, a sunscreen agent, a sunless tanning agent, a thickening agent, a vitamin, (e.g., skin rash, skin disease and dermatitis medications) or other molecule useful in protecting, moisturizing or otherwise enhancing the health and appearance of a skin surface or hair.

An aesthetic agent includes, without limitation, benzalkonium chloride, butamben picrate, benzocaine, bupivacaine, calamine, chloroprocaine, cocaine, dibucaine, dyclonine, etidocaine, hexylcaine, ketamine, lidocaine, mepivacaine, menthol, procaine, pramoxine, prilocaine, phenol, pramoxine, tetracaine, xylocalne, and pharmaceutically acceptable salts thereof.

An analgesic agent includes, without limitation, dyclonine hydrochloride, *aloe vera*, fentanyl, capsaicin, and the like.

An anti-acne actives include, without limitation, 5,7-dichloro-8-hydroxyquinoline, adapalene, azaleic acid, benzoyl peroxide, clindamycin, dapsone, erythromycin, long chain dicarboxylic acids, hydrocortisone, resorcinol, resorcinol acetate, salicylic acid, sulphur, tretinoin, urea, zinc, various natural agents such as those derived from green tree, and more. Other non-limiting examples of suitable anti-acne actives for use herein are described in U.S. Pat. No. 5,607,980, which is hereby incorporated by reference in its entirety.

An anti-allergenic agent includes, without limitation, antihistamines. In a further embodiment, antihistamines are, without limitation, $H_1$ or $H_2$ antagonists or other types of histamine release inhibitors. In an additional embodiment, $H_1$ antagonists are sedating or non-sedating, including, without limitation, diphenhydramine (Benadryl), chlorpheniramine, tripelennamine, promethazine, clemastine, doxylamine, benadryl and more. In a further embodiment, $H_1$-non-sedating antihistamines include, without limitation, astemizole, terfenadine, loratadine etc. Examples of $H_2$ antagonists include cimetidine, famotidine, nizatidine, and ranitidine. In an additional embodiment, histamine-release-inhibitors include, without limitation, cromolyn.

An anticellulite agent includes, without limitation, isobutylmethylxanthine, caffeine, theophylline, theobromine, aminophylline, yohimbine, and mixtures thereof. In an embodiment, examples of actives suitable for treating hair loss include, without limitation, potassium channel openers or peripheral vasodilators such as minoxidil, diazoxide, and compounds such as N*-cyano-N-(tert-pentyl)-N'-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin EI and prostaglandin F2-alpha; fatty acids, such as oleic acid; diuretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal anti-inflammatory agents such as benoxaprofen; retinoids such as tretinoin; cytokines, such as IL-6, IL-1 alpha, and IL-1 beta; cell adhesion molecules such as ICAM; glucocorticoids such as betamethasone; botanical extracts such as *aloe*, clove, *ginseng*, rehmannia, swertia, sweet orange, zanthoxylum, *Serenoa repens* (*saw palmetto*), *Hypoxis rooperi*, stinging nettle, pumpkin seeds, and rye pollen; other botanical extracts including sandlewood, red beet root, *chrysanthemum*, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cycloheximide; acetazolamide; benoxaprofen; cortisone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof. Preferred hair loss treatment agents include minoxidil, 6-(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

An anti-inflammatory agent includes, without limitation, steroidal, non-steroidal, and other compounds. In a further embodiment, steroidal anti-inflammatory agents include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluocinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortolone, clescinolone, dichlorisone, diflupredmate, fluclorinide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. In an additional embodiment, a steroidal anti-inflammatory for use is hydrocortisone.

A nonsteroidal anti-inflammatory agent includes, without limitation, oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acemetacin, fentiazac, zomepirac, clidanac, oxepinac, felbinac, ketorolac); fenamates (e.g., mefenamic, meclofenamic, flufenamic, niflumic, tolfenamic acids); propionic acid derivatives (e,g., ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (Astrazeneca and NicOx), Celecoxib (Pharmacia Corp.) (4-[5-(4-methylphenyl)-3-(trifluoromethyl)-1H-pyrazol-1-yl] benzenesulfonamide), Meloxicam (Boehringer Ingelheim Pharmaceuticals) (4-hydroxy-2-methyl-N-(5-methyl-2-thiazolyl)-2H-1,2GW-406381 (Glaxosmithkline), Etoricoxib (Merck & Co.), Rofecoxib (MERCK & Co.) (4-[4-(methylsulfonyl) phenyl]-3-phenyl-2(5H)-furanone), Lumiracoxib (Novartis Pharma AG), Valdecoxib (Pharmacia Corp.) (4-(5-methyl-3-phenyl-4-isox-azolyl) benzenesulfonamide), and Etodolac (Wyeth Ayerst Laboratories) ((±) 1,8-diethyl-1,3,4,9-tetrahydropyrano-[3,4-b]acid).

An anti-inflammatory agent also includes, without limitation, candelilla wax, bisabolol (e.g., alpha bisabolol), *aloe vera*, plant sterols (e.g., *phytosterol*), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, sea whip extract, anise oil, garlic oil, ginger extract, vasoconstrictors such as phenylephrine hydrochloride, compounds of the Licorice (the plant *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific non-limiting examples of the foregoing include oil soluble licorice extract, the glycyrrhizic and glycyrrhetic acids themselves, mono ammonium glycyrrhizinate, monopotassium glycyrrhizinate, dipotassium glycyrrhizinate, 1-beta-glycyrrhetic acid, stearyl glycyrrhetinate, 3-stearyloxy-glycyrrhetinic acid, disodium 3-succinyloxy-beta-glycyrrhetinate, and combinations thereof.

An anti-microbial agent includes, without limitation, antifungal, antibacterial, and antiseptic compounds. Antifungal compounds include, but are not limited to, imidazole antifungals. Specific antifungals include, without limitation, butoconazole nitrate, miconazole, econazole, ketoconazole, oxiconazole, haloprogin, clotrimazole, and butenafine HCl, naftifine, terbinafine, ciclopirox, and tolnaftate. Antibacterials include, without limitation, an aminoglycoside, a tetracycline, a glycylcycline, a fluorocycline, an oxazolidinone, a peptidyl transferase (like an amphenicol and a pleuromutilin), a macrolide, a lincosamide, a streptogramin, a steroid antibacterial, a 3-lactam (like a penicillin, a penem, a carbapenem, a cephem, a monobactam and a 3-lactamase inhibitor), an antifolates (like a dihydrofolate reductase (DHFR) inhibitor, a sulphonamide, a topoisomerase inhibitor and a quinolone), an anaerobic DNA inhibitor (like a nitroimidazole derivative, a nitrofuran derivative and a rifamycin). Antiseptics include, without limitation, an acridine compound (like ethacridine lactate, 9-Aminoacridine and euflavine), a biguanide compound, an amidine compound (like 1,8-Diazabicyco[5.4.0]Undec-7-ene (DBU), diminazene, and benzamidine, chlorhexidine, dibromopropamidine, propamidine and hexamidine), a phenol compound (like hexachlorophene, policresulen, phenol, triclosan, triclocarban, chloroxylenol, biphenylol and fenticlor), a nitrofuran compound (like nitrofurazone), an iodine compound (iodine/octylphenoxypolyglycolether, povidone-iodine, and diiodohydroxypropane), a quinoline compound (like dequalinium, chloroquinaldol, qxyquinoline and clioquinol), a quaternary ammonium compound (like benzalkonium, benzethonium chloride, betrimonium, cetylpyridinium, cetrimide, benzoxonium chloride and didecyldimethylammonium chloride), a mercurial compound (like mercuric amidochloride, phenylmercuric borate, mercuric chloride, merbromin, thiomersal, mercuric iodide), a silver compound (like silver nitrate), an alcohol (like propanol, isopropanol, ethanol and other antiseptics like potassium permanganate, sodium hypochlorite, hydrogen peroxide, eosin, tosylchloramide and octenidine dihydrochloride.

Other antibacterial and antiseptic compounds include, without limitation, butoconazole phenol-TEA complex, mupirocin, triclosan, chlorocresol, chlorbutol, iodine, clindamycin, CAE (Anjinomoto Co., Inc., containing DL-pyrrolidone carboxylic acid salt of L-Cocoyl Arginine Ethyl Ester), povidone-iodine, polyhexanide, polyhexamethylene biguanide, polymyxin b sulfate-bacitracin, zinc-neomycin sulfate-hydrocortisone, chloramphenicol, methylbenzethonium chloride, manuka honey and erythromycin and antiseptics (e.g., benzalkonium chloride, benzethonium chloride, chlorhexidine gluconate, mafenide acetate, nitrofurazone, nitromersol), antimicrobial deodorant compounds, antiparasitics, including, without limitation, lindane and the like may be included in a composition disclosed herein.

In a further embodiment, antimicrobial with antifungal actives include, without limitation, 3-lactam drugs, quinolone drugs, 2,4,4'-trichloro-2'-hydroxy diphenyl ether, 3,4,4'-trichlorocarbanilide, amantadine, amantadine hydrochloride, amantadine sulfate, amikacin, amikacin sulfate, benzoic acid, butenafine, capreomycin, capreomycin sulfate, chlorhexidine, chlorhexidine gluconate, chlorhexidine hydrochloride, chlortetracycline, chlortetracycline hydrochloride, ciclopirox, ciprofloxacin, clindamycin hydrochloride, clotrimazole, doxycycline, doxycycline hydrochloride, econazole, efinaconazole, erythromycin, erythromycin estolate, erythromycin stearate, ethambutol, ethambutol hydrochloride, gentamicin, gentamicin sulfate, hexamidine isethionate, kanamycin, kanamycin sulfate, ketoconazole, lincomycin, lincomycin hydrochloride, luliconazole, methacycline, methacycline hydrochloride, methenamine, methenamine hippurate, methenamine mandelate, metronidazole, metronidazole hydrochloride, miconazole, miconazole hydrochloride, minocycline, minocycline hydrochloride, naftifine, neomycin, neomycin sulfate, netilmicin, netilmicin sulfate, norfloxacin, nystatin, octopirox, oxiconazole, oxytetracycline, parachlorometa xylenol, paromomycin, paromomycin sulfate, phenoxyethanol, phenoxy propanol, phenoxyisopropanol, pentamidine, pentamidine hydrochloride, paromomycin, salicylic acid, sertaconazole, streptomycin, streptomycin sulfate, sulconazole, tavaborole, terbinafine, tetracycline, tetracycline hydrochloride, tobramycin, tobramycin sulfate, tolnaftate, undecylenic acid, zinc oxytetracycline hydrochloride and zinc pyrithione.

An antioxidant includes, without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, vitamin E, coenzyme Q-10, ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, tocotrienols and their esters, and 6-hydroxy-2,5,7,8-tetramethylchroman-2-carboxylic acid (commercially available under the tradename TROLOX). Other suitable antioxidants include uric acid and its salts and alkyl esters, sorbic acid and its salts, lipoic acid, amines (e.g., N,N-diethylhydroxylamine, amino-guanidine), sulfhydryl compounds (e.g., glutathione, N-acetyl cysteine), dihydroxy fumaric acid and its salts, lysine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts, and a cascading antioxidant, such as, e.g., EMBLICA (EMD Chemicals) and synovia.

An anti-pruritic agent includes, without limitation, alclometasone dipropionate, betamethasone valerate, and isopropyl myristate MSD.

An anti-skin aging agent or anti-wrinkling agent includes, without limitation, a variety of agents, often in combination, that prevent or treat wrinkling through a variety of actions, including, without limitation, cosmetic products that contain hydroxy acids, retinol, retinoic, retinol palmitate, a derivative of vitamin A, (or its stronger, prescribed version Retin-A and Renova), bicyclic aromatic compounds with retinoid-type activity, including, without limitation, those described in EP 679 630. An anti-skin aging agent or anti-wrinkling agent includes, without limitation, bicyclic aromatic compounds, compounds which have retinoid-type activity, free-radical scavengers, a hydroxy acid, a keto acid or derivatives thereof. A "free-radical scavenger" includes, without limitation, α-tocopherol, superoxide dismutase, ubiquinol or certain metal-chelating agents. A hydroxy acid includes, without limitation, α-hydroxy acids such as lactic acid and glycolic acid or β-hydroxy acids such as salicylic acid and salicylic acid derivatives such as the octanoyl derivative; other hydroxy acids and keto acids include, without limitation, malic, citric, mandelic, tartaric or glyceric acids or the salts, amides or esters thereof. An anti-wrinkling agent and anti-skin aging agent include, without limitation, sulfur-containing D and L amino acids and their derivatives and salts, particularly the N-acetyl derivatives, a preferred example of which is N-acetyl-L-cysteine; thiols, e.g. ethane thiol; fat-soluble vitamins, ascorbyl palmitate, ceramides, pseudoceramides (e.g., pseudoceramides described in U.S. Pat. Nos. 5,198,210; 4,778,823; 4,985,547; 5,175,321, each of which is hereby incorporated by reference in its entirety), phospholipids (e.g., distearoyl lecithin phospholipid), fatty acids, fatty alcohols, cholesterol, plant sterols, phytic acid, lipoic acid; lysophosphatidic acid, and skin peel agents (e.g., phenol and the like), and mixtures thereof. A fatty acid and/or fatty acid alcohol include, without limitation, straight or branched alkyl chains containing 12-20 carbon atoms and linoleic acid. In a further embodiment, anti-wrinkle actives include, without limitation, those described in U.S. Pat. No. 6,217,888, which description is incorporated herein by reference.

An anti-viral agents includes, without limitation, acyclovir, peniciclovir, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in copending U.S. patent application Ser. No. 09/421,084 (Beerse et al.); Ser. No. 09/421,131 (Biedermann et al.); Ser. No. 09/420,646 (Morgan et al.); and Ser. No. 09/421,179 (Page et al.), which were each filed on Oct. 19, 1999.

In an embodiment, quencher actives are used for singlet and triplet excited electron stabilization caused from photons of energy and to reduce or eliminate degradation. In an embodiment, quencher actives include, without limitation, electron receptors, including, without limitation, polycrylene. In an embodiment, an infrared reflective coating comprises an agent that reflects infrared radiation, for instance, without limitation, at a wavelength between about 0.74 μm to about 300 μn. In a further embodiment, an infrared reflective coating includes, without limitation, coatings which produce different amounts of gloss and reflection. In a further embodiment, a composition with an infrared reflective coating is used by a soldier, police, national guard, governmental agent, including, without limitation, an individual working for the Federal Bureau of Investigation, Alcohol, and Tobacco & Firearms, Secret Service, Central Intelligence Agency, Department of Justice or any other governmental agent, whether located in the United States or outside the United States or other individuals who requires an infrared reflective coating.

A deodorant includes, without limitation, aluminium bromohydrate, potassium alum, sodium aluminium chlorohydroxy lactate, aluminium sulfate, aluminium chlorohydrate, aluminium-zirconium tetrachlorohydrate, an aluminium-zirconium polychlorohydrate complexed with glycine, aluminium-zirconium trichlorohydrate, aluminium-zirconium octachlorohydrate, aluminium sesquichlorohydrate, aluminium sesquichlorohydrex PG, aluminium chlorohydrex PEG, aluminium zirconium octachlorohydrex glycine complex, aluminium zirconium pentachlorohydrex glycine complex, aluminium zirconium tetrachlorohydrex glycine complex, aluminium zirconium trichlorohydrex glycine complex, aluminium chlorohydrex PG, zirconium chlorohydrate, aluminium dichlorohydrate, aluminium dichlorohydrex PEG, aluminium dichlorohydrex PG, aluminium sesquichlorohydrex PG, aluminium chloride, aluminium chloride hexahydrate, aluminium zirconium pentachlorohydrate, methylbenzethonium chloride, chlorophyllin copper complex and numerous other useful antiperspirant compounds listed in the CTFA Handbook at p. 56, incorporated herein by reference, and mixtures thereof.

A deodorant also includes, without limitation, astringent salts and bioactive compounds. An astringent salt includes, without limitation, organic and inorganic salts of aluminium, zirconium, zinc, and mixtures thereof. Anions of the astringent salt include, without limitation, sulfate, chloride, chlorohydroxide, alum, formate, lactate, benzyl sulfonate or phenyl sulfonate. An antiperspirant astringent salt includes, without limitation, aluminium halides, aluminium hydroxyhalides, zirconyl oxyhalides, zirconyl hydroxyhalides, and mixtures thereof. An aluminium salt includes, without limitation, aluminium chloride and the aluminium hydroxyhalides having the general formula $Al_2(OH)_xQ_y XH_2O$, wherein Q is chlorine, bromine or iodine; x is about 2 to about 5; x+y is about 6, wherein x and y are not necessarily integers; and X is about 1 to about 6. A zirconium compound includes, without limitation, zirconium oxy salts and zirconium hydroxy salts, also referred to as zirconyl salts and zirconyl hydroxy salts, and represented by the general empirical formula $ZrO(OH)_2 2\text{-}nz\, L$, wherein z varies from about 0.9 to about 2 and is not necessarily an integer; n is the valence of L; 2-nz is greater than or equal to 0; and L is selected, without limitation, from the group consisting of halides, nitrate, sulfamate, sulfate, and mixtures thereof.

A deodorant also includes, without limitation, a bacteriostatic quaternary ammonium compound, such as, e.g., cetyl trimethyl ammonium bromide, cetyl pyridinium chloride, benzethonium chloride, diisobutylbenzoxyethoxyethyldimethylbenzyl ammonium chloride, sodium N-lauryl sarcosine, sodium N-polymethyl sarcosine, lauroyl sarcosine, N-myristoyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetraalkylammonium carbonates and bicarbonates.

A hair bleaching agent includes, without limitation, a perborate salt or a persulfate salt. A hair growth inhibiting includes, without limitation, serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethasone; antihyperlipidaemic drugs, such as triparanol and clofibrate; thallium; mercury; albendazole; allopurinol; amiodarone; amphetamines; androgens;

bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; imipramine; immunoglobulins; indandiones; indomethacin; itraconazole; levodopa; maprotiline; methysergide; metoprolol; metyrapone; nadolol; nicotinic acid; potassium thiocyanate; propranolol; pyridostigmine; salicylates; sulfasalazine; terfenadine; thiamphenicol; thiouracils; trimethadione; triparanol; valproic acid; and mixtures thereof. Preferred hair growth inhibitory agents include serine proteases, retinol, isotretinoin, betamethoisone, alpha-tocophenol and derivatives thereof, or mixtures thereof.

An anti-lice agent includes, without limitation, include organochlorines, such as, e.g., lindane, organophosphates, such as, e.g., malathion, carbamates, such as, e.g., carbaryl, pyrethrins, such as, e.g., pyrethrum, pyrethroids, such as, e.g., permethrin, phenothrin, bioallethrin, and spinosad, such as, e.g., spinosyn A and spinosyn D, bactrim, benzyl alcohol, crotamiton, dimethicone and ivermectin.

A fragrance includes, without limitation, alcohols (e.g., furaneol, 1-hexanol, cis-3-hexen-1-ol, menthol, or the like); aldehydes (e.g., acetaldehyde, hexanal, cis-3-hexenal, furfural, or the like); esters (e.g., fructone, hexyl acetate, ethyl methylphenylglycidate, methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin, black, cajuput oil, caraway, carrot seed, coriander, cypress, dill, fennel, helichyrsum, lavanding lemon verena, bee balm, niaouli, palmarosa, petitgrain, *tagetes*, vetiver, or the like); ketones (e.g., dihydrojasmone, oct-1-en-3-one, 2-acetyl-1-pyrroline, 6-acetyl-2,3,4,5-tetrahydropyridine, or the like); lactones (e.g., γ-decalactone, γ-nonalactone, δ-octalactone, massoia lactone, sotolon, or the like); thiols (e.g., ethanethiol, grapefruit mercaptan, methanethiol, 2-methyl-2-propanethiol, or the like); linear terpenes (e.g., myrcene, geraniol, nerol, citral, lemonal, geranial, neral, citronellal, citronellol, linalool, nerolidol, or the like); cyclic terpenes (e.g., limonene, camphor, terpineol, ionone, thujuon, or the like); aromatic species (e.g., benzaldehyde, eugenol, cinnamaldehyde, ethyl maltol, vanillin, anisole, anethole, estragole, thymol, or the like); amines (e.g., thiethylamine, trimethylamine, cadaverine, pyridine, indole, skatole, or the like); or the like, or a combination comprising at least one of the foregoing fragrant molecules.

Further examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, alpha-n-amylcinammic aldehyde, alpha-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methyl-pentyl)-3-cyclohexene carbaldehyde, 4-(4-methyl-3-pente-nyl)-3-cyclohexene carbaldehyde, 4-acetoxy-3-pentyltetrahydropyran, methyl-dihydrojasmonate, 2-n-heptylcyclopentanone, 3-methyl-2-pentylcyclopentanone, n-decanal, 9-decenol-I, phenoxyethyl isobutyrate, phenylacetaldehyde dimethyl acetal, phenylacetaldehyde diethyl acetal, geranonitrile, citronellonitrile, cedryl acetate, 3-iso-camphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylioniones, irones, cis-3-hexenol and esters thereof, indane musk, tetralin musk, isochroman musk, macrocyclic ketones, macrolactone musk, ethylene brassylate, aromatic nitro-musk. Exemplary fragrant molecules include bergamot oil, coriander oil, dimethyl heptanol, dimethyl benzyl carbinyl acetate, geranyl acetate, citronellyl acetate, rose synthetic, *geranium* bourbon, hedione, iso eugenol, methyl eugenol styrallyl acetate, stemone, rose oxide laevo, aldehyde C-II undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

A colorant, includes, without limitation, an agent used to color skin, nail, hair or other surface. A colorant, includes, without limitation, aluminum powder, annatto, bismuth citrate, bismuth oxychloride, bronze powder, caramel, carmine, β-carotene, chromium hydroxide green, chromium oxide green, copper powder, dihydroxyacetone, disodium EDTA-copper, ferric ammonium, ferrocyanide, ferric ferrocyanide, guaiazulene, guanine, henna, iron oxide, lead acetate, luminescent zinc sulfide, manganese violet, mica, potassium sodium copper chlorophyllin (chlorophyllin-copper complex), pyrophillite, silver, titanium dioxide, ultramarine, zinc oxide, D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10 and D&C Yellow No. 11.

A camouflage agent, includes, without limitation, a UV reflector, a UV absorber, an infrared (IR) reflector and an IR absorber. A UV reflector reflects wavelengths from about 10 nm to about 400 nm.

An UV absorber absorbs wavelengths from about 10 nm to about 400 nm. Non-limiting examples of a UV absorber include an acrylate dye, a benzotriazole dye, a benzophenone dye and a phosphite dye. Specific UV absorber compounds include, without limitation, 2,4-dihydroxy benzophenone, 2,4-dihydroxybenzophenone, 2-hydroxy-4-methoxybenzophenone, 2,2'-dihydroxy-4,4'-dimethoxybenzophenone, 2,2',4,4'-tetrahydroxybenzophenone, 2-hydroxy-4-dodecyloxybenzophenone, 2-hydroxy-4-octyloxybenzophenone, 2-hydroxy-4-methoxybenzophenone, ethyl-2-cyano-3,3-diphenylacrylate, 2-ethylhexyl-2-cyano-3,3-diphenylacrylate, 2-ethylhexyl-2-cyano-3,3-diphenylacrylate, 2-hydroxy-4-methyoxy-benzophenone-5-sulfonic acid, 2,2'-dihydroxy-4,4'dimethoxy-5-sulfobenzophenone, 2-(2-hydroxy-5-methylphenyl)-2H-benzotriazole, 2-(2-hydroxy-5-carboxy-phenyl)-2H-benzotriazole, N-(p-ethoxycarbonylphenyl)-N'-ethyl-N'-phenylformamidine, poly-phenolic phosphite and tris (2,4-di-t-butylphenyl) phosphite.

An IR reflector reflects wavelengths from about 700 nm to about 1500 nm. Non-limiting examples of an IR reflector include a metal oxide. Specific IR reflector compounds include, without limitation, an iron oxide, a titanium dioxide and a zinc oxide.

An IR absorber absorbs wavelengths from about 700 nm to about 1500 nm. Non-limiting examples of an IR absorber include an azo dye, a croconium dye, a diphenylmethane dye, a heptamethinecyanine dye, a metal complex dye, a naphthalocyanine dye, a photochromic dye, a phthalocyanine dye, a polymethine dye, a pyrylium dye, a quinone dye, a squarylium dye and a triphenylmethane dye. A metal complex dye includes, without limitation, a dithiolene metal complex, an indoanilinetype metal complex and a phenylenediamine metal complex. Specific IR absorber compounds include, without limitation, 2-[2-[2-Chloro-3-[(1,3-dihydro-1,3,3-trimethyl-2H-indol-2-ylidene)ethylidene]-1-cycloxen-1-yl]-ethenyl]-1,3,3-trimethyl-1H indolium iodide, 2-[2-[2-Chloro-3-[(1,3-dihydro-1,3,3-trimethyl-2H-indol-2-ylidene)ethylidene]-1-cycloxen-1-yl]-ethenyl]-1,3,3-trimethyl-1H indolium perchlorate, 2-[2-[2-Chloro-3-[(1,3-dihydro-3,3-dimethyl-1-propyl-2H-indol-2-ylidene)ethylidene]-1-cycloxen-1-yl]-ethenyl]-3,3-dimethy-1-propyl-1H-indolium iodide, 2-[2-[2-Chloro-3-[(1,3-dihydro-3,3-dimethyl-1-propyl-2H-indol-2-ylidene)ethylidene]-1-cycloxen-1-yl]-ethenyl]-3,3-dimethy-1-propyl-1H-indolium perchlorate, 2-[2-[2-Chloro-3-[(1,3-dihydro-3,3-dimethyl-1-(2-hydroxyethyl)-2H-indol-2-ylidene)ethylidene]-1-cycloxen-1-yl]-ethenyl]-3,3-dimethy-1-(2-hydroxyethyl)-1H-indolium perchlorate, 2-[2-[3-[2-(1,3-Dihydro-1,3,3-trimethyl-2H-indol-2-ylidene)-ethylidene]-2-(1-phenyl-1H-tetrazol-5-ylsulfanyl)-1-cyclohexen-1-yl]-ethenyl]-1,3,3-trimethyl-3H-indolium chloride, 2-[2-[2-(4-Methylbenzeneoxy)-3-[2-(1,3-dihydro-1,1,3-trimethyl-2H-benz[e]indol-2-ylidene)ethylidene]-1-cyclohexen-1-yl]-ethenyl]-1,1,3-trimethyl-1H-benz[e]indolium 4-methylbenzenesulfonate, 2-[2-[2-chloro-3-[2-(1,3-dihydro-3,3-dimethyl-1-ethyl-2H-benz[e]indol-2-ylidene)ethylidene]-1-cyclohexen-1-yl]-ethenyl]-3,3-dimethyl-1-ethyl-1H-benz[e]indolium iodide, 2-[2-[2-chloro-3-[2-(1,3-dihydro-1,1,3-trimethyl-2H-benz[e]indol-2-ylidene)ethylidene]-1-cyclohexen-1-yl]-ethenyl]-1,1,3-trimethyl-1H-benz[e]indolium 4-methylbenzenesulfonate, 1,4-Benzenediamine,N,N-bis[4-(dibutylamino)phenyl]-N',N'-diethyl-, radical ion (2+), bis [hexafluoroantimonate (1-)], 4,4',4"-tris(N,N-phenyl-3-methylphenylamino)triphenylammonium hexafluoroantimonate, 2-[2-[2-Chloro-3-[2-(1,3-dihydro-3,3-dimethyl-1-(4-sulfobutyl)-2H-indol-2-ylidene)-ethylidene]-1-cyclohexen-1-yl]-ethenyl]-3,3-dimethyl-1-(4-sulfobutyl)-1H-indolium, 2-[7-(1,3-Dihydro-3,3-dimethy-1-(4-sulfobutyl)I-2H-benz[e]indol-2-ylidene)-1,3,5-heptatrienyl]-3,3-dimethyl-1-(4-sulfobutyl)-1H-benz[e]indolium, 2-[2-[2-(4-aminobenzenethiol)-3-[(1,3-dihydro-3,3-dimethyl-1-(4-sulfobutyl)-2H-indol-2-ylidene)-ethylidene]-1-cycloxen-1-yl]-ethynyl]-3,3-dimethyl-1-(4-sulfobutyl)-3H-indolium, 2-[2-[2-Chloro-3-[2-(3-(4-sulfobutyl)-3H-benzothiazol-2-ylidene)-ethylidene]-1-cyclohexen-1-yl]-ethenyl]3-(4-sulfobutyl)benzothiazolium, 2-[2-[2-Chloro-3-[2-(1,3-dihydro-3,3-dimethyl-1-(4-sulfobutyl)-2H-benz[e]-indol-2-ylidene)-ethylidene]-1-cyclohexen-1-yl]-ethenyl]-3,3-dimethyl-1-(4-sulfobutyl)-1H-benz[e]indolium, 2-2-[2-[2-(4-aminothiophenyl)-3-[[1,3-dihydro-1,1-dimethyl-3-(4-sulfobutyl)-2H-benz[e]-indol-2-ylidene]ethylidene]-1-cyclohexen-1-yl]ethenyl]-1,1-dimethyl-3-(4-sulfonyl)-, tetrabutylammonium bis(3,6-dichloro-1,2-benzene-dithiolato)nickelate, tetrabutylammonium bis(3,4,6-trichloro-1,2-benzene-dithiolato)nickelate, tetrabutylammonium bis(4-methyl-1,2-benzenedithiolato) nickelate and Bis(4,4'-dimethoxydithiobenzyl) nickel. Other IR absorbers are described in Matsuoka, INFRARED ABSORBING DYES, pp. 220 (Springer Science & Business Media, 1990), which is hereby incorporated by reference in its entirety.

A soothing agent can be a cooling agent or a heating agent. Soothing agents include, without limitation, herb extracts, such as, e.g., *aloe vera*, alpha bisabolol, D-panthenol, allantoin, *hamamelis*, chamomile, yarrow; *calendula*, comfrey, witch hazel and other astringents, sea weed, and oat extracts; oils, selected from the group consisting of: almond oil, avocado oil, and comfrey; and essential oils, selected from the group consisting of: cardamone, *eucalyptus, Mentha piperita* (peppermint), hyssop, and rosemary; waxy or unctuous substances selected from the group consisting of: lanolin or petroleum jelly, minerals, selected from the group consisting of: zinc oxide, calamine and selenium; vitamins, selected from the group consisting of: tocopheryl acetate (vitamin E), and pharmaceutical agents selected from the group consisting of: analgesics, anesthetics, anti-inflammatory agents, and anti-histamines, and muscle relaxants; menthol, camphor, eugenol, eucalyptol, safrole, methyl salicylate, menthyl lactate, menthyl ethoxyacetate, menthone glycerinacetal, 3-l-menthoxypropane-1,2-diol, ethyl l-menthyl carbonate, (1S,3S,4R)-p-menth-8-en-3-ol, menthyl pyrrolidone carboxylate, N-substituted-p-menthane-3-carboxamides *hamamelis* extract and ginger oil.

A cooling agent includes, without limitation, menthol; an isomer of menthol, a menthol derivative (e.g., menthol ethylene glycol carbonate, which is now known as Frescolat® type MGC, menthol Propylene Glycol Carbonate (Frescolat® type MPC), menthyl lactate (Frescolat ML®) and Menthone Glycerin Acetal (Frescolat MGA®) and 3-(I-Menthoxy)-1,2-propanediol); 4-Methyl-3-(1-pyrrolidinyl)-2[5H]-furanone; WS-23, Icilin, Icilin Unilever Analog, 5-methyl-4-(1-pyrrolidinyl)-3-[2H]-furanone; 4,5-dimethyl-3-(1-pyrrolidinyl)-2[5H]-furanone; isopulegol, 3-(1-menthoxy)propane-1,2-diol, 3-(1-menthoxy)-2-methylpropane-1,2-diol, p-menthane-2,3-diol, p-menthane-3,8-diol (Coolact® 38D), 6-isopropyl-9-methyl-1,4-dioxas-piro[4,5]decane-2-methanol, menthyl succinate and its alkaline earth metal salts, trimethylcyclohexanol, N-ethyl-2-isopropyl-5-methylcyclohexanecarb-oxamide, Japanese mint (*Mentha arvensis*) oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, spearmint oil and coolact 38D.

A heating agent includes, without limitation, polyhydric alcohols, *capsicum* (red pepper) powder, a *capsicum* tincture, *capsicum* extract, capsaicin, homocapsaicin, homodihydrocapsaicin, nonanoyl vanillyl amide, nonanoic acid vanillyl ether, vanillyl alcohol alkyl ether derivatives, such as vanillyl ethyl ether, vanillyl butyl ether, vanillyl pentyl ether, and vanillyl hexyl ether, isovanillyl alcohol alkyl ethers, ethylvanillyl alcohol alkyl ethers, veratryl alcohol derivatives, substituted benzyl alcohol derivatives, substituted benzyl alcohol alkyl ethers, vanillin propylene glycol acetal, ethylvanillin propylene glycol acetal, ginger extract, ginger oil, gingeol, and gingeron.

A jellyfish repellent agent is used for repelling or preventing stings from members of the phylum Cnidaria (e.g., jellyfish, sea anemone, and coral), the phylum Myxozoa, or the like). A jellyfish repellent agent includes, without limitation, one or both of an antihistamine agent and one or more cations. An antihistamine agent includes, without limitation, diphenhydramine, cimetidine or tripelennamine or other histamine binding inhibitors. In aspects of this embodiment, a jellyfish repellent agent is present in a concentration from about 0.0005% to about 2.0% or from about 0.001% to about 0.2%, or similar effective amount). A cation includes, without limitation, metal cations and alkali cations such as, e.g., $Ca^{++}$, $K^+$, $Na^+$, $Mn^{++}$, $Co^{++}$, $Mg^{++}$, or $Fe^{++}$, or other substance which is capable of supplying positively charged ions. In aspects of this embodiment, a cation is present in a concentration of from about 5 mM to about 1M, or about 25 mM to about 500 mM, or from about 50 mM to about 200 mM.

A skin whitening agent includes, without limitation, skin lightening agent and skin bleaching agent. A skin whitening agent include, without limitation, alpha hydroxyl acids ("AHA's"), arbutin, *cinnamomum subavenium*, EMBLICA (also an antioxidant), hydroquinone, kojic acid, azelaic acid, ascorbic acid and derivatives thereof (e.g., magnesium ascorbyl phosphate or sodium ascorbyl phosphate), niacinamide, a licorice extract (e.g., glabridin), a mulberry extracts and a placental extract. A skin whitening agent can include a depigmentation agent including, without limitation, monobenzone or mequinol. Additional skin whitening agents are also described in WO 1995/34280, WO 1995/07432, and WO 1995/23780.

A sunless tanning agent includes, without limitation, dihydroxyacetone (DHA); glyceryl aldehyde; tyrosine and tyrosine derivatives such as, e.g., malyltyrosine, tyrosine glucosinate, and ethyl tyrosine; phospho-DOPA, indoles and derivatives thereof.

A vitamin includes, without limitation, Vitamin A and derivatives thereof (including, for example, retinol), ascorbic acid (Vitamin C and derivatives), Vitamin B (e.g., riboflavin, vitamin B2), biotin, Vitamin D (all forms), Vitamin E and derivatives thereof such as tocopheryl acetate, beta-carotene, panthothenic acid and more.

A skin care agent includes, without limitation, those found in the CTFA Cosmetic Ingredient Handbook, Seventh Edition, 1997 and the Eighth Edition, 2000 and Remington's Pharmaceutical Sciences, 20th Ed., Lippincott Williams & Witkins, Baltimore, Md. (2000) (hereinafter Remington's), U.S. Pharmacopeia and National Formulary, The United States Pharmacopeia Convention, Inc., Rockville, Md. and Physician's Desk Reference, Medical Economics Co., Inc., Oradell, N.J. all of which are incorporated herein by reference.

A chelating agent is a compound that chelates or binds metallic ions, such as with a heterocyclic ring structure so that the ion is held by chemical bonds from each of the participating rings. Chelating agent includes, without limitation, ethylene diaminetetraacetic acid (EDTA), EDTA disodium, calcium disodium edetate, EDTA trisodium, EDTA tetrasodium and EDTA dipotassium.

A preservative, includes, without limitation, citric acid, tartaric acid, phosphoric acid, iminodiacetic acid, nitrilotriacetic acid, hydroxyethyleneaminodiacetic acid and ethylenediaminetetraacetic acid and salts thereof; para-hydroxybenzoates such as butyl paraben, methyl paraben and propyl paraben; imidazolines (e.g., imidiazolinylurea), triclosan, hydantoins (e.g., dimethyloldimethylhydantoin), isothiazolidinone compounds and mixtures thereof, KATHON® CG and KATHON® CGII, which contain methylchloroisothiazolinone and methylisothiazolinone (Rohm and Haas).

A sunscreen additional or active agent is an ultraviolet (UV) ray-blocking compound that absorbs, blocks and/or reflects UV radiation. A sunscreen active agent disclosed herein absorbs, blocks and/or reflects UV radiation given off by a natural source, such as, e.g., sunlight, and/or man-made source, such as, e.g., a fluorescent light bulb. In an aspect of this embodiment, a sunscreen active agent exhibits absorptive and/or reflective properties within the wavelength region of between about 290 to about 420 nm. Any sunscreen active agent known in the art or apparent to a skilled artisan may be used. A sunscreen active agent disclosed herein may be an organic molecule or inorganic molecule. In addition, a sunscreen active agent may be a UVA absorber, a UVA blocker, a UVA reflector, a UVB absorber, a UVB blocker, a UVB reflector, a broad spectrum UVA and UVB absorber, a broad spectrum UVA and UVB blocker, a broad spectrum UVA and UVB reflector, a physical blocker, a physical reflector, or any combination thereof. A UVA absorber can be a UVA I absorber and/or UVA II absorber.

Sunscreen additional or active agents commonly contain one or more of the following ingredients: 1) a chemical sunscreen active agent, typically an organic compound that absorb UV light; 2) a physical sunscreen active agent, typically an inorganic particulates that reflect, scatter, and absorb UV light; and 3) a hybrid sunscreen active agent, typically an organic particulate that absorbs UV light like an organic chemical compound, but also contain multiple chromophores that may reflect and scatter UV light like an inorganic particulate.

Organic sunscreen additional or active agents can be grouped based upon their chemical structure. Such groups include, without limitation: 1) a para-amino benzoate or derivative or salt thereof; 2) a salicylate or derivative or salt thereof; 3) a cinnamate or derivative or salt thereof; 4) a benzophenone or derivative or salt thereof; 5) an anthralinate or derivative or salt thereof; 6) dibenzoylmethane or derivative or salt thereof; 7) a camphor or derivative or salt thereof; 8) a naphtholsulfonate or derivative or salt thereof; 9) a coumarin or derivative or salt thereof; 10) a diazole or derivative or salt thereof; 11) a biphenyldisulfonate or derivative or salt thereof; 12) a hydrocarbon or derivative or salt thereof; 13) a quinolone or derivative or salt thereof; 14) a quinine salt; 15) a miscellaneous organic sunscreen active agent.

A sunscreen additional or active agent can be a UVA sunscreen active agent, a UVB sunscreen active agent, or a UVA/UVB or "broad spectrum" sunscreen active agent. A UVA sunscreen active agent exhibits absorptive, blocking and/or reflective properties within the wavelength region of between about 290 nm to about 320 nm. A UVA sunscreen active agent exhibits absorptive, blocking and/or reflective properties within the wavelength region of between about 320 nm to about 420 nm. A broad spectrum UVA/UVB sunscreen active agent exhibits absorptive, blocking and/or reflective properties within the wavelength region of between about 290 to about 420 nm. Non-limiting examples of a UVA sunscreen active agent include Avobenzone (butyl methoxydibenzoylmethane or Parsol 1789), bisdisulizole disodium (Neo Heliopan AP), diethylamino hydroxybenzoyl hexyl benzoate (Uvinul A Plus), ecamsule (Mexoryl SX) and menthyl anthranilate. Non-limiting examples of a UVB sunscreen active agent include amiloxate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), Padimate 0 (Escalol 507), phenylbenzimidazole sulfonic acid (Ensulizole), polysilicone-15 (Parsol SLX) and trolamine salicylate. Non-limiting examples of a broad spectrum UVA/UVB sunscreen active agent include bemotrizinol (Tinosorb S), benzophenones 1-12, dioxybenzone, drometrizole trisiloxane (Mexoryl XL), Iscotrizinol (Uvasorb HEB), octocrylene, oxybenzone (Eusolex 4360), sulisobenzone, bisoctrizole (Tinosorb M), titanium dioxide, and zinc oxide.

A sunscreen additional or active agent useful for a composition disclosed herein are also described in, e.g., U.S. Pat. Nos. 5,169,624; 5,543,136; 5,849,273; 5,904,917; 6,224,852; 6,217,852; and Segarin et al., chapter Vil, pages 189 of Cosmetics Science and Technology, and Final Over-the-Counter Drug Products Monograph on Sunscreens (Federal Register, 1999:64:27666 27963), each of which are incorporated herein by reference in its entirety.

A thickening agent (or gallant) is used to adjust the texture and viscosity of a composition disclosed herein. A thickening agent includes, without limitation, CARBOPOL™ resins [e.g., 934, 971, 974, 980, 981] and PEMULEN™ [TR-1 and TR-2] [both CARBOPOL™ and PEMULEN™ are registered trademarks of BF Goodrich], Noveon AA-1, ETD resins, and ULTREZ™ resins or carbomers.

A medicinal agent includes, without limitation, camphor, menthol, benzocaine, butamben picrate, dibucaine, dibucaine hydrochloride, dimethisoquin hydrochloride, dyclonine hydrochloride, lidocaine, metacresol, lidocaine hydrochloride, pramoxine hydrochloride, tetracaine, tetracaine hydrochloride, benzyl alcohol, camphorated metacresol, juniper tar, phenol, phenolate sodium, resorcinol, diphenhydramine hydrochloride, tripelennamine hydrochloride, hydrocortisone, a corticosteroid, and hydrocortisone acetate, burn relief agents, such as o-amino-p-toluenesulfonamide monoacetate; dermatitis relief agents, such as the active steroid amcinonide, diflorasone diacetate, and hydrocortisone; diaper rash relief agents, such as methylbenzethonium chloride and the like; a photochemotherapeutic like aminolevulinic acid, methyl aminolevulinic acid or methoxsalen; a herpes treatment agent, such as O-[(2-hydroxyethoxy)methyl]guanine; psoriasis, seborrhea and scabicide agents, such as shale oil and derivatives thereof, elubiol, ketoconazole, coal tar and petroleum distillates, salicylic acid, zinc pyrithione, selenium sulfide, hydrocortisone, sulfur, menthol, psoralen, pramoxine hydrochloride anthralin, and methoxsalen; steroids, such as Alclometasone, amcinonide, betamethasone, clobetasol, clocortolone, diflorasone, desonide, desoximetasone, fluocinolone, fluocinonide, flurandrenolide, fluticasone, halcinonide, halobetasol, hydrocortisone, mometasone, prednicarbate, triamcinolone, 2-(acetyloxy)-9-fluoro-1',2',3',4'-tetrahydro-11-hydroxy-pregna-1,4-dieno [16,17-b]naphthalene-3,20-dione and 21-chloro-9-fluoro-1',2',3',4'-tetrahydro-11 b-hydroxy-pregna-1,4-dieno[16z,17-b]naphthalene-3,20-dione. Other medicinal agents include, without limitation, ones for treating dermatological conditions such as psoriasis, acne, eczema, and other skin conditions due to disease, pathology, accident, as well as medicinal agents useful in the treatment of exposure to poison oak, poison ivy, poison sumac, and the like.

In an embodiment of the present composition, additional ingredients can be present include, without limitation, a fragrance, a dye, an oil, a non-polar wax, a liquid hydrocarbon and/or an antimicrobial material. A non-polar wax, includes, without limitation, ester waxes, diester waxes, hydrocarbon waxes, silicone waxes and triglyceride waxes and mixtures thereof. An antimicrobial material includes, without limitation, triclocarban, triclosan, iodophors, iodine formulations, phenolic compounds, e.g. hexachlorophene, and bisbiguanides, e.g. chlorhexidene gluconate, and the like. See, e.g. U.S. Pat. Nos. 6,827,795; 6,517,854; 6,010,817; 5,173,216; 5,719,113; 5,259,984; 5,562,912; 5,629,006; 5,728,662; 5,767,163; 5,750,579; 5,591,442; 5,650,143; 5,772,640; and 4,478,821, each of which is hereby incorporated by reference in its entirety.

In aspects of this embodiment, a composition disclosed herein may comprise, e.g., at least one, at least two, at least three, at least four, at least five, at least six, at least seven, at least eight, at least nine or at least ten additional agents. In other aspects of this embodiment, a composition disclosed herein may comprise, e.g., at most one, at most two, at most three, at most four, at most five, at most six, at most seven, at most eight, at most nine or at most ten additional agents. In yet other aspects of this embodiment, a composition disclosed herein may comprise, e.g., about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10 or about 9 to about 10 additional agents.

A composition disclosed herein comprises an additional agent in an amount sufficient to promote or facilitate the function or activity of that additional agent. The amount of additional agent can range from 0.00% to 99.9% by total weight of the composition, or any integer or range in between. In aspects of this embodiment, a composition disclosed herein comprises an additional agent in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises an additional agent in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises an additional agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In an embodiment, an agent disclosed herein can have more than one function. For example, without limitation, inorganic blockers such as Tioveil and Spectraveil (both of the Tioxide Group), can act as film-formers and have other advantageous uses. In an embodiment, a composition includes, without limitation, a wide variety of additional components selected so as to avoid any undesirable reaction with the primary components of the composition. The CTFA Cosmetic Ingredient Handbook, Seventh Edition, 1997 and the Eighth Edition, 2000 (incorporated by reference herein), provide a broad source of possible cosmetic and pharmaceutical ingredients typically used in skin care compositions. In an embodiment, additional components include, without limitation, one or more of the following: Absorbents, abrasives, anticaking agents, antifoaming agents, binders, biological additives, buffering agents, bulking agents, chelating agents/sequestrants (e.g., disodium EDTA), chemical additives, colorants, cosmetic astringents, cosmetic biocides, denaturants, drug astringents, emollients (including glycerin alovera, and Vitamins A, C, and D [hydrating agents and skin protectants]), foam boosters, fragrance components, gums, humectants/moisturizers (including urea, guanidine, glycolic acid, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof), hydrotropes, neutralizing agents, opacifying agents and pigments, pH adjusters, plasticizers, preservatives, propellants, reducing agents, skin bleaching agents, skin protectants, solubilizing agents, and suspending agents (e.g., Carbomer 1382).

A composition disclosed herein comprises a capsule disclosed herein in an amount sufficient to provide an effective amount of the one or more active agents and/or an additional agent disclosed herein. In aspects of this embodiment, a composition disclosed herein comprises a capsule disclosed herein in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises a capsule disclosed herein in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises a capsule disclosed herein in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises a capsule disclosed herein in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A composition disclosed herein comprises a cellulose derived capsule in an amount sufficient to provide an effective amount of the one or more active agents and/or an additional agent disclosed herein. In aspects of this embodiment, a composition disclosed herein comprises a cellulose derived capsule in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises a cellulose derived capsule in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises a cellulose derived capsule in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises a cellulose derived capsule in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A composition disclosed herein comprises a sol-gel capsule in an amount sufficient to provide an effective amount of the one or more active agents and/or an additional agent disclosed herein. In aspects of this embodiment, a composition disclosed herein comprises a cellulose derived capsule in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34% or at least 35% of the total weight of the composition.

In other aspects of this embodiment, a composition disclosed herein comprises a sol-gel capsule in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34% or at most 35% of the total weight of the composition.

In other aspects of this embodiment, a composition disclosed herein comprises a sol-gel capsule in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 0.5% to about 15%, about 0.5% to about 20%, about 0.5% to about 25%, about 0.5% to about 30%, about 0.5% to about 35%, about 0.5% to about 40%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 1.0% to about 25%, about 1.0% to about 30%, about 1.0% to about 35%, about 1.0% to about 40%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 2.0% to about 25%, about 2.0% to about 30%, about 2.0% to about 35%, about 2.0% to about 40%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 3.0% to about 25%, about 3.0% to about 30%, about 3.0% to about 35%, about 3.0% to about 40%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 4.0% to about 25%, about 4.0% to about 30%, about 4.0% to about 35% or about 4.0% to about 40% of the total weight of the composition.

In other aspects of this embodiment, a composition disclosed herein comprises a sol-gel capsule in an amount of, e.g., about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 5.0% to about 35%, about 5.0% to about 40%, about 8.0% to about 9.0%, about 8.0% to about 10%, about 8.0% to about 11%, about 8.0% to about 12%, about 8.0% to about 13%, about 8.0% to about 14%, about 8.0% to about 15%, about 8.0% to about 16%, about 8.0% to about 17%, about 8.0% to about 18%, about 8.0% to about 19%, about 8.0% to about 20%, about 8.0% to about 25%, about 8.0% to about 30%, about 8.0% to about 35%, about 8.0% to about 40%, about 10.0% to about 15%, about 10.0% to about 20%, about 10.0% to about 25%, about 10.0% to about 30%, about 10.0% to about 35%, about 10.0% to about 40%, about 15.0% to about 20%, about 15.0% to about 25%, about 15.0% to about 30%, about 15.0% to about 35%, about 15.0% to about 40%, about 20.0% to about 25%, about 20.0% to about 30%, about 20.0% to about 35%, about 20.0% to about 40%, about 25.0% to about 30%, about 25.0% to about 35%, about 25.0% to about 40%, about 30.0% to about 35%, about 30.0% to about 40% or about 35.0% to about 40% of the total weight of the composition.

A composition disclosed herein generally has a pH of about 4 to about 8. In aspects of this embodiment, a composition has a pH of, e.g., about 4 to about 5, about 4 to about 6, about 4 to about 7, about 4 to about 8, about 5 to about 6, about 5 to about 7, about 5 to about 8, about 6 to about 7, about 6 to about 8 or about 7 to about 8. In aspects of this embodiment, a composition has a pH of, e.g., about 6.4 to about 7.4, about 6.5 to about 7.5, about 6.6 to about 7.6, about 6.7 to about 7.7, about 6.6 to about 7.2, about 6.7 to about 7.3, about 6.8 to about 7.4, about 6.9 to about 7.5, about 7.0 to about 7.6, about 6.7 to about 7.1, about 6.8 to about 7.2, about 6.9 to about 7.3, about 7.0 to about 7.4, about 6.8 to about 7.0, about 6.9 to about 7.1 or about 7.0 to about 7.2.

A composition disclosed herein may be applied topically to a skin surface of an individual. A skin surface includes the skin of the arms, legs and torso and head, including the scalp and hair of an individual. A composition disclosed herein may be topically applied to an individual by hand or with an applicator. An applicator includes without limitation, with a sponge, a loofah, a toy, a cotton pad, a wash cloth, a specialized wash cloth, a towel, clothing, a spray bottle, an applicator bottle or any device or article, including a clothing article or applicator. A toy, includes, without limitation, a rubber squeeze toy, including, without limitation, a rubber duck, or a plastic squeeze toy. An applicator disclosed herein is preloaded or can be loaded with a composition disclosed herein. An applicator includes an applicator bottle with a roller ball, a push button, a nozzle, a turn nob or other means to apply the composition to an individual. Typically, an applicator disclosed herein provides a composition disclosed herein to an individual in metered, defined amounts. For example, metering may be accomplished by pushing down on a nozzle that is part of the applicator. An applicator may also be a squeezable bottle wherein a composition disclosed herein can be dispensed from the bottle as an individual squeezes the bottle. A composition disclosed herein may also be applied using a spray on applicator, including, without limitation, a spray bottle.

A composition disclosed herein can be, or combined with, a skin care product. Non-limiting examples of a skin care product include any conventional body wash, after shower body lotion, shampoo, conditioner, soap, gel, hand sanitizer, cream, spray, mouse, lotion, ointment, make-up product, lip balm, hair spray product, arachnid/insect repellent or medicinal product. A body wash, shampoo, after shower body lotion, conditioner, soap, gel, hand sanitizer, cream, spray, mouse, lotion, ointment, make-up product, lip balm, hair spray product, arachnid/insect repellent or medicinal product disclosed herein can be, without limitation, any body wash, after shower body lotion, shampoo, conditioner, soap, gel, hand sanitizer, cream, spray, mouse, lotion, ointment, make-up product, lip balm, hair spray product, arachnid/insect repellent or medicinal product known or apparent to one of skill in the art. A skin care product may be applied by hand, washcloth, or any cleansing article such as a brush, loofah, pouf, sponge, or other to an individual.

A bodywash includes, without limitation, a lathering bodywash or a non-lathering bodywash. A bodywash includes, without limitation, an emulsion of water and detergent base with added fragrance and is a skin cleaning agent commonly used in a shower or bath. A bodywash may also contain one or more surfactants. Popular brands such as Fa, Palmolive, Axe, Lynx, Radox, *Nivea*, Johnson, Senses, Adidas, Umbro, Old Spice, Imperial Leather and right guard. A bodywash also includes, without limitation an all-in-one multifunctional, moisturizing cleanser that both provides SPF and imparts color to the skin after application, wherein the bodywash includes, without limitation, iron oxide pigments as well as red petrolatum, at least one, preferably two, anionic lathering surfactants, a non-ionic lathering surfactant, surface-treated zinc oxide pigments, an alkyl silicone and a volatile cyclic silicone.

A spray includes, without limitation, an aerosol spray that includes a propellant. A propellant includes, without limitation is a mixture of isobutane, butane and propane, including, without limitation A46, AP30 (11% propane, 29% isobutane, 60% n-butane); AP40 (22% propane, 24% isobutane, 54% n-butane); and AP70 (31% propane, 23% isobutane, 46% n-butane). A spray includes, without limitation, hair spray, body spray, for example, without limitation, those sold by AXE, spray on insect protection and spray on deodorant.

A shampoo includes, without limitation, sodium lauryl sulfate and/or sodium laureth sulfate with a co-surfactant, including, without limitation, cocamidopropyl betaine in water to form a thick, viscous liquid. A shampoo includes salt, including, without limitation, sodium chloride, a preservative and a fragrance. In an embodiment, a shampoo is formulated to maximize the following qualities, without limitation, pleasing foam, easy rinsing, minimal skin or eye irritation, feels thick and/or creamy, pleasant fragrance, low toxicity, good biodegradability, slightly acidic and no or minimal damage to hair.

A lotion includes, without limitation, a low to low medium viscosity topical preparation intended for application to unbroken skin. A lotion is an oil-in-water emulsion that includes, without limitation, cetearyl alcohol and an emulgent to prevent separation of these two phases. A lotion contains, without limitation, fragrances, glycerol, petroleum jelly, dyes, preservatives, proteins and stabilizing agents. A lotion includes, without limitation a skin medication such as an antibiotic, antiseptic, antifungal, corticosteroid, anti-acne agents or soothing, smoothing, moisturizing or protective agents, including, without limitation, calamine. A gel includes, without limitation, a solid, jelly-like material that can have properties ranging from soft and weak to hard and tough and include, without limitation, substantially dilute cross-linked system, which exhibit no flow when in a steady-state. In an embodiment a gel includes, without limitation, a hydrogel, an organogel or a xerogel.

A conditioner includes, without limitation, hair conditioner, which can include, without limitation, the following ingredients: moisturizers, reconstructors, acidifiers, detanglers, thermal protectors, glossers, oils, surfactants, lubricants, sequestrants, antistatic agents, and preservatives. A conditioner includes, without limitation, a pack conditioner, a leave-in conditioner, an ordinary conditioner that includes both pack and leave-in ones and hold conditioners.

A hand sanitizer includes, without limitation, isopropanol, ethanol, n-propanol or povidone-iodine. In a further embodiment, hand sanitizers can contain the following inactive ingredients, without limitation, a thickening agent, including without limitation, polyacrylic acid for alcohol gels, humectants, including without limitation, glycerin for liquid rubs, propylene glycol and essential oils derived from plants. A hand sanitizer is a non-alcohol hand sanitizer, which includes without limitation, a nitrogenous cationic surface-acting agent that includes, without limitation, benzalkonium chloride, triclosan or povidone-iodine.

A soap is a salt of a fatty acid. Soaps for cleansing are generally obtained by treating vegetable or animal oils and fats with a strongly alkaline solution. Soaps can be in a solid form, such as a bar or in a decorative shape. Soap can also be a liquid. Other components can be added to soap, without limitation, including oils, fragrances and conditioners. In a further embodiment, a soap contains a surfactant. In another embodiment, a soap does not contain a surfactant.

In an embodiment, a soap is a melt and pour soap. The process for a melt and pour soap differs from the cold process, hot process or rebatching process of making soap in that no soap is made (i.e. no actual saponification occurs) in the process; a melt and pour soap base acquired in commerce is melted in a direct heat melter or water jacket melting pot (large double boiler) and additional items such as fragrance, essential oils, moisturizing agents, colorants, or exfoliating agents are added. While still hot, the concoction can be poured into individual molds, tray molds, or blocks which upon cooling can be sliced. A melt and pour soap includes, without limitation, a clear glycerin soap or a white soap made from white coconut oil.

In an embodiment, a soap is Castile soap. Castile soap is a name used in English-speaking countries for olive oil based soap made in a style similar to that originating in the Castile region of Spain. In an embodiment, Castile soap includes, without limitation, sodium hydroxide, potassium hydroxide and/or ash.

In one embodiment, a composition disclosed herein is use in combination as an admixture with a skin care product disclosed herein. A composition disclosed herein when combined as an admixture with a skin care product in an amount sufficient to allow the one or more active agents, cationic polymers, film formers, photostabilizing agents, surfactant metal complexes, and additional agents to function properly. In aspects of this embodiment, a composition disclosed herein is combined with a skin care product in a ratio of, e.g., about 1.0 part composition to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.5, 3.7, 4.0, 4.2, 4.5, 4.7, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 parts skin care product as measured w/w.

In other aspects of this embodiment, a composition disclosed herein is combined with a skin care product in a ratio range of, e.g., about 1.0 part composition to about 0.1 to about 1.0 part skin care product as measured w/w, about 1.0 part composition to about 0.1 to about 5.0 parts skin care product as measured w/w, about 1.0 part composition to about 0.1 to about 10 parts skin care product as measured w/w, about 1.0 part composition to about 0.1 to about 15 parts skin care product as measured w/w, about 1.0 part composition to about 0.1 to about 20 parts skin care product as measured w/w, about 1.0 part composition to about 0.5 to about 1.0 part skin care product as measured w/w, about 1.0 part composition to about 0.5 to about 5.0 parts skin care product as measured w/w, about 1.0 part composition to about 0.5 to about 10 parts skin care product as measured w/w, about 1.0 part composition to about 0.5 to about 15 parts skin care product as measured w/w, about 1.0 part composition to about 0.5 to about 20 parts skin care product as measured w/w, about 1.0 part composition to about 1.0 to about 5.0 parts skin care product as measured w/w, about 1.0 part composition to about 1.0 to about 10 parts skin care product as measured w/w, about 1.0 part composition to about 1.0 to about 15 parts skin care product as measured w/w, about 1.0 part composition to about 1.0 to about 20 parts skin care product as measured w/w, about 1.0 part composition to about 5.0 to about 25 parts skin care product as measured w/w, about 1.0 part composition to about 1.0 to about 30 parts skin care product as measured w/w, about 1.0 part composition to about 1.0 to about 35 parts skin care product as measured w/w, about 1.0 part composition to about 1.0 to about 40 parts skin care product as measured w/w, about 1.0 part composition to about 1.0 to about 45 parts skin care product as measured w/w, about 1.0 part composition to about 1.0 to about 50 parts skin care product as measured w/w, about 1.0 part composition to about 1.0 part composition to about 5.0 to about 10 parts skin care product as measured w/w, about 1.0 part composition to about 5.0 to about 15 parts skin care product as measured w/w, about 1.0 part composition to about 5.0 to about 20 parts skin care product as measured w/w, about 1.0 part composition to about 5.0 to about 25 parts skin care product as measured w/w, about 1.0 part composition to about 5.0 to about 30 parts skin care product as measured w/w, about 1.0 part composition to about 5.0 to about 35 parts skin care product as measured w/w, about 1.0 part composition to about 5.0 to about 40 parts skin care product as measured w/w, about 1.0 part composition to about 5.0 to about 45 parts skin care product as measured w/w or about 1.0 part composition to about 5.0 to about 50 parts skin care product as measured w/w.

In an embodiment, a composition disclosed herein is formulated as a skin care product. In aspects of this embodiment, a composition disclosed herein is formulated as a body wash, after shower body lotion, shampoo, conditioner, soap, gel, hand sanitizer, cream, spray, mouse, lotion, ointment, make-up product, lip balm, hair spray product, arachnid/insect repellent or medicinal product disclosed herein. Besides the one or more agents, like arachnid/insect repellents, cationic polymers, film formers, photostabilizing agents, surfactant metal complexes, and additional agents disclosed herein, such skin care products include additional ingredients necessary to formulate the skin care product.

A composition disclosed herein formulated as a skin care product disclosed herein typically requires the use of one or more surfactants. A surfactant may be cationic, anionic, non-ionic, zwitterionic, amphoteric, or any combination thereof. In a further embodiment, surfactants include, without limitation, alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, ethoxylated alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention. In a further embodiment, alkyl sulfates include, without limitation, sodium, ammonium, potassium, magnesium, or TEA salts of lauryl or myristyl sulfate or ammonium, sodium, magnesium, or TEA laureth-3 sulfate.

A composition disclosed herein comprises a surfactant in an amount sufficient to promote or facilitate the function or activity of that surfactant. In aspects of this embodiment, a composition disclosed herein comprises a surfactant in an amount of, e.g., at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition. In other aspects of this embodiment, a composition disclosed herein comprises a surfactant in an amount of, e.g., at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition.

In other aspects of this embodiment, a composition disclosed herein comprises a surfactant in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

In an embodiment, a surfactant is an environmentally favourable surfactant including, without limitation, dodecyl glucosides.

In an embodiment, a surfactant is a lathering surfactant. A lathering surfactant has a log P of less than about 2.5 that produces foam when mixed with and agitated in water. An anionic lathering surfactant is a sulfate, wherein the sulfate is, without limitation, an alkyl sulfate or an alkyl ether sulfate. A sulfate includes, without limitation, sodium laureth sulfate and ammonium laureth sulfate. Sodium laureth sulfate has a molecular formula $CH_3(CH_2)_{10}CH_2(OCH_2CH_2)_{20}SO_3Na$ and conforms to the following structure:

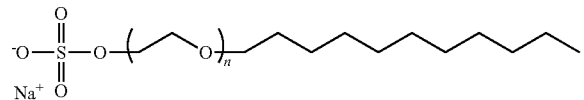

In an embodiment, a composition or a skin care product combined with a composition, includes, without limitation, sodium laureth sulfate at a concentration of from about 10% to about 15% or from about 7.5% to about 8.5%. In a further embodiment, ammonium laureth sulfate is used in combination with an alkyl glucoside, wherein the alkyl glucoside includes, without limitation, decyl glucoside. The combination of ammonium laureth sulfate and decyl glucoside is sold under the tradename Plantaren PS-100 by Cognis. In an embodiment, ammonium laureth sulfate in combination with decyl glucoside is present in a composition or body wash, after shower body lotion, shampoo, conditioner, soap, gel, hand sanitizer, cream, spray, mouse, lotion, ointment, make-up product, lip balm, hair spray product, arachnid/insect repellent or medicinal product combined with a composition at a concentration of from about 5% to about 10%, or from about 7.5% to about 8.5%.

In a further embodiment, a lathering surfactant includes one, two, three or more anionic lathering surfactants, including, without limitation, sulfates, including, without limitation, sodium laureth sulfate and ammonium laureth sulfate. In an embodiment, sodium laureth sulfate and ammonium laureth sulfate are combined with decyl glucoside. In an additional embodiment, the two sulfates are present at a combined concentration of from about 15% to about 25%.

In an embodiment, a composition disclosed herein includes, without limitation, at least one cationic surfactant. In an embodiment, cationic surfactants include, without limitation, fatty amines, di-fatty quaternary amines, tri-fatty quaternary amines, imidazolinium quaternary amines, and combinations thereof. In a further embodiment, fatty amines include, without limitation, monalkyl quaternary amines such as cetyltrimethylammonium bromide. In an embodiment, quaternary amine include, without limitation, dialklamidoethyl hydroxyethylmonium methosulfate, In an embodiment, a composition disclosed herein includes, without limitation, stearyldimenthylbenzyl ammonium chloride; dodecyltrimethylammonium chloride; nonylbenzylethyldimethyl ammonium nitrate; tetradecylpyridinium bromide;

laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride. Additional cationic surfactants are disclosed in U.S. Pat. No. 4,303,543 see column 4, lines 58 and column 5, lines 1 42, incorporated herein by references. Also see CTFA Cosmetic Ingredient Dictionary, 4th Edition 1991, pages 509 514 for various long chain alkyl cationic surfactants; incorporated herein by reference.

In a further embodiment, anionic surfactants, include, without limitation, sulfated monoglycerides of the form $R^1CO$—O—$CH_2$—C(OH)H—$CH_2$—O—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine, monoethanolamine and sodium cocomonoglyceride sulfate. In a further embodiment, anionic surfactants include, without limitation, olefin sulfonates of the form $R^1SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. In an embodiment, a sulfonated olefin is sodium C14/C16 alpha olefin sulfonate. In a further embodiment, anionic surfactants, include, without limitation, linear alkylbenzene sulfonates of the form $R^1$—$C_6H_4$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine monoethanolamine and sodium dodecylbenzene sulfonate. In an additional embodiment, anionic surfactants include, without limitation, primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. In a further embodiment, alkane sulfonate include, without limitation, alkali metal or ammonium $C_{13-17}$ paraffin sulfonates. In an additional embodiment, anionic surfactants include, without limitation, alkyl sulfosuccinates, which include disodium N-octadecylsulfosuccinamate, diammonium lauryl sulfosuccinate, disodium laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate and ammonium lauryl sulfate.

Acyl taurate surfactants include, without limitation, taurine, N-alkyltaurines such as the one prepared by reacting dodecylamine with sodium isethionate as detailed in U.S. Pat. No. 2,658,072, and coconut fatty acid salts, such as, e.g., sodium methyl cocoyl taurate and sodium methyl oleoyl taurate.

In a further embodiment, anionic surfactants include, without limitation, acyl isethionates, including, without limitation, acyl isethionates include ammonium cocoyl isethionate, sodium cocoyl isethionate, sodium lauroyl isethionate, alkylglyceryl ether sulfonates of the form $R^1$—$OCH_2$—C(OH)H—$CH_2$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine, sodium cocoglyceryl ether sulfonate, sulfonated fatty acids of the form $R^1$—CH($SO_4$)—COOH and sulfonated methyl esters of the from $R^1$—CH($SO_4$)—CO—O—$CH_3$, where $R^1$ is a saturated or unsaturated, branched or unbranched alkyl group from about 8 to about 24 carbon atoms (e.g., alpha sulphonated coconut fatty acid and lauryl methyl ester); phosphates such as monoalkyl, dialkyl, and trialkylphosphate salts formed by the reaction of phosphorous pentoxide with monohydric branched or unbranched alcohols having from about 8 to about 24 carbon atoms (e.g., sodium mono or dilaurylphosphate, ethoxylated monoalkyl phosphates, etc.); acyl glutamates corresponding to the formula $R^1CO$—N(COOH)—$CH_2CH_2$—$CO_2M$ wherein $R^1$ is a saturated or unsaturated, branched or unbranched alkyl or alkenyl group of about 8 to about 24 carbon atoms, and M is a water-soluble cation (e.g., sodium lauroyl glutamate and sodium cocoyl glutamate); alkanoyl sarcosinates corresponding to the formula $R^1CON(CH_3)$—$CH_2CH_2$—$CO_2M$ wherein $R^1$ is a saturated or unsaturated, branched or unbranched alkyl or alkenyl group of about 10 to about 20 carbon atoms, and M is a water-soluble cation (e.g., sodium lauroyl sarcosinate, lauroyl sarcosine, sodium cocoyl sarcosinate, and ammonium lauroyl sarcosinate); alkyl ether carboxylates corresponding to the formula $R^1$—($OCH_2CH_2$)x-$OCH_2$—$CO_2M$ wherein $R^1$ is a saturated or unsaturated, branched or unbranched alkyl or alkenyl group of about 8 to about 24 carbon atoms, x is 1 to 10, and M is a water-soluble cation (e.g., sodium laureth carboxylate); acyl lactylates corresponding to the formula $R^1CO$—[O—CH($CH_3$)—CO]x-$CO_2M$ wherein $R^1$ is a saturated or unsaturated, branched or unbranched alkyl or alkenyl group of about 8 to about 24 carbon atoms, x is 3, and M is a water-soluble cation (e.g., sodium cocoyl lactylate); carboxylates, nonlimiting examples of which include sodium lauroyl carboxylate, sodium cocoyl carboxylate, and ammonium lauroyl carboxylate; anionic flourosurfactants; and natural soaps derived from the saponification of vegetable and/or animal fats & oils examples of which include sodium laurate, sodium myristate, palmitate, stearate and tallowate, cocoate. In a further embodiment, a soap is a semi-solid. In another embodiment, a soap includes a wax to form a solid soap bar.

In an embodiment a counter cation, M, is used on the anionic surfactant. In a further embodiment, a counter cation includes, without limitation, sodium, potassium, ammonium, monoethanolamine, diethanolamine, and triethanolamine.

In an embodiment, non-ionic surfactants include, without limitation, alkyl glucosides, alkyl polyglucosides, polyhydroxy fatty acid amides, alkoxylated fatty acid esters, sucrose esters, amine oxides, and mixtures thereof. Alkyl glucosides and alkyl polyglucosides are condensation products of long chain alcohols, including, without limitation, $C_{8-30}$ alcohols, with sugars or starches or sugar or starch polymers, including, without limitation, glycosides or polyglycosides and are represented by the formula $(S)_n$—O—R wherein S is a sugar moiety such as glucose, fructose, mannose, and galactose; n is an integer of from about 1 to about 1000, and R is a $C_{8-30}$ alkyl group. In an embodiment, long chain alcohols from which the alkyl group can be derived include, without limitation, decyl alcohol, cetyl alcohol, stearyl alcohol, lauryl alcohol, myristyl alcohol, oleyl alcohol, and more. In a further embodiment, these surfactants include, without limitation, those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). In an additional embodiment, sucrose ester surfactants include, without limitation, sucrose cocoate and sucrose laurate.

In another embodiment, non-ionic surfactants include, without limitation, polyhydroxy fatty acid amide surfactants, more specific examples of which include glucosamides. In an embodiment a process for making compositions containing polyhydroxy fatty acid amides are disclosed, for example, in G.B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934. In an embodiment, non-ionic surfactants include, without limitation, amine oxides, including, without limitation, those corresponding to the general formula $R_1R_2$, $R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. In an embodiment, amine oxides include, without limitation, dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

The term "amphoteric surfactant," as used herein, is also intended to encompass zwitterionic surfactants, which are well known to formulators skilled in the art as a subset of amphoteric surfactants. Amphoteric lathering surfactants include, without limitation, derivatives of aliphatic secondary and tertiary amines, including, without limitation, those wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate. In an embodiment, amphoteric or zwitterionic surfactants include, without limitation, betaines, sultaines, hydroxysultaines, alkyliminoacetates, iminodialkanoates, aminoalkanoates, and mixtures thereof. In an embodiment, betaines include, without limitation, the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alphacarboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel). In a further embodiment, sultaines and hydroxysultaines include, without limitation, materials such as cocamidopropyl hydroxysultaine (available as Mirataine CBS from Rhone-Poulenc).

In an embodiment, amphoteric surfactants include, without limitation, the following compounds: Cetyl dimethyl betaine (this material also has the CTFA designation cetyl betaine); Cocamidopropylbetaine; Cocamidopropyl hydroxy sultaine. Examples of other useful amphoteric surfactants are alkyliminoacetates, and iminodialkanoates and aminoalkanoates of the formulas $RN[(CH_2)-CO_2-M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, alkanolammonium or imidazolinium and ammonium derivatives. In a further embodiment, amphoteric surfactants include, without limitation, sodium 3-dodecyl-aminopropionate, sodium 3-dodecylaminopropane sulfonate. In a further embodiment, N-higher alkyl aspartic acids include, without limitation, those produced according to the teaching of U.S. Pat. No. 2,438,091; and the products sold under the trade name "Miranol" and described in U.S. Pat. No. 2,528,378. In a further embodiment, amphoterics include, without limitation, amphoteric phosphates, such as coamidopropyl PG-dimonium chloride phosphate (commercially available as Monaquat PTC, from Mona Corp.). In another embodiment, amphoacetates include, without limitation, disodium lauroamphodiacetate, sodium lauroamphoacetate, and mixtures thereof.

In an embodiment, a bodywash is, without limitation, SUAVE Body Wash, which has the following ingredients: Water, Ammonium Lauryl Sulfate, Ammonium Laureth Sulfate, Cocamidopropyl Betaine, Fragrance, Glycerin, Hydrolyzed Milk Protein & Honey Extract, PEG-10 Sunflower Glycerides, Cocamide MEA, Guar Hydroxypropylrimonium Chloride, Acrylates Copolymer, PEG-5 Cocamide, *Helianthus Annuus* (Sunflower) Seed Oil or *Glycine Soja* (Soybean) Oil, Tetrasoidum EDTA, Propylene Glycol, Ammonium Chloride, Sodium Hydroxide, Methylchloroisothiazolinone, Methylisothiazolinone, Titanium Dioxide (CI 77891).

In an embodiment, soapless cleansers are used in addition to, or instead of, soaps/surfactants, including, without limitation OILATUM™ AD (registered trademark, Stiefel Laboratories) AQUANIL™ (registered trademark, Person & Covey, Inc.), CETAPHIL™ (trademark, Galderma Laboratories, Inc.) or SPECTRODERM™ (registered trademark, Draxis Pharmaceutical Inc.), or their equivalents, may be utilized as a soapless component in the present invention.

In an embodiment, the composition containing an active agent is a powder or other dry form. In a further embodiment, the composition containing an active agent is applied to an individual by applying the powder or other dry form to the individual. In a further embodiment, following application of the powder or other dry form, the composition containing an active agent is rubbed, massaged, caressed onto the individual. In an embodiment, the composition containing an active agent that is in the form of a powder or other dry form is stored in an applicator. In an embodiment, the applicator is the same as the applicator used for powder or other dry form products, including, without limitation, a baby powder bottle or other applicator that is conformed to the application of a powder or other dry form of a composition.

In an embodiment, the components comprising a composition are mixed in, without limitation, water or oil. In an embodiment, a composition or composition combined with a body wash, after shower body lotion, shampoo, conditioner, soap, gel, hand sanitizer, cream, spray, mouse, lotion, ointment, make-up product, lip balm, hair spray product, arachnid/insect repellent or medicinal product includes, without limitation, one or more surfactants. The use of surfactants in bodywashes is well-known in the art. Any surfactant known in the art and appropriate for a body wash, after shower body lotion, shampoo, conditioner, soap, gel, hand sanitizer, cream, spray, mouse, lotion, ointment, make-up product, lip balm, hair spray product, arachnid/insect repellent or medicinal product may be used. See, McCutcheon's Detergents & Emulsifiers, M.C. Publishing Co. (North American edition 1989); Schwartz, et al., Surface Active Agents, Their Chemistry and Technology, New York, Interscience Publishers, 1949, and U.S. Pat. Nos. 6,096,697; 4,741,855; 4,788,066; 5,104,646; 5,106,609; 2,658,072; 4,438,091; 2,528,378; 2,486,921; 2,486,922; 2,396,278; 2,979,465; 3,179,599; 5,322,643; 5,084,212; 3,332,880; 4,122,029; 4,265,878; 4,421,769; 3,929,678; 3,959,461; 4,387,090; 4,303,543; and 6,224,852; and in British Patent Nos. 848,224 and 791,415. Also see CTFA Cosmetic Ingredient Dictionary, 4th Edition 1991, pages 509 514 for various long chain alkyl cationic surfactants; and Richmond, James M., Cationic Surfactants, Marcel Dekker, Inc., New York and Basel, 1990.

In an embodiment, a composition disclosed herein comprises one or more cellulose derived encapsulates and/or one or more sol-gel encapsulates comprising one or more arachnid/insect repellents. In aspects of this embodiment, a composition disclosed herein comprises 8% to about 20%, about 10% to about 18%, about 11% to about 17%, about 13% to about 15% or about 14% by weight of the total composition of a cellulose encapsulate and/or of a sol-gel encapsulate comprising one or more arachnid/insect repellents. In other aspects of this embodiment, a composition disclosed herein comprises about 14% to about 26%, about 16% to about 24%, about 17% to about 23%, about 19% to about 21% or about 20% by weight of the total composition of a cellulose encapsulate and/or of a sol-gel encapsulate comprising one or more arachnid/insect repellents. In yet other aspects of this embodiment, a composition disclosed herein comprises about 2% to about 40%, about 3% to about 38%, about 4% to about 36%, about 5% to about 36%, about 6% to about 34%, about 8% to about 32%, about 10% to about 30%, about 12% to about 28%, about 14% to about 26%, about 16% to about 24%, or about 18% to about 22%, by weight of the total composition of a cellulose encapsulate and/or of a sol-gel encapsulate comprising one or more arachnid/insect repellents. In yet other aspects of this embodiment, a composition disclosed herein comprises one or more encapsulates disclosed herein including about 40% to about 54% of an arachnid/insect repellent, about 42% to about 52% of an arachnid/insect repellent, about 44% to about 50% of an arachnid/insect repellent, about 46% to about 48% of an arachnid/insect repellent, about 47% of an arachnid/insect repellent.

In other aspects of this embodiment, a composition disclosed herein comprises one or more cellulose encapsulates and/or one or more sol-gel encapsulates disclosed herein comprises about 1% to about 5% of a first arachnid/insect repellent, about 95% to about 99% of a second arachnid/insect repellent, about 6% to about 10% of a first arachnid/insect repellent, about 90% to about 94% of a second arachnid/insect repellent, about 11% to about 15% of a first arachnid/insect repellent, about 85% to about 89% of a second arachnid/insect repellent, about 16% to about 20% of a first arachnid/insect repellent, about 80% to about 84% of a second arachnid/insect repellent, about 21% to about 25% of a first arachnid/insect repellent, about 75% to about 79% of a second arachnid/insect repellent, about 26% to about 30% of a first arachnid/insect repellent, about 70% to about 74% of a second arachnid/insect repellent, about 31% to about 35% of a first arachnid/insect repellent, about 65% to about 69% of a second arachnid/insect repellent, about 36% to about 40% of a first arachnid/insect repellent, about 60% to about 64% of a second arachnid/insect repellent, about 41% to about 45% of a first arachnid/insect repellent, about 55% to about 59% of a second arachnid/insect repellent, or about 46% to about 50% of a first arachnid/insect repellent, about 50% to about 54% of a second moisturizing agents. In yet other aspects of this embodiment, a composition disclosed herein comprises one or more cellulose encapsulates and/or one or more sol-gel encapsulates disclosed herein comprises about 17% to about 30% of a first arachnid/insect repellent, about 17% to about 30% of a second arachnid/insect repellent, about 19% to about 28% of a first arachnid/insect repellent, about 19% to about 28% of a second arachnid/insect repellent, about 21% to about 26% of a first arachnid/insect repellent, about 21% to about 26% of a second arachnid/insect repellent, about 23% to about 24% of a first arachnid/insect repellent, about 23% to about 24% of a second arachnid/insect repellent, about 23.5% of a first arachnid/insect repellent, about 23.5 of a second arachnid/insect repellent.

In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In another embodiment, a composition disclosed herein further comprises a film former. In aspects of this embodiment, a composition disclosed herein comprises about 1% to about 6%, about 1.5% to about 4.5%, about 2% to about 4%, about 2.5% to about 3.5% or about 3% of a film former. In other aspects of this embodiment, a composition disclosed herein comprises an acrylate copolymer as a film former. In yet other aspects of this embodiment, a composition disclosed herein comprises DERMACRYL® AQF as a film former.

In another embodiment, a composition disclosed herein further comprise one or more surfactants. In aspects of this embodiment, a composition disclosed herein comprises about 0.1% to about 20%, about 0.25% to about 18%, about 0.5% to about 15%, about 0.5% to about 12%, about 0.75% to about 10%, about 1% to about 8%, of one or more surfactants. In aspects of this embodiment, additional surfactants include additional cationic surfactants, anionic surfactants, non-ionic surfactants, zwitterionic surfactants, amphoteric surfactants, or any combination thereof.

In an embodiment, a composition disclosed herein comprises a cellulose encapsulate and/or of a sol-gel encapsulate comprising one or more arachnid/insect repellents, one or more polyquarterniums, and one or more surfactants. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition comprises about 14% to about 26% of a cellulose encapsulate and/or of a sol-gel encapsulate comprising about 88% to about 100% of one or more arachnid/insect repellents, about 0.1% to about 10% of one or more polyquarterniums, and about 3% to about 17% one or more surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, and about 5% to about 15% one or more surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, and about 7% to about 13% one or more surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, and about 9% to about 11% one or more surfactants. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, and about 10% one or more surfactants.

In aspects of this embodiment, a composition comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, and about 3% to about 17% one or more surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.2% to about 8% of one or more polyquarterniums, and about 5% to about 15% one or more surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, and about 7% to about 13% one or more surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, and about 9% to about 11% one or more surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, and about 10% one or more surfactants.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of one or more polyquarterniums, and about 2% to about 18% one or more surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, and about 3% to about 15% one or more surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, and about 4% to about 13% one or more surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, and about 5% to about 12% one or more surfactants. In other aspects of this embodiment, a disclosed herein comprises about 20% of a cellulose encapsulate and/or of a sol-gel encapsulate comprising about 94% of one or more arachnid/insect repellents, about 2.5% of one or more polyquarterniums, and about 6% to about 11% one or more surfactants.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, and about 2% to about 18% one or more surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.2% to about 8% of one or more polyquarterniums, and about 3% to about 15% one or more surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, and about 4% to about 13% one or more surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, and about 5% to about 12% one or more surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, and about 6% to about 11% one or more surfactants.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of one or more polyquarterniums, and about 1% to about 20% one or more surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.1% to about 5% of one or more polyquarterniums, and about 4% to about 14% of one or more surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.1% to about 3% of one or more polyquarterniums, and about 7% to about 11% one or more surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.25% to about 2.5% of one or more polyquarterniums, and about 8% to about 10% one or more surfactants. In other aspects of this embodiment, a composition disclosed herein comprises about 20% of a cellulose encapsulate and/or of a sol-gel encapsulate comprising about 94% of one or more arachnid/insect repellents, about 0.5% of one or more polyquarterniums, and about 8.8% one or more surfactants.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, and about 1% to about 20% one or more surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.1% to about 5% of one or more polyquarterniums, and about 4% to about 14% one or more surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.1% to about 3% of one or more polyquarterniums, and about 7% to about 11% one or more surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.25% to about 2.5% of one or more polyquarterniums, and about 8% to about 10% one or more surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 0.5% of one or more polyquarterniums, and about 8.8% one or more surfactants.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of one or more polyquarterniums, about 0.5% to about 15% one or more anionic surfactants, about 0.1% to about 5% one or more amphoteric surfactants and about 0.1% to about 5% one or more acyl taurate surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, about 1% to about 10% one or more anionic surfactants, about 0.25% to about 4% one or more amphoteric surfactants and about 0.25% to about 4% one or more acyl taurate surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, about 2% to about 9% one or more anionic surfactants, about 0.5% to about 3% one or more amphoteric surfactants and about 0.5% to about 3% one or more acyl taurate surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, about 3% to about 8% one or more anionic surfactants, about 0.75% to about 2.5% one or more amphoteric surfactants and about 0.75% to about 2.5% one or more acyl taurate surfactants. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 4% to about 7% one or more anionic surfactants, about 1% to about 2% one or more amphoteric surfactants and about 1% to about 2% one or more acyl taurate surfactants.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 20% of one or more polyquarterniums, about 0.5% to about 15% one or more anionic surfactants, about 0.1% to about 5% one or more amphoteric surfactants and about 0.1% to about 5% one or more acyl taurate surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.2% to about 8% of one or more polyquarterniums, about 1% to about 10% one or more anionic surfactants, about 0.25% to about 4% one or more amphoteric surfactants and about 0.25% to about 4% one or more acyl taurate surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, about 2% to about 9% one or more anionic surfactants, about 0.5% to about 3% one or more amphoteric surfactants and about 0.5% to about 3% one or more acyl taurate surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, about 3% to about 8% one or more anionic surfactants, about 0.75% to about 2.5% one or more amphoteric surfactants and about 0.75% to about 2.5% one or more acyl taurate surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 4% to about 7% one or more anionic surfactants, about 1% to about 2% one or more amphoteric surfactants and about 1% to about 2% one or more acyl taurate surfactants.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of one or more polyquarterniums, about 1% to about 16% of one or more anionic surfactants, about 0.1% to about 10% of an amphoteric surfactant and about 0.1% to about 10% of a surfactant. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.1% to about 5% of one or more polyquarterniums, about 1% to about 12% of one or more anionic surfactants, about 0.25% to about 8% of an amphoteric surfactant and about 0.25% to about 8% of a surfactant. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.1% to about 3% of one or more polyquarterniums, about 3% to about 9% of one or more anionic surfactants, about 0.5% to about 5% of an amphoteric surfactant and about 0.5% to about 5% of a surfactant. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.25% to about 2.5% of one or more polyquarterniums, about 5% to about 7% of one or more anionic surfactants, about 1% to about 3% of an amphoteric surfactant and about 1% to about 3% of a surfactant. In other aspects of this embodiment, a composition disclosed herein comprises about 20% of a cellulose encapsulate and/or of a sol-gel encapsulate comprising about 94% of one or more arachnid/insect repellents, about 0.5% of one or more polyquarterniums, about 5.6% of one or more anionic surfactants, about 1.6% of an amphoteric surfactant and about 1.6% of a surfactant.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarternient, about 1% to about 16% of one or more anionic surfactants, about 0.1% to about 10% of an amphoteric surfactant and about 0.1% to about 10% of a surfactant. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.1% to about 5% of one or more polyquarterniums, about 1% to about 12% of one or more anionic surfactants, about 0.25% to about 8% of an amphoteric surfactant and about 0.25% to about 8% of a surfactant. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.1% to about 3% of one or more polyquarterniums, about 3% to about 9% of one or more anionic surfactants, about 0.5% to about 5% of an amphoteric surfactant and about 0.5% to about 5% of a surfactant. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.25% to about 2.5% of one or more polyquarterniums, about 5% to about 7% of one or more anionic surfactants, about 1% to about 3% of an amphoteric surfactant and about 1% to about 3% of a surfactant. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 0.5% of one or more polyquarterniums, about 5.6% of one or more anionic surfactants, about 1.6% of an amphoteric surfactant and about 1.6% of a surfactant.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of one or more polyquarterniums, about 0.5% to about 8% one or more alkyl sulfosuccinate surfactants, about 0.1% to about 5% one or more acyl isethionate surfactants, about 0.1% to about 5% one or more betaine surfactants and about 0.1% to about 5% one or more acyl taurate surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, about 1% to about 7% one or more alkyl sulfosuccinate surfactants, about 0.25% to about 4% one or more acyl isethionate surfactants, about 0.25% to about 4% one or more betaine surfactants and about 0.25% to about 4% one or more acyl taurate surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, about 2% to about 6% one or more alkyl sulfosuccinate surfactants, about 0.5% to about 3% one or more acyl isethionate surfactants, about 0.5% to about 3% one or more betaine surfactants and about 0.5% to about 3% one or more acyl taurate surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, about 2.5% to about 5% one or more alkyl sulfosuccinate surfactants, about 0.75% to about 2.5% one or more acyl isethionate surfactants, about 0.75% to about 2.5% one or more betaine surfactants and about 0.75% to about 2.5% one or more acyl taurate surfactants. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 3% to about 4.5% one or more alkyl sulfosuccinate surfactants, about 1% to about 2% one or more acyl isethionate surfactants, about 1% to about 2% one or more betaine surfactants and about 1% to about 2% one or more acyl taurate surfactants.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 30% of one or more polyquarterniums, about 0.5% to about 8% one or more alkyl sulfosuccinate surfactants, about 0.1% to about 5% one or more acyl isethionate surfactants, about 0.1% to about 5% one or more betaine surfactants and about 0.1% to about 5% one or more acyl taurate surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.5% to about 15% of one or more polyquarterniums, about 1% to about 7% one or more alkyl sulfosuccinate surfactants, about 0.25% to about 4% one or more acyl isethionate surfactants, about 0.25% to about 4% one or more betaine surfactants and about 0.25% to about 4% one or more acyl taurate surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, about 2% to about 6% one or more alkyl sulfosuccinate surfactants, about 0.5% to about 3% one or more acyl isethionate surfactants, about 0.5% to about 3% one or more betaine surfactants and about 0.5% to about 3% one or more acyl taurate surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, about 2.5% to about 5% one or more alkyl sulfosuccinate surfactants, about 0.75% to about 2.5% one or more acyl isethionate surfactants, about 0.75% to about 2.5% one or more betaine surfactants and about 0.75% to about 2.5% one or more acyl taurate surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 3% to about 4.5% one or more alkyl sulfosuccinate surfactants, about 1% to about 2% one or more acyl isethionate surfactants, about 1% to about 2% one or more betaine surfactants and about 1% to about 2% one or more acyl taurate surfactants.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.1% to about 10% of a polyquarternium, about 0.1% to about 15% of an alkyl sulfosuccinate surfactant, about 0.1% to about 10% of an isethionate surfactant, about 0.1% to about 10% of a betaine surfactant and about 0.1% to about 10% of an acyl taurate surfactant. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.1% to about 5% of a polyquarternium, about 0.5% to about 10% of an alkyl sulfosuccinate surfactant, about 0.25% to about 8% of an isethionate surfactant, about 0.25% to about 8% of a betaine surfactant and about 0.25% to about 8% of an acyl taurate surfactant. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.1% to about 3% of a polyquarternium, about 1% to about 7% of an alkyl sulfosuccinate surfactant, about 0.5% to about 5% of an isethionate surfactant, about 0.5% to about 5% of a betaine surfactant and about 0.5% to about 5% of an acyl taurate surfactant. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.25% to about 2.5% of a polyquarternium, about 3% to about 5% of an alkyl sulfosuccinate surfactant, about 1% to about 3% of an isethionate surfactant, about 1% to about 3% of a betaine surfactant and about 1% to about 3% of an acyl taurate surfactant. In other aspects of this embodiment, a composition disclosed herein comprises about 20% of a cellulose encapsulate and/or of a sol-gel encapsulate comprising about 94% of one or more arachnid/insect repellents, about 0.5% of a polyquarternium, about 4% of an alkyl sulfosuccinate surfactant, about 1.6% of an isethionate surfactant, about 1.6% of a betaine surfactant and about 1.6% of an acyl taurate surfactant.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of a polyquarternium, about 0.1% to about 15% of an alkyl sulfosuccinate surfactant, about 0.1% to about 10% of an isethionate surfactant, about 0.1% to about 10% of a betaine surfactant and about 0.1% to about 10% of an acyl taurate surfactant. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.1% to about 5% of a polyquarternium, about 0.5% to about 10% of an alkyl sulfosuccinate surfactant, about 0.25% to about 8% of an isethionate surfactant, about 0.25% to about 8% of a betaine surfactant and about 0.25% to about 8% of an acyl taurate surfactant. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.1% to about 3% of a polyquarternium, about 1% to about 7% of an alkyl sulfosuccinate surfactant, about 0.5% to about 5% of an isethionate surfactant, about 0.5% to about 5% of a betaine surfactant and about 0.5% to about 5% of an acyl taurate surfactant. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.25% to about 2.5% of a polyquarternium, about 3% to about 5% of an alkyl sulfosuccinate surfactant, about 1% to about 3% of an isethionate surfactant, about 1% to about 3% of a betaine surfactant and about 1% to about 3% of an acyl taurate surfactant. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 0.5% of a polyquarternium, about 4% of an alkyl sulfosuccinate surfactant, about 1.6% of an isethionate surfactant, about 1.6% of a betaine surfactant and about 1.6% of an acyl taurate surfactant.

In an embodiment, a composition disclosed herein comprises a cellulose encapsulate and/or of a sol-gel encapsulate comprising one or more arachnid/insect repellents, one or more emollients and one or more thickening agents. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.25% to about 10% one or more emollients and about 0.5% to about 12% one or more thickening agents. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.5% to about 8% one or more emollients and about 1% to about 10% one or more thickening agents. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 1% to about 6% one or more emollients and about 1.5% to about 8.5% one or more thickening agents. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 2% to about 5% one or more emollients and about 2.5% to about 6.5% one or more thickening agents. In other aspects of this embodiment, a composition disclosed herein comprises about 20% of a cellulose encapsulate and/or of a sol-gel encapsulate comprising about 94% of one or more arachnid/insect repellents, about 3.4% one or more emollients and about 4.5% one or more thickening agents.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.25% to about 10% one or more emollients and about 0.5% to about 12% one or more thickening agents. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.5% to about 8% one or more emollients and about 1% to about 10% one or more thickening agents. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 1% to about 6% one or more emollients and about 1.5% to about 8.5% one or more thickening agents. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 2% to about 5% one or more emollients and about 2.5% to about 6.5% one or more thickening agents. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 3.4% one or more emollients and about 4.5% one or more thickening agents.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a composition disclosed herein comprises about 20% of a cellulose encapsulate and/or of a sol-gel encapsulate comprising about 94% of one or more arachnid/insect repellents, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 3.5% one or more emollients, about 2% one or more silicone elastomer thickening agents and about 2.5% one or more sodium acrylate-sodium acryloyldimethyl taurate copolymer-based thickening agents.

In an embodiment, a composition disclosed herein comprises a cellulose encapsulate and/or of a sol-gel encapsulate comprising one or more arachnid/insect repellents, one or more polyquarterniums, one or more film formers, one or more emollients and one or more thickening agents. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein comprises about 14% to about 26% of a cellulose encapsulate and/or of a sol-gel encapsulate comprising about 88% to about 100% of one or more arachnid/insect repellents, about 0.5% to about 8% of one or more polyquarterniums, about 0.5% to about 8% of one or more film formers, about 0.25% to about 10% one or more emollients and about 0.5% to about 12% one or more thickening agents. In other aspects of this embodiment, a composition disclosed herein comprises about 16% to about 24% of a cellulose encapsulate and/or of a sol-gel encapsulate comprising about 90% to about 98% of one or more arachnid/insect repellents, about 1% to about 5% of one or more polyquarterniums, about 1% to about 5% of one or more film formers, about 0.5% to about 8% one or more emollients and about 1% to about 10% one or more thickening agents. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 1.5% to about 3.5% of one or more polyquarterniums, about 1.5% to about 3.5% of one or more film formers, about 1% to about 6% one or more emollients and about 1.5% to about 8.5% one or more thickening agents. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 2% to about 3% of one or more polyquarterniums, about 2% to about 3% of one or more film formers, about 2% to about 5% one or more emollients and about 2.5% to about 6.5% one or more thickening agents. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 2.5% of one or more film formers, about 3.4% one or more emollients and about 4.5% one or more thickening agents.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.5% to about 8% of one or more polyquarterniums, about 0.5% to about 8% of one or more film formers, about 0.25% to about 10% one or more emollients and about 0.5% to about 12% one or more thickening agents. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 1% to about 5% of one or more polyquarterniums, about 1% to about 5% of one or more film formers, about 0.5% to about 8% one or more emollients and about 1% to about 10% one or more thickening agents. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 1.5% to about 3.5% of one or more polyquarterniums, about 1.5% to about 3.5% of one or more film formers, about 1% to about 6% one or more emollients and about 1.5% to about 8.5% one or more thickening agents. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 2% to about 3% of one or more polyquarterniums, about 2% to about 3% of one or more film formers, about 2% to about 5% one or more emollients and about 2.5% to about 6.5% one or more thickening agents. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 2.5% of one or more film formers, about 3.4% one or more emollients and about 4.5% one or more thickening agents.

In aspects of this embodiment, a composition disclosed herein comprises about 16% to about 24% of a cellulose encapsulate and/or of a sol-gel encapsulate comprising about 90% to about 98% of one or more arachnid/insect repellents, about 0.5% to about 8% of one or more polyquarterniums, about 0.5% to about 8% of one or more acrylate copolymers, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a composition disclosed herein comprises about 16% to about 24% of a cellulose encapsulate and/or of a sol-gel encapsulate comprising about 90% to about 98% of one or more arachnid/insect repellents, about 1% to about 5% of one or more polyquarterniums, about 1% to about 5% of one or more acrylate copolymers, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 1.5% to about 3.5% of one or more polyquarterniums, about 1.5% to about 3.5% of one or more acrylate copolymers, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 2% to about 3% of one or more polyquarterniums, about 2% to about 3% of one or more acrylate copolymers, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 2.5% of one or more acrylate copolymers, about 3.5% one or more emollients, about 2% one or more silicone elastomer thickening agents and about 2.5% one or more sodium acrylate-sodium acryloyldimethyl taurate copolymer-based thickening agents.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.5% to about 8% of one or more polyquarterniums, about 0.5% to about 8% of one or more acrylate copolymers, about 0.25% to about 10% one or more emollients, about 0.1% to about 9% one or more silicone elastomer thickening agents and about 0.1% to about 9% one or more sodium acrylate-sodium acryloyldimethyl taurate copolymer-based thickening agents. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 1% to about 5% of one or more polyquarterniums, about 1% to about 5% of one or more acrylate copolymers, about 0.5% to about 8% one or more emollients, about 0.2% to about 7% one or more silicone elastomer thickening agents and about 0.2% to about 7% one or more sodium acrylate-sodium acryloyldimethyl taurate copolymer-based thickening agents. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 1.5% to about 3.5% of one or more polyquarterniums, about 1.5% to about 3.5% of one or more acrylate copolymers, about 1% to about 6% one or more emollients, about 0.25% to about 5% one or more silicone elastomer thickening agents and about 0.5% to about 5% one or more sodium acrylate-sodium acryloyldimethyl taurate copolymer-based thickening agents. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 2% to about 3% of one or more polyquarterniums, about 2% to about 3% of one or more acrylate copolymers, about 2% to about 5% one or more emollients, about 0.5% to about 3.5% one or more silicone elastomer thickening agents and about 1% to about 4% one or more sodium acrylate-sodium acryloyldimethyl taurate copolymer-based thickening agents. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 2.5% of one or more acrylate copolymers, about 3.5% one or more emollients, about 2% one or more silicone elastomer thickening agents and about 2.5% one or more sodium acrylate-sodium acryloyldimethyl taurate copolymer-based thickening agents.

In an embodiment, a composition disclosed herein comprises a cellulose encapsulate and/or of a sol-gel encapsulate comprising one or more arachnid/insect repellents, one or more film formers, and one or more emollients. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein comprises about 16% to about 24% of a cellulose encapsulate and/or of a sol-gel encapsulate comprising about 90% to about 98% of one or more arachnid/insect repellents, about 19% to about 31% of a film former and about 6% to about 18% of one or more emollients. In other aspects of this embodiment, a composition disclosed herein comprises about 16% to about 24% of a cellulose encapsulate and/or of a sol-gel encapsulate comprising about 90% to about 98% of one or more arachnid/insect repellents, about 21% to about 29% of a film former and about 8% to about 16% of one or more emollients. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 22% to about 28% of a film former and about 9% to about 15% of one or more emollients. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 24% to about 26% of a film former and about 11% to about 13% of one or more emollients. In other aspects of this embodiment, a composition disclosed herein comprises about 20% of a cellulose encapsulate and/or of a sol-gel encapsulate comprising about 94% of one or more arachnid/insect repellents, about 25% of a film former and about 12% of one or more emollients.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 19% to about 31% of a film former and about 6% to about 18% of one or more emollients. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 21% to about 29% of a film former and about 8% to about 16% of one or more emollients. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 22% to about 28% of a film former and about 9% to about 15% of one or more emollients. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 24% to about 26% of a film former and about 11% to about 13% of one or more emollients. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 25% of a film former and about 12% of one or more emollients.

In an embodiment, a composition disclosed herein comprises a cellulose encapsulate and/or of a sol-gel encapsulate comprising one or more arachnid/insect repellents, one or more polyquarterniums, and one or more soap bases. In aspects of this embodiment, a composition disclosed herein comprises about 16% to about 24% of a cellulose encapsulate and/or of a sol-gel encapsulate comprising about 90% to about 98% of one or more arachnid/insect repellents, about 0.1% to about 10% of one or more polyquarterniums, and a soap base. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.25% to about 8% of one or more polyquarterniums, and a soap base. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.5% to about 5% of one or more polyquarterniums, and a soap base. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 1% to about 3% of one or more polyquarterniums, and a soap base. In other aspects of this embodiment, a composition disclosed herein comprises about 20% of a cellulose encapsulate and/or of a sol-gel encapsulate comprising about 94% of one or more arachnid/insect repellents, about 2% of one or more polyquarterniums, and a soap base.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, and a soap base. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.25% to about 8% of one or more polyquarterniums, and a soap base. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.5% to about 5% of one or more polyquarterniums, and a soap base. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 1% to about 3% of one or more polyquarterniums, and a soap base. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2% of one or more polyquarterniums, and a soap base.

In aspects of this embodiment, a composition disclosed herein further comprises additional surfactants. In aspects of this embodiment, a composition disclosed herein comprises about 20% to about 50% of additional surfactants. In aspects of this embodiment, additional surfactants include additional cationic surfactants, anionic surfactants, non-ionic surfactants, zwitterionic surfactants, amphoteric surfactants, or any combination thereof.

In an embodiment, a composition disclosed herein comprises a cellulose encapsulate and/or of a sol-gel encapsulate comprising one or more arachnid/insect repellents, one or more polyquarterniums, one or more anionic surfactants, and one or more amphoteric surfactants. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein about 14% to about 26% of a cellulose encapsulate and/or of a sol-gel encapsulate comprising about 88% to about 100% of one or more arachnid/insect repellents, about 0.1% to about 10% of one or more polyquarterniums, about 0.5% to about 15% one or more anionic surfactants, and about 0.1% to about 9% one or more amphoteric surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, about 2% to about 12% one or more anionic surfactants, and about 0.25% to about 7% one or more amphoteric surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, about 4% to about 10% one or more anionic surfactants, and about 0.5% to about 5% one or more amphoteric surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, about 6% to about 8% one or more anionic surfactants, and about 2% to about 4% one or more amphoteric surfactants. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 7% one or more anionic surfactants, and about 3% one or more amphoteric surfactants.

In aspects of this embodiment, a composition disclosed herein about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, about 0.5% to about 15% one or more anionic surfactants, and about 0.1% to about 9% one or more amphoteric surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.2% to about 8% of one or more polyquarterniums, about 2% to about 12% one or more anionic surfactants, and about 0.25% to about 7% one or more amphoteric surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, about 4% to about 10% one or more anionic surfactants, and about 0.5% to about 5% one or more amphoteric surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, about 6% to about 8% one or more anionic surfactants, and about 2% to about 4% one or more amphoteric surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 7% one or more anionic surfactants, and about 3% one or more amphoteric surfactants.

In an embodiment, a composition disclosed herein comprises a cellulose encapsulate and/or of a sol-gel encapsulate comprising one or more arachnid/insect repellents, one or more polyquarterniums, one or more sulfate surfactants, and one or more betaine surfactants. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein about 14% to about 26% of a cellulose encapsulate and/or of a sol-gel encapsulate comprising about 88% to about 100% of one or more arachnid/insect repellents, about 0.1% to about 10% of one or more polyquarterniums, about 0.5% to about 15% one or more sulfate surfactants, and about 0.1% to about 9% one or more betaine surfactants. In other aspects of this embodiment, a composition disclosed herein comprises about 16% to about 24% of a cellulose encapsulate and/or of a sol-gel encapsulate comprising about 90% to about 98% of one or more arachnid/insect repellents, about 0.2% to about 8% of one or more polyquarterniums, about 2% to about 12% one or more sulfate surfactants, and about 0.25% to about 7% one or more betaine surfactants. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 0.4% to about 6% of one or more polyquarterniums, about 4% to about 10% one or more sulfate surfactants, and about 0.5% to about 5% one or more betaine surfactants. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 0.6% to about 5% of one or more polyquarterniums, about 6% to about 8% one or more sulfate surfactants, and about 2% to about 4% one or more betaine surfactants. In other aspects of this embodiment, a composition disclosed herein comprises about 20% of a cellulose encapsulate and/or of a sol-gel encapsulate comprising about 94% of one or more arachnid/insect repellents, about 2.5% of one or more polyquarterniums, about 7% one or more sulfate surfactants, and about 3% one or more betaine surfactants.

In an embodiment, a composition disclosed herein comprises a cellulose encapsulate and/or of a sol-gel encapsulate comprising one or more arachnid/insect repellents, one or more polyquarterniums, one or more sulfate surfactants, and one or more betaine surfactants. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein about 14% to about 26% of a cellulose encapsulate and/or of a sol-gel encapsulate comprising about 40% to about 50% of a first arachnid/insect repellent and about 40% to about 50% of a second arachnid/insect repellent, about 0.1% to about 10% of one or more polyquarterniums, about 0.5% to about 15% one or more sulfate surfactants, and about 0.1% to about 9% one or more betaine surfactants. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 0.2% to about 8% of one or more polyquarterniums, about 2% to about 12% one or more sulfate surfactants, and about 0.25% to about 7% one or more betaine surfactants. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 0.4% to about 6% of one or more polyquarterniums, about 4% to about 10% one or more sulfate surfactants, and about 0.5% to about 5% one or more betaine surfactants. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 0.6% to about 5% of one or more polyquarterniums, about 6% to about 8% one or more sulfate surfactants, and about 2% to about 4% one or more betaine surfactants. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 2.5% of one or more polyquarterniums, about 7% one or more sulfate surfactants, and about 3% one or more betaine surfactants.

In an embodiment, a composition disclosed herein comprises a cellulose encapsulate and/or of a sol-gel encapsulate comprising one or more arachnid/insect repellents, one or more polymers, one or more film formers and one or more fragrances. In other aspects of this embodiment, a composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product. In other aspects of this embodiment, an arachnid/insect repellent comprises DEET, IR3535, lemon *eucalyptus* oil, *eucalyptus* oil, peppermint oil, *geranium* oil and clove oil.

In aspects of this embodiment, a composition disclosed herein comprises about 14% to about 26% of a cellulose encapsulate and/or of a sol-gel encapsulate comprising about 88% to about 100% of one or more arachnid/insect repellents, about 1% to about 10% of one or more polymers, about 0.25% to about 8% of one or more film formers and about 0.25% to about 8% one or more fragrances. In other aspects of this embodiment, a composition disclosed herein comprises about 16% to about 24% of a cellulose encapsulate and/or of a sol-gel encapsulate comprising about 90% to about 98% of one or more arachnid/insect repellents, about 3% to about 9% of one or more polymers, about 0.5% to about 6% of one or more film formers and about 0.5% to about 6% one or more fragrances. In yet other aspects of this embodiment, a composition disclosed herein comprises about 17% to about 23% of a cellulose encapsulate and/or of a sol-gel encapsulate comprising about 91% to about 97% of one or more arachnid/insect repellents, about 4% to about 8% of one or more polymers, about 1% to about 5% of one or more film formers and about 1% to about 5% one or more fragrances. In still other aspects of this embodiment, a composition disclosed herein comprises about 19% to about 21% of a cellulose encapsulate and/or of a sol-gel encapsulate comprising about 93% to about 95% of one or more arachnid/insect repellents, about 5% to about 7% of one or more polymers, about 2% to about 4% of one or more film formers and about 2% to about 4% one or more fragrances. In other aspects of this embodiment, a composition disclosed herein comprises about 20% of a cellulose encapsulate and/or of a sol-gel encapsulate comprising about 94% of one or more arachnid/insect repellents, about 6% of one or more polymers, about 3% of one or more film formers and about 3% one or more fragrances.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 1% to about 10% of one or more polymers, about 0.25% to about 8% of one or more film formers and about 0.25% to about 8% one or more fragrances. In other aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 3% to about 9% of one or more polymers, about 0.5% to about 6% of one or more film formers and about 0.5% to about 6% one or more fragrances. In yet other aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 4% to about 8% of one or more polymers, about 1% to about 5% of one or more film formers and about 1% to about 5% one or more fragrances. In still other aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 5% to about 7% of one or more polymers, about 2% to about 4% of one or more film formers and about 2% to about 4% one or more fragrances. In other aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 6% of one or more polymers, about 3% of one or more film formers and about 3% one or more fragrances.

In aspects of this embodiment, a composition disclosed herein comprises about 16% to about 24% of a cellulose encapsulate and/or of a sol-gel encapsulate comprising about 90% to about 98% of one or more arachnid/insect repellents, about 14% to about 26% one or more plant oils, about 1% to 10% of a polymer, about 0.25% to about 8% of a film former and about 0.1% to about 6% fragrance. In aspects of this embodiment, a composition disclosed herein comprises about 16% to about 24% of a cellulose encapsulate and/or of a sol-gel encapsulate comprising about 90% to about 98% of one or more arachnid/insect repellents, about 16% to about 24% one or more plant oils, about 3% to 9% of a polymer, about 0.5% to about 6% of a film former and about 0.2% to about 5% fragrance. In aspects of this embodiment, a composition disclosed herein comprises about 17% to about 23% of a cellulose encapsulate and/or of a sol-gel encapsulate comprising about 91% to about 97% of one or more arachnid/insect repellents, about 17% to about 23% one or more plant oils, about 4% to 8% of a polymer, about 1% to about 5% of a film former and about 0.3% to about 4% fragrance. In aspects of this embodiment, a composition disclosed herein comprises about 19% to about 21% of a cellulose encapsulate and/or of a sol-gel encapsulate comprising about 93% to about 95% of one or more arachnid/insect repellents, about 19% to about 21% one or more plant oils, about 5% to 7% of a polymer, about 2% to about 4% of a film former and about 0.5% to about 2% fragrance. In aspects of this embodiment, a composition disclosed herein comprises about 20% of a cellulose encapsulate and/or of a sol-gel encapsulate comprising about 94% of one or more arachnid/insect repellents, about 20% one or more plant oils, about 6% of a polymer, about 3% of a film former and about 1% fragrance.

In aspects of this embodiment, a composition disclosed herein comprises about 14% to about 26% of a cellulose encapsulate and/or of a sol-gel encapsulate comprising about 40% to about 50% of a first arachnid/insect repellent and about 40% to about 50% of a second arachnid/insect repellent, about 14% to about 26% one or more plant oils, about 1% to 10% of a polymer, about 0.25% to about 8% of a film former and about 0.1% to about 6% fragrance. In aspects of this embodiment, a composition disclosed herein comprises about 16% to about 24% of a cellulose encapsulate and/or of a sol-gel encapsulate comprising about 42% to about 50% of a first arachnid/insect repellent and about 42% to about 50% of a second arachnid/insect repellent, about 16% to about 24% one or more plant oils, about 3% to 9% of a polymer, about 0.5% to about 6% of a film former and about 0.2% to about 5% fragrance. In aspects of this embodiment, a composition disclosed herein comprises about 17% to about 23% of a cellulose encapsulate and/or of a sol-gel encapsulate comprising about 44% to about 49% of a first arachnid/insect repellent and about 44% to about 49% of a second arachnid/insect repellent, about 17% to about 23% one or more plant oils, about 4% to 8% of a polymer, about 1% to about 5% of a film former and about 0.3% to about 4% fragrance. In aspects of this embodiment, a composition disclosed herein comprises about 19% to about 21% of a cellulose encapsulate and/or of a sol-gel encapsulate comprising about 46% to about 48% of a first arachnid/insect repellent and about 46% to about 48% of a second arachnid/insect repellent, about 19% to about 21% one or more plant oils, about 5% to 7% of a polymer, about 2% to about 4% of a film former and about 0.5% to about 2% fragrance. In aspects of this embodiment, a composition disclosed herein comprises about 20% of a cellulose encapsulate and/or of a sol-gel encapsulate comprising about 47% of a first arachnid/insect repellent and about 47% of a second arachnid/insect repellent, about 20% one or more plant oils, about 6% of a polymer, about 3% of a film former and about 1% fragrance.

In an embodiment, application of a composition disclosed herein can occur during washing in a suitable or effective amount, with application over part or the whole body. A shampoo or conditioner, gel, soap, hand sanitizer, cream, may be applied to hair, though in an embodiment, the shampoo combination product may be rinsed over part or the whole body, with a composition adhering to the skin and hair. A selected amount of a combination product may be applied directly to the skin, for instance, without limitation, a lotion, spray or bodywash or may be used through intermediate application to a washcloth, pad, sponge, or other applicator. After lathering, dirt and sloughed-off skin may be washed away by rinsing with water leaving behind one or more of the active agents, and in an embodiment, without limitation, an active agent encapsulated in a cellulose derived capsule.

A composition disclosed herein is also useful in the treatment of a skin condition. A skin condition includes, without limitation, Seborrheic dermatitis, eczema, xerosis, infestation, dyschromia, keratosis pilaris, acne, anti-aging, sensitive skin, ephilidies, solar lentigines, photo sensitive disease, skin cancer, melisma, autoimmune disorder, alopecia, fungal, bacterial, and viral infections, protect colored or treated hair, bromhidrosis, malodor, dandruff, wound healing, arachnid/insect repellent, pet shampoo/skin care, lindane or similar conditions.

In an embodiment, composition that is encapsulated in a cellulose derived capsule and/or a sol-gel capsule are used in paints. In a further embodiment, a paint including an encapsulated composition includes one or more additional agents, including, without limitation, HALS.

In an embodiment, a composition that is encapsulated in a cellulose derived capsule and/or a sol-gel capsule are used in products used by the military, police or other governmental or non-governmental force. In an embodiment, a product used by the by the military, police or other governmental or non-governmental force includes, without limitation, sunscreen, paint, clothes, weapons, including, without limitation, weapons containing composite or other synthetic parts, and other by the military, police or other governmental or non-governmental force products. In an embodiment, a composition that is encapsulated in a cellulose derived capsule and/or a sol-gel capsule used for by the military, police or other governmental or non-governmental force includes a reflective agent and/or an agent capable of preventing the detection of infrared radiation by an individual or equipment.

A composition disclosed herein can be applied once per day, applied two, three, four or more times per day, applied every other day or applied about 10, 8, 7, 6, 5, 4, 3, 2 or 1 time per week. In aspects of this embodiment, the present invention discloses that a composition can be applied to wet skin and/or hair or applied to dry skin and/or hair.

Aspects of the present specification can also be described as follows:

1. A composition comprising one or more flexible encapsulates comprising one or more arachnid/insect repellents.
2. The composition of claim 1, wherein the one or more flexible encapsulates are in an amount of 8% to about 20%, about 10% to about 18%, about 11% to about 17%, about 13% to about 15% or about 14% by weight of the total composition
3. The composition of claim 1, wherein the one or more flexible encapsulates are in an amount of about 14% to about 26%, about 16% to about 24%, about 17% to about 23%, about 19% to about 21% or about 20% by weight of the total composition
4. The composition of claim 1, wherein the one or more flexible encapsulates are in an amount of about 2% to about 40%, about 3% to about 38%, about 4% to about 36%, about 5% to about 36%, about 6% to about 34%, about 8% to about 32%, about 10% to about 30%, about 12% to about 28%, about 14% to about 26%, about 16% to about 24%, or about 18% to about 22%, by weight of the total composition
5. The composition of any one of claims 1-4, wherein the one or more flexible encapsulates comprises a first arachnid/insect repellent and a second arachnid/insect repellent.
6. The composition of claim 5, wherein the first arachnid/insect repellent is encapsulated in a first encapsulate and the second arachnid/insect repellent is encapsulated in a second encapsulate.
7. The composition of claim 5, wherein the first arachnid/insect repellent and the second arachnid/insect repellent are encapsulated in the same encapsulate.
8. The composition of any one of claims 5-7, wherein the first arachnid/insect repellent is in an amount of about 1% to about 5% and the second arachnid/insect repellent is in an amount of about 95% to about 99%, or wherein the first arachnid/insect repellent is in an amount of about 6% to about 10% and the second arachnid/insect repellent is in an amount of about 90% to about 94%, or wherein the first arachnid/insect repellent is in an amount of about 11% to about 15% and the second arachnid/insect repellent is in an amount of about 85% to about 89%, or wherein the first arachnid/insect repellent is in an amount of about 16% to about 20% and the second arachnid/insect repellent is in an amount of about 80% to about 84%, or wherein the first arachnid/insect repellent is in an amount of about 21% to about 25% and the second arachnid/insect repellent is in an amount of about 75% to about 79%, or wherein the first arachnid/insect repellent is in an amount of about 26% to about 30% and the second arachnid/insect repellent is in an amount of about 70% to about 74%, or wherein the first arachnid/insect repellent is in an amount of about 31% to about 35% and the second arachnid/insect repellent is in an amount of about 65% to about 69%, or wherein the first arachnid/insect repellent is in an amount of about 36% to about 40% and the second arachnid/insect repellent is in an amount of about 60% to about 64%, or wherein the first arachnid/insect repellent is in an amount of about 41% to about 45% and the second arachnid/insect repellent is in an amount of about 55% to about 59%, or wherein the first arachnid/insect repellent is in an amount of about 46% to about 50% and the second arachnid/insect repellent is in an amount of about 50% to about 54%.
9. The composition of any one of claims 1-8, wherein the one or more flexible encapsulates comprise one or more flexible cellulose derived encapsulates, one or more sol-gel encapsulates, or a combination of both.
10. The composition of any one of claims 1-9, further comprising one or more arachnid/insect repellents not encapsulated.
11. The composition of any one of claims 1-10, wherein the one or more arachnid/insect repellents include one or more synthetic chemical compounds or one or more naturally-occurring compounds.
12. The composition of claim 11, wherein the one or more synthetic chemical compounds include N,N-Diethyl-m-toluamide (DEET), dimethyl phthalate, ethyl hexanediol, indalone, di-n-propylisocinchoronate, bicycloheptene, dicarboximide, dimethyl carbate, dimethyl phthalate, metofluthrin, indalone, permethrin, icaridin, nepetalactone, tetrahydrofuraldehyde ethyl butylacetylaminopropionate (IR-3535), p-menthane-3,8-diol (PMD), tricyclodecenyl allyl ether, ethylhexanediol, SS220 ((1S,2'S)-Methylpiperidinyl-3-cyclohexen-1-carboxamide), hydroxyethyl isobutyl piperidine carboxylate, an anthranilate-based arachnid/insect repellent, a plant oil, or any combination thereof.
13. The composition of claim 11, wherein the anthranilate-based arachnid/insect repellent includes methyl anthranilate, N,N-dimethylanthranilic acid (DMA), ethyl anthranilate (EA), butyl anthranilate (BA), or.
14. The composition of claim 11, wherein the one or more naturally-occurring compounds include compounds purified from a plant-derived material or sea-life.
15. The composition of claim 11, wherein the plant-derived material is a plant oil.
16. The composition of claim 12 or 15, wherein the plant oil includes an acyclic monoterpene alcohol or aldehyde, a benzenoid aromatic compound containing at least one oxygenated substituent or side chain, a monocarbocyclic terpene generally having a six membered ring bearing one or more oxygenated substituents, or any combination thereof.
17. The composition of claim 12, 15 or 16, wherein the plant oil includes an α- or β-pinene; α-campholenic aldehyde; α-citronellol; α-iso-amyl-cinnamic; α-pinene oxide; α-cinnamic terpinene; α-terpineol (e.g., 1-methyl-4-isopropyl-1-cyclohexen-8-ol); α-terpinene; λ-terpinene; aldehyde C16 (pure); α-phellandrene; amyl cinnamic aldehyde; amyl salicylate; anethole; anisic aldehyde; benzyl acetate; benzyl alcohol; borneol; callicarpenal; carvacrol; carveol; cineole; cinnamaldehyde; cinnamic alcohol; cis-pinane; citral (e.g., 3,7-dimethyl-2,6-octadienal); citronella; citronellal; citronellol, citronellol dextro (e.g., 3-7-dimethyl-6-octen-1-ol); citronellol; citronellyl acetate; citronellyl nitrile; d-dihydrocarvone; decyl aldehyde; diethyl phthalate; dihydroanethole; dihydrocarveol; dihydrolinalool; dihydromyrcene; dihydromyrcenol; dihydromyrcenyl acetate; dihydroterpineol; dimethyl salicylate; dimethyloctanal; dimethyloctanol; dimethyloctanyl acetate; diphenyl oxide; dipropylene glycol; d-limonene; d-pulegone; estragole; ethyl vanillin, 3-ethoxy-4-hydrobenzaldehyde; p-menthane-3,8-diol; eucalyptol (e.g., cineole); *eucalyptus citriodora; eucalyptus globulus*; eugenol (e.g., 2-methoxy-4-allyl phenol); fenchol; ferniol; florazon (e.g., 4-ethyl-α, α-dimethyl-benzenepropanal); galaxolide; geraniol (e.g., 2-trans-3,7-dimethyl-2, 6-octadien-8-ol); geranyl acetate; geranyl nitrile; guaiacol; heliotropin; herbanate (e.g., 3-(1-methyl-ethyl) bicyclo(2,2,1) hept-5-ene-2-carboxylic acid ethyl ester); hydroxycitronellal; i-carvone; i-methyl acetate; ionone; isobutyl quinoleine (e.g., 6-secondary butyl quinoline); isobornyl acetate; isobornyl methylether; isoeugenol; isolongifolene; lavandin; limonene; linalool oxide; linalool; linalool; linalyl acetate; I-methyl acetate; longifolene; mandarin; *mentha*; menthane hydroperoxide; menthol crystals; menthol laevo (e.g., 5-methyl-2-isopropyl cyclohexanol); menthol; menthone laevo (e.g., 4-isopropyl-1-methyl cyclohexan-3-one); methyl anthranilate; methyl cedryl ketone; methyl chavicol; methyl hexyl ether; methyl ionone; methyl salicylate, mineral; musk ambrette; musk ketone; musk xylol; allylisothio-cyanate); myrcene; nerol; neryl acetate; nonyl aldehyde; *myristica fragrans*; para-cymene; para-hydroxy phenyl butanone crystals (e.g., 4-(4-hydroxyphenyl)-2-butanone); passion palmarosa oil; p-cymene; pennyroyal oil; perillaldehyde; petitgrain; phenyl ethyl alcohol (e.g., 1-phenyl ethyl alcohol and 2-phenyl ethyl alcohol); phenyl ethyl propionate (e.g., 1-phenyl ethyl propionate and 2-phenyl ethyl propionate); phenyl ethyl-2-methylbutyrate; pinane hydroperoxide; pinanol; pine ester; pinene; piperonal; piperonyl acetate; piperonyl alcohol; plinol; plinyl acetate; pseudo ionone; pyrethrum; rhodinol; rhodinyl acetate; rosalinsandenol; spirantol; terpinen-4-ol, terpenoid; terpineol; terpinolene; terpinyl acetate; tert-butylcyclohexyl acetate; tetrahydrolinalool; tetrahydrolinalyl acetate; tetrahydromyrcenol; thymol; trans-2-hexenol; trans-anethole and metabolites thereof; turpentine; vanillin (e.g., 4-hydroxy-3-methoxy benzaldehyde); vetiver; vitalizair; and the like.

18. The composition of any one of claims 1-17, wherein the composition is a body wash, a shampoo, an after shower body lotion, a conditioner, a soap, a gel, a hand sanitizer, a cream, a spray, a mouse, a lotion, an ointment, a make-up product, a lip balm, a hair spray product, an arachnid/insect repellent or a medicinal product.

19. The composition of any one of claims 1-18, further comprising one or more polyquarterniums, one or more surfactants, one or more film formers, one or more emollients, one or more thickening agents, one or more soap bases, one or more polymers, one or more fragrances, or any combination thereof.

20. The composition of claim 19, wherein the one or more polyquarterniums are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

21. The composition of claim 19 or 20, wherein the one or more polyquarterniums are in an amount of about 0.1% to about 10%, about 0.2% to about 8%, about 0.4% to about 6%, about 0.6% to about 5%, about 2.5% by weight of the total composition.

22. The composition of claim 19 or 20, wherein the one or more polyquarterniums are in an amount of about 0.1% to about 10%, about 0.25% to about 8%, about 0.5% to about 5%, about 1% to about 3% or about 2% by weight of the total composition.

23. The composition of claim 19 or 20, wherein the one or more polyquarterniums are in an amount of about 0.1% to about 7%, about 0.1% to about 5%, about 0.1% to about 3%, about 0.25% to about 2.5% or about 0.5% by weight of the total composition.

24. The composition of any one of claims 19-23, wherein the one or more polyquarterniums include polyquarternium-1, polyquarternium-2, polyquarternium-4 (CELQUAT L-200), polyquarternium-5, polyquarternium-6, polyquarternium-7, polyquarternium-10, polyquarternium-11, polyquarternium-15, polyquarternium-16, polyquarternium-22, polyquarternium-28, polyquarternium-32, polyquarternium-37, polyquarternium-39, polyquarternium-40, polyquarternium-41, polyquarternium-42, polyquarternium-44, polyquarternium-45, polyquarternium-46, polyquarternium-47, polyquarternium-64 or any combination thereof.

25. The composition of any one of claims 19-24, wherein the one or more surfactants are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

26. The composition of any one of claims 19-25, wherein the one or more surfactant are present in an amount of about 0.1% to about 10%, about 0.25% to about 8%, about 0.5% to about 5%, about 1% to about 3%, about 1.6% by weight of the total composition.

27. The composition of any one of claims 19-25, wherein the one or more surfactant are present in an amount of about 3% to about 17%, about 5% to about 15%, about 7% to about 13%, about 9% to about 11% or about 10% by weight of the total composition.

28. The composition of any one of claims 19-25, wherein the one or more surfactant are present in an amount of about 2% to about 18%, about 3% to about 15%, about 4% to about 13%, about 5% to about 12% or about 6% to about 11% by weight of the total composition.

29. The composition of any one of claims 19-25, wherein the one or more surfactant are present in an amount of about 1% to about 20%, about 4% to about 14%, about 7% to about 11%, about 8% to about 10% or about 8.8% by weight of the total composition.

30. The composition of any one of claims 19-29, wherein the one or more surfactants include one or more cationic surfactants, one or more anionic surfactants, one or more non-ionic surfactants, one or more zwitterionic surfactants, one or more amphoteric surfactants, or any combination thereof 31. The composition of any one of claims 19-30, wherein the one or more surfactants include one or more anionic surfactants present in an amount of about 0.5% to about 15%, about 2% to about 12%, about 4% to about 10%, about 6% to about 8% or about 7% by weight of the total composition.

32. The composition of any one of claims 19-30, wherein the one or more surfactants include one or more anionic surfactants present in an amount of about 1% to about 16%, about 1% to about 12%, about 3% to about 9%, about 5% to about 7% or about 5.6% by weight of the total composition.

33. The composition of any one of claims 30-32, wherein the one or more anionic surfactants include one or more sulfated monoglyceride surfactants, one or more olefin sulfonate surfactants, one or more alkylbenzene sulfonate surfactants, one or more alkane sulfonate surfactants, one or more alkyl sulfosuccinate surfactants, one or more acyl isethionate surfactants or any combination thereof.

34. The composition of claim 33, wherein the one or more alkyl sulfosuccinate surfactants include disodium N-octadecylsulfosuccinamate, diammonium lauryl sulfosuccinate, disodium laureth sulfosuccinate, tetrasodium N-(1, 2-dicarboxyethyl)-N-octadecylsulfosuccinate, diamyl ester of sodium sulfosuccinic acid, dihexyl ester of sodium sulfosuccinic acid and dioctyl esters of sodium sulfosuccinic acid; sodium dodecyl sulfate (or sodium lauryl sulfate), sodium laureth sulfate, ammonium lauryl sulfate, or any combination thereof.

35. The composition of claim 33, wherein the one or more acyl isethionate surfactants include an alkylglyceryl ether sulfonate, a sodium cocoglyceryl ether sulfonate, a sulfonated fatty acid, a sulfonated methyl ester, an acyl glutamate, an alkanoyl sarcosinate, an alkyl ether carboxylate, an acyl lactylate, a carboxylate, a saponified soap, or any combination thereof.

36. The composition of claim 33, wherein the one or more acyl isethionate surfactants ammonium cocoyl isethionate, sodium cocoyl isethionate, sodium lauroyl isethionate, sodium lauroyl sarcosinate, lauroyl sarcosine, sodium cocoyl sarcosinate, ammonium lauroyl sarcosinate, sodium laureth carboxylate, sodium cocoyl lactylate, sodium lauroyl carboxylate, sodium cocoyl carboxylate, ammonium lauroyl carboxylate, sodium laurate, sodium myristate, sodium palmitate, sodium stearate, sodium tallowate, cocoate or any combination thereof.

37. The composition of any one of claims 19-36, wherein the one or more surfactants include one or more amphoteric surfactants present in an amount of about 0.1% to about 9%, about 0.25% to about 7%, about 0.5% to about 5%, about 2% to about 4%, about 3% by weight of the total composition.

38. The composition of any one of claims 19-36, wherein the one or more surfactants include one or more amphoteric surfactants present in an amount of about 0.1% to about 5%, about 0.25% to about 4%, about 0.5% to about 3%, about 0.75% to about 2.5% or about 1% to about 2% by weight of the total composition.

39. The composition of any one of claims 19-36, wherein the one or more surfactants include one or more amphoteric surfactants present in an amount of about 0.1% to about 10%, about 0.25% to about 8%, about 0.5% to about 5%, about 1% to about 3% or about 1.6% by weight of the total composition.

40. The composition of any one of claims 37-39, wherein the one or more amphoteric surfactants include one or more betaines, one or more sultaines, one or more hydroxysultaines, one or more alkyliminoacetates, one or more iminodialkanoates, one or more aminoalkanoates or any combination thereof.

41. The composition of any one of claims 37-39, wherein the one or more betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, oleyl dimethyl gamma-carboxypropyl betaine, lauryl bis-(2-hydroxypropyl)alphacarboxyethyl betaine, coco dimethyl sulfopropyl betaine, lauryl dimethyl sulfoethyl betaine, lauryl bis-(2-hydroxyethyl) sulfopropyl betaine, oleyl betaine, cocamidopropyl betaine, an amidobetaine, an amidosulfobetaine or any combination thereof.

42. The composition of any one of claims 19-41, wherein the one or more surfactants include one or more acyl taurate surfactants present in an amount of about 0.1% to about 5%, about 0.25% to about 4%, about 0.5% to about 3%, about 0.75% to about 2.5% or about 1% to about 2% by weight of the total composition.

43. The composition of embodiment 42, wherein the one or more acyl taurate surfactants include sodium methyl cocoyl taurate and sodium methyl oleoyl taurate, taurine, a N-alkyltaurine or any combination thereof.

44. The composition of any one of claims 19-43, wherein the one or more film formers are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25%, at least 30%, at least 35% or at least 40% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25%, at most 30%, at most 35% or at most 40% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19%, about 5.0% to about 20%, about 5.0% to about 25%, about 5.0% to about 30%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35% or about 20% to about 40% of the total weight of the composition.

45. The composition of any one of claims 19-44, wherein the one or more film formers are present in an amount of about 1% to about 6%, about 1.5% to about 4.5%, about 2% to about 4%, about 2.5% to about 3.5%, about 3% or about 2.5% by weight of the total composition.

46. The composition of any one of claims 19-44, wherein the one or more film formers are present in an amount of about 0.25% to about 8%, about 0.5% to about 6%, about 1% to about 5%, about 2% to about 4% or about 3% by weight of the total composition.

47. The composition of any one of claims 19-44, wherein the one or more film formers are present in an amount of about 19% to about 31%, about 21% to about 29%, about 22% to about 28%, about 24% to about 26% or about 25% by weight of the total composition.

48. The composition of any one of claims 19-47, wherein the one or more film formers include petroleum, an acrylate copolymer, a synthetic wax of branched polyalpha olefin polymers, a $C_{28}$-$C_{52}$ olefin/undecylenic acid copolymer 49. The composition of any one of claims 19-48, wherein the one or more film formers comprising, consisting essentially of or consisting of petrolatum, dimethicone, stearamidopropyl dimethylamine, stearate and tocopheryl acetate.

50. The composition of any one of claims 19-49, wherein the one or more emollients are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 5.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

51. The composition of any one of claims 19-50, wherein the one or more emollients are in an amount of about 0.25% to about 10%, about 0.5% to about 8%, about 1% to about 6%, about 2% to about 5%, or about 3.5% of the total weight of the composition.

52. The composition of any one of claims 19-50, wherein the one or more emollients are in an amount of about 6% to about 18%, about 8% to about 16%, about 9% to about 15%, about 11% to about 13%, or about 12% of the total weight of the composition.

53. The composition of any one of claims 19-52, wherein the one or more emollients comprise capryllic capric triglyceride.

54. The composition of any one of claims 19-53, wherein the one or more thickening agents are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

55. The composition of any one of claims 19-54, wherein the one or more thickening agents are in an amount of about 0.5% to about 12%, about 1% to about 10%, about 1.5% to about 8.5%, about 2.5% to about 6.5%, or about 4.5% of the total weight of the composition.

56. The composition of any one of claims 19-55, wherein the one or more thickening agents include one or more silicone elastomer thickening agents and one or more sodium acrylate-sodium acryloyldimethyl taurate copolymer-based thickening agents.

57. The composition of claim 56, wherein one or more silicone elastomer thickening agents are in an amount of about 0.1% to about 9%, about 0.2% to about 7%, about 0.25% to about 5%, about 0.5% to about 3.5%, or about 2% of the total weight of the composition.

58. The composition of claim 56 or 57, wherein the one or more silicone elastomer thickening agents include a dimethicone-vinyldimethyl trimethylsiloxysilicate-dimethicone crosspolymer.

59. The composition of any one of claims 56-58, wherein one or more sodium acrylate-sodium acryloyldimethyl taurate copolymer-based thickening agents are in an amount of about 0.1% to about 9%, about 0.2% to about 7%, about 0.5% to about 5%, about 1% to about 4%, or about 2.5% of the total weight of the composition.

60. The composition of any one of claims 56-59, wherein the one or more sodium acrylate-sodium acryloyldimethyl taurate copolymer-based thickening agents include an acrylate-sodium acryloyldimethyl taurate copolymer-based thickening agent comprising isohexadecane and polysorbate 80.

61. The composition of any one of claims 19-60, wherein the one or more polymers are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, at least 10%, at least 11%, at least 12%, at least 13%, at least 14%, at least 15%, at least 20%, at least 25% of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10%, at most 11%, at most 12%, at most 13%, at most 14%, at most 15%, at most 20%, at most 25% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 1.0% to about 11%, about 1.0% to about 12%, about 1.0% to about 13%, about 1.0% to about 14%, about 1.0% to about 15%, about 1.0% to about 16%, about 1.0% to about 17%, about 1.0% to about 18%, about 1.0% to about 19%, about 1.0% to about 20%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 2.0% to about 11%, about 2.0% to about 12%, about 2.0% to about 13%, about 2.0% to about 14%, about 2.0% to about 15%, about 2.0% to about 16%, about 2.0% to about 17%, about 2.0% to about 18%, about 2.0% to about 19%, about 2.0% to about 20%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 3.0% to about 11%, about 3.0% to about 12%, about 3.0% to about 13%, about 3.0% to about 14%, about 3.0% to about 15%, about 3.0% to about 16%, about 3.0% to about 17%, about 3.0% to about 18%, about 3.0% to about 19%, about 3.0% to about 20%, about 4.0% to about 5.0%, about 4.0% to about 6.0%, about 4.0% to about 7.0%, about 4.0% to about 8.0%, about 4.0% to about 9.0%, about 4.0% to about 10%, about 4.0% to about 11%, about 4.0% to about 12%, about 4.0% to about 13%, about 4.0% to about 14%, about 4.0% to about 15%, about 4.0% to about 16%, about 4.0% to about 17%, about 4.0% to about 18%, about 4.0% to about 19%, about 4.0% to about 20%, about 5.0% to about 6.0%, about 5.0% to about 7.0%, about 5.0% to about 8.0%, about 5.0% to about 9.0%, about 5.0% to about 10%, about 5.0% to about 11%, about 5.0% to about 12%, about 4.0% to about 13%, about 5.0% to about 14%, about 5.0% to about 15%, about 5.0% to about 16%, about 5.0% to about 17%, about 5.0% to about 18%, about 5.0% to about 19% or about 5.0% to about 20% of the total weight of the composition.

62. The composition of any one of claims 19-61, wherein the one or more polymers are present in an amount of about 1% to about 10%, about 3% to about 9%, about 4% to about 8%, about 5% to about 7% or about 6% by weight of the total composition.

63. The composition of any one of claims 19-62, wherein the one or more fragrances are in an amount of at least 0.1%, at least 0.2%, at least 0.3%, at least 0.4%, at least 0.5%, at least 0.6%, at least 0.7%, at least 0.8%, at least 0.9%, at least 1.0%, at least 2.0%, at least 3.0%, at least 4.0%, at least 5.0%, at least 6.0%, at least 7.0%, at least 8.0%, at least 9.0%, or at least 10 of the total weight of the composition, or at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, or at most 10% of the total weight of the composition, or about 0.1% to about 0.5%, about 0.1% to about 1.0%, about 0.1% to about 2.0%, about 0.1% to about 3.0%, about 0.1% to about 4.0%, about 0.1% to about 5.0%, about 0.1% to about 6.0%, about 0.1% to about 7.0%, about 0.1% to about 8.0%, about 0.1% to about 9.0%, about 0.1% to about 10%, about 0.5% to about 1.0%, about 0.5% to about 2.0%, about 0.5% to about 3.0%, about 0.5% to about 4.0%, about 0.5% to about 5.0%, about 0.5% to about 6.0%, about 0.5% to about 7.0%, about 0.5% to about 8.0%, about 0.5% to about 9.0%, about 0.5% to about 10%, about 1.0% to about 2.0%, about 1.0% to about 3.0%, about 1.0% to about 4.0%, about 1.0% to about 5.0%, about 1.0% to about 6.0%, about 1.0% to about 7.0%, about 1.0% to about 8.0%, about 1.0% to about 9.0%, about 1.0% to about 10%, about 2.0% to about 3.0%, about 2.0% to about 4.0%, about 2.0% to about 5.0%, about 2.0% to about 6.0%, about 2.0% to about 7.0%, about 2.0% to about 8.0%, about 2.0% to about 9.0%, about 2.0% to about 10%, about 3.0% to about 4.0%, about 3.0% to about 5.0%, about 3.0% to about 6.0%, about 3.0% to about 7.0%, about 3.0% to about 8.0%, about 3.0% to about 9.0%, about 3.0% to about 10%, about 4.0% to about 5.0%, about 4.0% to about 6.0%, about 4.0% to about 7.0%, about 4.0% to about 8.0%, about 4.0% to about 9.0%, about 4.0% to about 10%, about 5.0% to about 6.0%, about 5.0% to about 7.0%, about 5.0% to about 8.0%, about 5.0% to about 9.0%, about 5.0% to about 10%, about 6.0% to about 7.0%, about 6.0% to about 8.0%, about 6.0% to about 9.0%, about 6.0% to about 10%, %, about 7.0% to about 8.0%, about 7.0% to about 9.0%, about 7.0% to about 10%, about 8.0% to about 9.0%, about 8.0% to about 10%, about 9.0% to about 10%, of the total weight of the composition.

64. The composition of any one of claims 19-61, wherein the one or more fragrances are present in an amount of about 0.25% to about 8%, about 0.5% to about 6%, about 1% to about 5%, about 2% to about 4% or about 3% by weight of the total composition.

65. The composition of any one of claims 19-61, wherein the one or more fragrances are present in an amount of about 0.1% to about 6%, about 0.2% to about 5%, about 0.3% to about 4%, about 0.5% to about 2% or about 1% by weight of the total composition.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compositions disclosed herein, and the methods or uses pertaining to the disclosed compositions.

Example 1: SPF Testing of Sunscreen Body Wash Compositions

Sunscreen body wash compositions disclosed herein were tested to determine their SPF value using the static, rinse/lather/rinse/rub and/or water immersion (40 or 80 minute) assays using the methods described in FDA Final Monograph, "Labelling and Effectiveness Testing; Sunscreen Drug Products for Over-the Counter Human Use", Final Rule, 21 C.F.R. §§ 201 and 310. To conduct this test, a 50 cm$^2$ square area on the back of an individual (application site) was wetted with 10 mL of water delivered with a syringe. The test sunscreen composition was then applied to the application site in amounts as specified in the FDA monograph. To perform the static assay, the applied composition was allowed to dry for 15 minutes and then exposed to a fixed dose of UV radiation having a continuous emission spectrum from 290 nm to 400 nm with a limit of 1,500 W/m$^2$ using a solar simulator as specified in the FDA monograph. To perform the rinse/lather/rinse/rub assay, the applied composition was worked into a lather for two minutes and then the application site was rinsed for two minutes with 20 mL water, pat dried and then rubbed using moderate pressure for 20 seconds. The application site was then exposed to a fixed dose of UV radiation having a continuous emission spectrum from 290 nm to 400 nm with a limit of 1,500 W/m$^2$ using a solar simulator as specified in the FDA monograph. To perform the water immersion assay, the applied composition was allowed to dry for 15 minutes and then the application site immersed into a whirlpool bath for either 40 or 80 minutes. The application site was then exposed to a fixed dose of UV radiation having a continuous emission spectrum from 290 nm to 400 nm with a limit of 1,500 W/m$^2$ using a solar simulator as specified in the FDA monograph.

Table 1 shows the test results of a sunscreen body wash composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium, and one or more surfactants. In particular, a sunscreen body wash composition comprising about 11% of a cellulose encapsulate including a mixture of about 65% of an octocrylene and about 35% of avobenzone, about 8% of a cellulose encapsulate comprising octinoxate, about 2.5% of a polyquarternium, 10, about 3.5% sodium laureth sulfate, about 3.5% sodium lauryl sulfate and about 2.8% cocamido propylbetaine was tested. The results indicate that the disclosed sunscreen body wash composition had an average SPF value of 38.07 based on the static assay (Table 1). Interestingly, even after the rinse/lather/rinse/rub assay the average SPF value was still over 33 which represents only a 13% loss in SPF protection after a modified applied water method (Table 1).

TABLE 1

Evaluation of Sunscreen Body Wash Composition by SPF Determination (FDA) - Static and Rinse/Lather/Rinse/Rub Assays

| Subject No. | Gender | MED[b]/Hr | I[a] (Amps) | Skin Type | MED I (J/m$^2$) | MED II (J/m$^2$) | STD[c] | SPF Values | |
|---|---|---|---|---|---|---|---|---|---|
| | | | | | | | | Static | RLR/RUB[d] |
| 62-0539 | F | 127.3 | 6.0 | I | 30.33 | 30.33 | 16.30 | 39.60 | 34.50 |
| 48-9212 | F | 129.2 | 6.0 | II | 46.20 | 46.20 | 18.75 | 39.60 | 34.50 |

TABLE 1-continued

Evaluation of Sunscreen Body Wash Composition by SPF Determination (FDA) - Static and Rinse/Lather/Rinse/Rub Assays

| Subject No. | Gender | MED[b]/Hr | I[a] (Amps) | Skin Type | MED I (J/m$^2$) | MED II (J/m$^2$) | STD[c] | SPF Values Static | RLR/RUB[d] |
|---|---|---|---|---|---|---|---|---|---|
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 30.00 |
| 76-0164 | M | 125.9 | 6.0 | II | 46.20 | 46.20 | 18.75 | 39.60 | 34.50 |
| 54-1578 | F | 127.1 | 5.4 | II | 46.20 | 46.20 | 16.30 | 39.60 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| Mean (x) | | | | | | | 17.53 | 38.07 | 33.15 |
| Standard Deviation(s) | | | | | | | 1.29 | 2.46 | 2.17 |
| Standard Error | | | | | | | 0.41 | 0.78 | 0.69 |
| Standard Error % of Mean | | | | | | | 2.34 | 2.05 | 2.08 |
| N | | | | | | | 10 | 10 | 10 |
| Upper 5% t Dist. | | | | | | | 2.2622 | 1.8331 | 1.8331 |
| A Values | | | | | | | 0.9228 | 1.4260 | 1.2579 |
| Label SPF | | | | | | | 16 | 36 | 31 |

[a] I is Intensity of Light Source.
[b] MED is Minimal Erythemal Dose: 1 MED = 200 J/m$^2$-eff.
[c] 7% PadO/3% Oxyb.
[d] Rinse/Lather/Rinse/Rub assay.

Tables 2 and 3 show similar results. The sunscreen body wash compositions exhibited an average SPF value of 34.5 based on the static assay (Tables 2 and 3). However, even after an 80 water immersion assay, the UV radiation protective capabilities of these compositions were still maintained to an average SPF value of 34.5 (Table 2) and 32.25 (Tables 2 and 3). These results show that the disclose sunscreen body wash compositions demonstrate a significant increase in UV radiation protection and very good water resistant properties.

TABLE 2

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 78-4159 | M | 127.1 | 6.0 | II | 46.20 | 46.20 | 16.30 | 15.00 | 34.50 | 34.50 |
| 72-7479 | M | 128.1 | 6.0 | II | 46.20 | 46.20 | 18.75 | 18.00 | 34.50 | 34.50 |
| Mean (x) | | | | | | | 17.53 | 16.50 | 34.50 | 34.50 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

TABLE 3

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 78-4159 | M | 126.7 | 5.8 | II | 46.20 | 46.20 | 16.30 | 18.00 | 34.50 | 34.50 |
| 48-1671 | F | 126.2 | 6.0 | II | 30.33 | 30.33 | 18.75 | 15.00 | 34.50 | 30.00 |
| Mean (x) | | | | | | | 17.53 | 16.50 | 34.50 | 32.25 |
| Standard Deviation(s) | | | | | | | 1.73 | 2.12 | 0.00 | 3.18 |

TABLE 3-continued

Evaluation of Sunscreen Body Wash Composition by SPF Determination (FDA) - Static and 80 Minute Water Immersion Assays

| Subject | | | I[a] | Skin | MED I | MED II | | WR | SPF Values | |
|---|---|---|---|---|---|---|---|---|---|---|
| No. | Gender | MED[b]/Hr | (Amps) | Type | (J/m$^2$) | (J/m$^2$) | STD[c] | Control | Static | WR[d] |
| | | Standard Error | | | | | 1.23 | 1.50 | 0.00 | 2.25 |
| | | Standard Error % of Mean | | | | | 7.02 | 9.09 | 0.00 | 6.98 |
| | | N | | | | | 2 | 2 | 2 | 2 |

[a]I is Intensity of Light Source.
[b]MED is Minimal Erythemal Dose: 1 MED = 200 J/m$^2$-eff.
[c]7% PadO/3% Oxyb.
[d]Water Resistance based on water immersion assay.

Table 4 shows the test results of a sunscreen body wash composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium, and one or more surfactants. In particular, a sunscreen body wash composition comprising about 11% of a cellulose encapsulate including about 65% of an octocrylene and about 35% of avobenzone, about 8% of a cellulose encapsulate comprising octinoxate, about 2.5% of a polyquarternium, 10, about 4% disodium laureth sulfosuccinate, about 1.6% sodium cocoyl isethionate, about 1.6% cocamidopropyl betaine and about 1.6% sodium methyl cocoyl taurate was tested. The results indicate that the disclosed sunscreen body wash composition had an average SPF value of 36.54 based on the static assay (Table 4). Interestingly, even after the rinse/lather/rinse/rub assay the average SPF value was still over 33 (Table 4).

TABLE 4

Evaluation of Sunscreen Body Wash Composition by SPF Determination (FDA) - Static and Rinse/Lather/Rinse/Rub Assays

| Subject | | | I[a] | Skin | MED I | MED II | | SPF Values | |
|---|---|---|---|---|---|---|---|---|---|
| No. | Gender | MED[b]/Hr | (Amps) | Type | (J/m$^2$) | (J/m$^2$) | STD[c] | Static | RLR/RUB[d] |
| 62-0539 | F | 127.3 | 6.0 | I | 30.33 | 30.33 | 16.30 | 34.50 | 34.50 |
| 48-9212 | F | 129.2 | 6.0 | II | 46.20 | 46.20 | 18.75 | 34.50 | 34.50 |
| 78-4159 | M | 127.1 | 6.0 | II | 46.20 | 46.20 | 16.30 | 34.50 | 30.00 |
| 78-4237 | M | 128.4 | 6.0 | II | 46.20 | 46.20 | 18.75 | 39.60 | 34.50 |
| 72-7479 | M | 128.1 | 6.0 | II | 46.20 | 46.20 | 18.75 | 34.50 | 34.50 |
| 76-0164 | M | 125.9 | 6.0 | II | 46.20 | 46.20 | 18.75 | 39.60 | 34.50 |
| 54-1578 | F | 127.1 | 5.4 | II | 46.20 | 46.20 | 16.30 | 34.50 | 34.50 |
| 58-3948 | M | 128.4 | 6.0 | II | 46.20 | 46.20 | 16.30 | 34.50 | 30.00 |
| 70-8402 | F | 126.9 | 5.9 | III | 46.20 | 46.20 | 18.75 | 39.60 | 34.50 |
| 56-5529 | F | 125.4 | 6.0 | II | 30.33 | 30.33 | 16.30 | 39.60 | 34.50 |
| | | Mean (x) | | | | | 17.53 | 36.54 | 33.60 |
| | | Standard Deviation(s) | | | | | 1.29 | 2.63 | 1.90 |
| | | Standard Error | | | | | 0.41 | 0.83 | 0.60 |
| | | Standard Error % of Mean | | | | | 2.34 | 2.27 | 1.79 |
| | | N | | | | | 10 | 10 | 10 |
| | | Upper 5% t Dist. | | | | | 2.2622 | 1.8331 | 1.8331 |
| | | A Values | | | | | 0.9228 | 1.5246 | 1.1014 |
| | | Label SPF | | | | | 16 | 35 | 32 |

[a]I is Intensity of Light Source.
[b]MED is Minimal Erythemal Dose: 1 MED = 200 J/m$^2$-eff.
[c]7% PadO/3% Oxyb.
[d]Rinse/Lather/Rinse/Rub assay.

Tables 5 and 6 show similar results. The sunscreen body wash compositions exhibited an average SPF value of 34.5 based on the static assay (Tables 5 and 6). However, even after an 80 water immersion assay, the UV radiation protective capabilities of these compositions were still maintained to an average SPF value of 30.0 (Table 5 and 6). These results show that the disclose sunscreen body wash compositions demonstrate very water resistant properties.

TABLE 5

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 78-4159 | M | 127.1 | 6.0 | II | 46.20 | 46.20 | 16.30 | 15.00 | 34.50 | 30.00 |
| 72-7479 | M | 128.1 | 6.0 | II | 46.20 | 46.20 | 18.75 | 18.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

TABLE 6

Evaluation of Sunscreen Body Wash Composition by SPF Determination (FDA) - Static and 80 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 78-4159 | M | 126.7 | 5.8 | II | 46.20 | 46.20 | 16.30 | 18.00 | 34.50 | 30.00 |
| 48-1671 | F | 126.2 | 6.0 | II | 30.33 | 30.33 | 18.75 | 15.00 | 34.50 | 30.00 |
| Mean (x) | | | | | | | 17.53 | 16.50 | 34.50 | 30.00 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

Example 2: SPF Testing of Sunscreen Lotion Compositions

Sunscreen lotion compositions disclosed herein were tested to determine their SPF value using the static and water immersion (40 or 80 minute) assays as described in Example 1.

Experiments were conducted with a sunscreen lotion composition comprising a photostabilizing agent. Table 7 shows the test results of a sunscreen lotion composition disclosed herein comprises a cellulose encapsulate comprising a broad spectrum UVA/UVB sunscreen active agent, a UVA sunscreen active agent and a photostabilizing agent, a cellulose encapsulate comprising a UVB sunscreen active agent, a cellulose encapsulate comprising a silicone oil, a cellulose encapsulate comprising a comprising a shea oil, one or more emollients and one or more thickening agents.

In particular, a sunscreen lotion composition comprising about 0.15% of a cellulose encapsulate comprising a silicone oil, about 0.2% of a cellulose encapsulate comprising a shea oil, about 11% of a cellulose encapsulate comprising about 63% of an octocrylene, about 35% of avobenzone and about 2% trimethoxy benylidene pentanedione, about 8% of a cellulose encapsulate comprising octinoxate, about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (DERMACYL® AFQ) was tested. The results indicate that the disclosed sunscreen lotion composition had an average SPF value of 64.50 based on the static assay (Table 7). However, even after a 40 water immersion assay, the UV radiation protective capabilities of this composition was maintained, dropping only to an average SPF value of 30.0 (Table 7).

TABLE 7

Evaluation of Sunscreen Lotion Composition Comprising Photostabilizing Agent by SPF Determination (FDA) - Static and 40 Minute Water Immersion Assays

| Subject No. | Gender | MED[b]/Hr | I[a] (Amps) | Skin Type | MED I (J/m$^2$) | MED II (J/m$^2$) | STD[c] | WR Control | SPF Values Static | WR[d] |
|---|---|---|---|---|---|---|---|---|---|---|
| 74-5879 | M | 126.9 | 6.0 | III | 35.55 | 35.55 | 18.75 | 18.00 | 60.00 | <45.60 |
| 56-5529 | F | 128.5 | 6.5 | II | 28.44 | 28.44 | 18.75 | 15.00 | 69.00 | 30.00 |

TABLE 7-continued

Evaluation of Sunscreen Lotion Composition Comprising Photostabilizing Agent by SPF Determination (FDA) - Static and 40 Minute Water Immersion Assays

| Subject | | | $I^a$ | Skin | MED I | MED II | | WR | SPF Values | |
|---|---|---|---|---|---|---|---|---|---|---|
| No. | Gender | $MED^b$/Hr | (Amps) | Type | $(J/m^2)$ | $(J/m^2)$ | $STD^c$ | Control | Static | $WR^d$ |
| Mean (x) | | | | | | | 18.75 | 16.50 | 64.50 | 30.00 |
| Standard Deviation(s) | | | | | | | 0.00 | 2.12 | 6.36 | N/A |
| Standard Error | | | | | | | 0.00 | 1.50 | 4.50 | N/A |
| Standard Error % of Mean | | | | | | | 0 | 9.09 | 6.98 | N/A |
| N | | | | | | | 2 | 2 | 2 | 1 |

$^a$I is Intensity of Light Source.
$^b$MED is Minimal Erythemal Dose: 1 MED = 200 $J/m^2$-eff.
$^c$7% PadO/3% Oxyb.
$^d$Water Resistance based on water immersion assay.

Table 8 shows similar results. The disclosed sunscreen lotion composition exhibited an average SPF value of 69.0 based on the static assay (Table 8). However, even after an 80 water immersion assay, the UV radiation protective capabilities of this composition was maintained, dropping only to an average SPF value of 52.2 (Table 8). These results indicate that a photostabilizing agent significantly increases the UV radiation protective capabilities of a sunscreen composition, and that this enhanced protective effect appears to be maintained even exposure to water immersion.

lotion composition comprising about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldi-

TABLE 8

Evaluation of Sunscreen Lotion Composition Comprising Photostabilizing Agent by SPF Determination (FDA) - Static and 80 Minute Water Immersion Assays

| Subject | | | $I^a$ | Skin | MED I | MED II | | WR | SPF Values | |
|---|---|---|---|---|---|---|---|---|---|---|
| No. | Gender | $MED^b$/Hr | (Amps) | Type | $(J/m^2)$ | $(J/m^2)$ | $STD^c$ | Control | Static | $WR^d$ |
| 66 0787 | F | 127.4 | 6.0 | II | 28.44 | 28.44 | 16.30 | 15.00 | 69.00 | 52.20 |
| 56 2197 | F | 128.4 | 6.5 | II | 35.55 | 35.55 | 18.75 | 18.00 | 69.00 | 52.20 |
| Mean (x) | | | | | | | 17.53 | 16.50 | 69.00 | 52.20 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

$^a$I is Intensity of Light Source.
$^b$MED is Minimal Erythemal Dose: 1 MED = 200 $J/m^2$-eff.
$^c$7% PadO/3% Oxyb.
$^d$Water Resistance based on water immersion assay.

Experiments were conducted with a sunscreen lotion composition comprising a film former. Table 9 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a cellulose encapsulate comprising a silicone oil, a cellulose encapsulate comprising a comprising a shea oil, a film former, one or more emollients and one or more thickening agents. In particular, a sunscreen methyl taurate copolymer-based thickening agent including isohexadecane and polysorbate 80 (SIMLGEL® EG) was tested. The results indicate that the disclosed sunscreen lotion composition had an average SPF value of 57.5 based on the static assay (Table 9). However, even after a 40 water immersion assay, the UV radiation protective capabilities of this composition was maintained, dropping only to an average SPF value of 43.5 (Table 9).

TABLE 9

Evaluation of Sunscreen Lotion Composition Comprising Film Former by SPF Determination (FDA) - Static and 40 Minute Water Immersion Assays

| Subject | | | $I^a$ | Skin | MED I | MED II | | WR | SPF Values | |
|---|---|---|---|---|---|---|---|---|---|---|
| No. | Gender | $MED^b$/Hr | (Amps) | Type | $(J/m^2)$ | $(J/m^2)$ | $STD^c$ | Control | Static | $WR^d$ |
| 46 4829 | F | 127.3 | 6.4 | II | 35.55 | 35.55 | 18.75 | 18.00 | 57.50 | 43.50 |
| 74 0656 | F | 126.2 | 6.5 | I | 28.44 | 28.44 | 16.30 | 18.00 | 57.50 | 43.50 |

TABLE 9-continued

Evaluation of Sunscreen Lotion Composition Comprising Film Former by SPF Determination (FDA) - Static and 40 Minute Water Immersion Assays

| Subject | | | | | | | | WR | SPF Values | |
|---|---|---|---|---|---|---|---|---|---|---|
| No. | Gender | MED[b]/Hr | I[a] (Amps) | Skin Type | MED I (J/m$^2$) | MED II (J/m$^2$) | STD[c] | Control | Static | WR[d] |
| Mean (x) | | | | | | | 17.53 | 18.00 | 57.50 | 43.50 |
| Standard Deviation(s) | | | | | | | 1.73 | 0.00 | 0.00 | 0.00 |
| Standard Error | | | | | | | 1.22 | 0.00 | 0.00 | 0.00 |
| Standard Error % of Mean | | | | | | | 6.96 | 0 | 0 | 0 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

Table 10 shows similar results. The disclosed sunscreen lotion composition exhibited an average SPF value of 53.75 based on the static assay (Table 10). However, even after an 80 water immersion assay, the UV radiation protective capabilities of this composition was maintained, dropping only to an average SPF value of 43.5 (Table 10). These results indicate that a film former significantly increases the UV radiation protective capabilities of a sunscreen composition, and that this enhanced protective effect appears to be maintained even exposure to water immersion.

TABLE 10

Evaluation of Sunscreen Lotion Composition Comprising Film Former by SPF Determination (FDA) - Static and 80 Minute Water Immersion Assays

| Subject | | | | | | | | WR | SPF Values | |
|---|---|---|---|---|---|---|---|---|---|---|
| No. | Gender | MED[b]/Hr | I[a] (Amps) | Skin Type | MED I (J/m$^2$) | MED II (J/m$^2$) | STD[c] | Control | Static | WR[d] |
| 58 5653 | F | 128.3 | 6.0 | II | 28.44 | 28.44 | 18.75 | 18.00 | 57.50 | 43.50 |
| 68 4430 | F | 129.9 | 6.5 | I | 35.55 | 35.55 | 16.30 | 15.00 | 50.00 | 43.50 |
| Mean (x) | | | | | | | 17.53 | 16.50 | 53.75 | 43.50 |
| Standard Deviation(s) | | | | | | | 1.73 | 2.12 | 5.30 | 0.00 |
| Standard Error | | | | | | | 1.23 | 1.50 | 3.75 | 0.00 |
| Standard Error % of Mean | | | | | | | 7.02 | 9.09 | 6.98 | 0.00 |
| N | | | | | | | 2 | 2 | 2 | 2 |

[a] I is Intensity of Light Source.
[b] MED is Minimal Erythemal Dose: 1 MED = 200 J/m$^2$-eff.
[c] 7% PadO/3% Oxyb.
[d] Water Resistance based on water immersion assay.

Experiments were conducted with a sunscreen lotion composition comprising a photostabilizing agent and a film former. Table 11 shows the test results of a sunscreen lotion composition disclosed herein comprises a cellulose encapsulate comprising a broad spectrum UVA/UVB sunscreen active agent, a UVA sunscreen active agent and a photostabilizing agent, a cellulose encapsulate comprising a UVB sunscreen active agent, a cellulose encapsulate comprising a silicone oil, a cellulose encapsulate comprising a comprising a shea oil, a film former, one or more emollients and one or more thickening agents. In particular, a sunscreen lotion composition comprising about 0.15% of a cellulose encapsulate comprising a silicone oil, about 0.2% of a cellulose encapsulate comprising a shea oil, about 8% of a cellulose encapsulate comprising about 63% of an octocrylene, about 35% of avobenzone and about 2% trimethoxy benylidene pentanedione, about 6% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (SIMLGEL® EG) was tested. The results indicate that the disclosed sunscreen lotion composition had an average SPF value of 69.0 based on the static assay (Table 11). In addition, even after an 80 water immersion assay, the UV radiation protective capabilities of this composition was maintained, dropping only to an average SPF value of 52.2 (Table 11). These results indicate that while a photostabilizing agent significantly increases the UV radiation protective capabilities of a sunscreen composition, the addition of a film former appears to maintain this enhanced protective effect after exposure to water immersion.

TABLE 11

Evaluation of Sunscreen Lotion Composition Comprising Photostabilizing Agent and Film Former by SPF Determination (FDA) - Static and 80 Minute Water Immersion Assays

| Subject No. | Gender | I[a] MED[b]/Hr (Amps) | | Skin Type | MED I (J/m$^2$) | MED II (J/m$^2$) | STD[c] | WR Control | SPF Values Static | WR[d] |
|---|---|---|---|---|---|---|---|---|---|---|
| 66 0787 | F | 127.4 | 6.0 | II | 28.44 | 28.44 | 16.30 | 15.00 | 69.00 | 52.20 |
| 56 2197 | F | 128.4 | 6.5 | II | 35.55 | 35.55 | 18.75 | 18.00 | 69.00 | 52.20 |
| Mean (x) | | | | | | | 17.53 | 16.50 | 69.00 | 52.20 |
| Standard Deviation(s) | | | | | | | 1.73 | 2.12 | 0.00 | 0.00 |
| Standard Error | | | | | | | 1.23 | 1.50 | 0.00 | 0.00 |
| Standard Error % of Mean | | | | | | | 7.02 | 9.09 | 0.00 | 0.00 |
| N | | | | | | | 2 | 2 | 2 | 2 |

[a]I is Intensity of Light Source.
[b]MED is Minimal Erythemal Dose: 1 MED = 200 J/m$^2$-eff.
[c]7% PadO/3% Oxyb.
[d]Water Resistance based on water immersion assay.

Example 3: SPF Testing of Sunscreen Soap Compositions

Sunscreen soap compositions disclosed herein were tested to determine their SPF value using the static and water immersion (40 minute) assays as described in Example 1, except that prior to application, the sunscreen soap composition was dissolve in water, such that it was diluted to a 50% concentration and the prepared solution was then delivered to the test site at a dosage of 4.0 mg/cm$^2$.

Table 12 shows the test results of a sunscreen soap composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium mixed into a soap base. In particular, a sunscreen soap composition comprising about 8% of a cellulose encapsulate comprising about 65% of an octocrylene and about 35% of avobenzone, about 6% of a cellulose encapsulate comprising octinoxate and about 2% of polyquarternium 16 mixed into a soap base was tested. The results indicate that the disclosed sunscreen lotion composition had an average SPF value of 25.3 based on the static assay (Table 12). However, after a 40 water immersion assay, the UV radiation protective capabilities of this composition was not maintained (Table 12).

Example 4: SPF Testing of Sunscreen After Shower Body Lotion Compositions

Sunscreen after shower body lotion compositions disclosed herein were tested to determine their SPF value using the static assay as described in Example 1.

Table 13 shows the test results of a sunscreen after shower body lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a cellulose encapsulate comprising a silicone oil, a cellulose encapsulate comprising shea oil, a polyquarternium, a film former and one or more surfactants. In particular, a sunscreen after shower body lotion composition comprising about 11% of a cellulose encapsulate comprising about 65% of an octocrylene and about 35% of avobenzone, about 8% of a cellulose encapsulate comprising octinoxate, about 0.15% of a cellulose encapsulate comprising a silicone oil, about 0.2% of a cellulose encapsulate comprising a shea oil, about 2.5% of polyquarternium 4 or polyquarternium 10, about 2.5% of an acrylate copolymer (DERMACRYL® AQF), about 2.0% acrylate-sodium acryloyldimethyl taurate copolymer-based thickening agent including isohexadecane and polysorbate 80 (SIMLGEL® EG) and about 1.5% cocamidopropyl betaine was tested. The results indicate that the disclosed sunscreen after shower body lotion composition had an average SPF value of 46 based on the static assay (Table 13).

TABLE 12

Evaluation of Sunscreen Soap Composition by SPF Determination (FDA) - Static and 40 Minute Water Immersion Assays

| Subject No. | Gender | I[a] MED[b]/Hr (Amps) | | Skin Type | MED I (J/m$^2$) | MED II (J/m$^2$) | STD[c] | WR Control | SPF Values Static | WR[d] |
|---|---|---|---|---|---|---|---|---|---|---|
| 74 5198 | M | 129.3 | 6.4 | II | 28.44 | 28.44 | 18.75 | 18.00 | 25.30 | <16.72 |
| 52 3527 | F | 126.6 | 6.5 | II | 44.44 | 44.44 | 16.30 | 15.00 | 25.30 | 15.00 |
| Mean (x) | | | | | | | 17.53 | 16.50 | 25.30 | 15.00 |
| Standard Deviation(s) | | | | | | | 1.73 | 2.12 | 0.00 | N/A |
| Standard Error | | | | | | | 1.22 | 1.50 | 0.00 | N/A |
| Standard Error % of Mean | | | | | | | 6.96 | 9.09 | 0 | N/A |
| N | | | | | | | 2 | 2 | 2 | 1 |

[a]I is Intensity of Light Source.
[b]MED is Minimal Erythemal Dose: 1 MED = 200 J/m$^2$-eff.
[c]7% PadO/3% Oxyb.
[d]Water Resistance based on water immersion assay.

TABLE 13

Evaluation of Sunscreen After Shower Body Lotion Composition by SPF Determination (FDA) - Static Assay

| Subject No. | Gender | MED[b]/Hr | I[a] (Amps) | Skin Type | MED I (J/m²) | MED II (J/m²) | STD[c] | SPF Values |
|---|---|---|---|---|---|---|---|---|
| 54 2436 | F | 128.4 | 6.0 | II | 30.33 | 30.33 | 16.30 | 46 |
| 48 5699 | M | 125.7 | 6.0 | II | 30.33 | 30.33 | 16.30 | 46 |
| Mean (x) | | | | | | | 16.30 | 46 |
| Standard Deviation(s) | | | | | | | 0 | 0 |
| Standard Error | | | | | | | 0 | 0 |
| Standard Error % of Mean | | | | | | | 0 | 0 |
| N | | | | | | | 2 | 2 |

[a]I is Intensity of Light Source.
[b]MED is Minimal Erythemal Dose: 1 MED = 200 J/m²-eff.
[c]7% PadO/3% Oxyb.

Example 5: SPF Testing of Sunscreen Lotion Compositions

Sunscreen lotion compositions disclosed herein were tested to determine their SPF value using the static assay as described in Example 1.

Experiments were conducted with a sunscreen lotion composition comprising a polyquarternium and a film former. Table 14 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium and a film former. In particular, a sunscreen lotion composition comprising about 13.5% of a cellulose encapsulate comprising about 65% of an octocrylene and about 35% of avobenzone, about 13.5% of a cellulose encapsulate comprising octinoxate, about 0.7% of polyquarternium 4 and about 2% of an acrylate copolymer (DERMACRYL® AQF) was tested. The results indicate that the disclosed sunscreen lotion composition had an average SPF value of 37.05 based on the static assay (Table 14).

TABLE 14

Evaluation of Sunscreen Lotion Composition by SPF Determination (FDA) - Static Assay

| Subject No. | Gender | MED[b]/Hr | I[a] (Amps) | Skin Type | MED I (J/m²) | MED II (J/m²) | STD[c] | SPF Values |
|---|---|---|---|---|---|---|---|---|
| 58 7412 | F | 127.4 | 6.0 | II | 46.20 | 46.20 | 16.30 | 34.50 |
| 70 6353 | F | 126.5 | 6.4 | II | 30.33 | 30.33 | 18.75 | 39.60 |
| Mean (x) | | | | | | | 17.53 | 37.05 |
| Standard Deviation(s) | | | | | | | 1.73 | 3.61 |
| Standard Error | | | | | | | 1.23 | 2.55 |
| Standard Error % of Mean | | | | | | | 7.02 | 6.88 |
| N | | | | | | | 2 | 2 |

[a]I is Intensity of Light Source.
[b]MED is Minimal Erythemal Dose: 1 MED = 200 J/m²-eff.
[c]7% PadO/3% Oxyb.

Experiments were conducted with a sunscreen lotion composition comprising a polyquarternium, a film former and an arachnid/insect repellent. Table 15 shows the test results of a sunscreen lotion composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium, a film former and an arachnid/insect repellent. In particular, a sunscreen lotion composition comprising about 13.5% of a cellulose encapsulate comprising about 65% of an octocrylene and about 35% of avobenzone, about 13.5% of a cellulose encapsulate comprising octinoxate, about 0.7% of polyquarternium 4, about 2% of an acrylate copolymer (DERMACRYL® AQF) and about 5% citronella was tested. The results indicate that the disclosed sunscreen lotion composition had an average SPF value of 37.05 based on the static assay (Table 15).

TABLE 15

Evaluation of Sunscreen Lotion Composition by SPF Determination (FDA) - Static Assay

| Subject No. | Gender | MED[b]/Hr | $I^a$ (Amps) | Skin Type | MED I $(J/m^2)$ | MED II $(J/m^2)$ | STD[c] | SPF Values |
|---|---|---|---|---|---|---|---|---|
| 58 7412 | F | 127.4 | 6.0 | II | 46.20 | 46.20 | 16.30 | 34.50 |
| 70 6353 | F | 126.5 | 6.4 | II | 30.33 | 30.33 | 18.75 | 39.60 |
| Mean (x) | | | | | | | 17.53 | 37.05 |
| Standard Deviation(s) | | | | | | | 1.73 | 3.61 |
| Standard Error | | | | | | | 1.23 | 2.55 |
| Standard Error % of Mean | | | | | | | 7.02 | 6.88 |
| N | | | | | | | 2 | 2 |

[a] I is Intensity of Light Source.
[b] MED is Minimal Erythemal Dose: 1 MED = 200 $J/m^2$-eff.
[c] 7% PadO/3% Oxyb.

Example 6: SPF Testing of Sunscreen Lip Balm Compositions

A sunscreen lip balm compositions disclosed herein were tested to determine their SPF value using the static and water immersion (80 minute) assays as described in Example 1.

Experiments were conducted with a sunscreen lip balm composition comprising a polyquarternium and a film former. Table 16 shows the test results of a sunscreen lip balm composition disclosed herein comprises a cellulose encapsulate comprising a broad spectrum UVA/UVB sunscreen active agent and a UVA sunscreen active agent, a cellulose encapsulate comprising a UVB sunscreen active agent, a polyquarternium and a film former. In particular, a sunscreen lip balm composition comprising about 15% of a cellulose encapsulate comprising about 51% homosalate, about 24% octyl salicylate, about 13% avobenzone, about 6% trimethoxybenzylidene pentanedione (SYNOXYL® HSS) and about 5% of a polymer, 25% petroleum and 12% cocoa butter was tested. The results indicate that the disclosed sunscreen lip balm composition had an average SPF value of 44.20 based on the static assay (Table 16). In addition, even after an 80 water immersion assay, the UV radiation protective capabilities of this composition was maintained, dropping only to an average SPF value of 43.60 (Table 16). These results show that the disclose sunscreen lip balm compositions demonstrate a significant increase in UV radiation protection and very good water resistant properties.

TABLE 16

Evaluation of Sunscreen Lip Balm Composition by SPF Determination (FDA) - Static and 80 Minute Water Immersion Assays

| Subject No. | Gender | MED[b]/Hr | $I^a$ (Amps) | Skin Type | MED I $(J/m^2)$ | MED II $(J/m^2)$ | STD[c] | WR Control | SPF Values Static | WR[d] |
|---|---|---|---|---|---|---|---|---|---|---|
| 74 2314 | M | 126.1 | 6.1 | III | 44.44 | 44.44 | 16.30 | 18.00 | 46.00 | 46.00 |
| 82 8976 | F | 127.1 | 6.1 | III | 55.55 | 55.55 | 16.30 | 15.00 | 46.00 | 46.00 |
| 86 0336 | F | 125.5 | 6.3 | I | 28.44 | 28.44 | 16.30 | 18.00 | 46.00 | 46.00 |
| 56 9343 | F | 127.7 | 6.1 | II | 44.44 | 44.44 | 16.30 | 15.00 | 46.00 | 40.00 |
| 54 5854 | M | 127.1 | 6.1 | II | 44.44 | 44.44 | 18.75 | 18.00 | 46.00 | 46.00 |
| 52 0005 | M | 127.6 | 6.0 | II | 28.44 | 28.44 | 16.30 | 15.00 | 40.00 | 40.00 |
| 62 0069 | M | 127.3 | 6.0 | II | 35.55 | 35.55 | 16.30 | 18.00 | 46.00 | 46.00 |
| 76 5957 | F | 126.4 | 6.2 | II | 35.55 | 35.55 | 18.75 | 15.00 | 40.00 | 40.00 |
| 54 4669 | F | 126.3 | 6.0 | III | 55.55 | 55.55 | 18.75 | 18.00 | 40.00 | 40.00 |
| 52 6776 | F | 128.3 | 6.3 | II | 44.44 | 44.44 | 16.30 | 15.00 | 46.00 | 46.00 |
| Mean (x) | | | | | | | 17.04 | 16.50 | 44.20 | 43.60 |
| Standard Deviation(s) | | | | | | | 1.18 | 1.58 | 2.90 | 3.10 |
| Standard Error | | | | | | | 0.37 | 0.50 | 0.92 | 0.98 |
| Standard Error % of Mean | | | | | | | 2.17 | 3.03 | 2.08 | 2.25 |
| N | | | | | | | 10 | 10 | 10 | 10 |

[a] I is Intensity of Light Source.
[b] MED is Minimal Erythemal Dose: 1 MED = 200 $J/m^2$-eff.
[c] 7% PadO/3% Oxyb.
[d] Water Resistance based on water immersion assay.

Alternatively, testing can be done on a sunscreen lip balm composition comprising about 15% of a cellulose encapsulate comprising about 51% homosalate, about 24% octyl salicylate, about 13% avobenzone, about 3% ethylhexyl methoxycrylene (SOLASTAY® S1) and about 3% of a bis-methoxycrylene/octyldodecyl adipic acid/methylpropanediol copolymer (SOLASTAY® P1), 25% petroleum and 12% cocoa butter. Similar SPF results are expected.

Alternatively, testing can be done on a sunscreen lip balm composition comprising about 15% of a cellulose encapsulate comprising about 51% homosalate, about 24% octyl salicylate, about 13% avobenzone, about 2% trimethoxybenzylidene pentanedione (SYNOXYL® HSS), about 2% ethylhexyl methoxycrylene (SOLASTAY® S1) and about 2% of a bis-methoxycrylene/octyldodecyl adipic acid/methylpropanediol copolymer (SOLASTAY® P1), 25% petroleum and 12% cocoa butter. Similar SPF results are expected.

Example 7: Skin Penetration Experiments

An experiment was conducted to demonstrate that sunscreen active agents contained within the presently claimed cellulose derived capsules prevent absorption of the sunscreen active agents into the skin. Two sunscreen compositions were prepared. Sunscreen Composition 1 (Sun Comp 1) was a commercially available sunscreen formulation that contained 4.5% octylmethoxy cinnamate (unencapsulated or free) and was spiked with 0.2% Nile Red fluorescent dye. Sunscreen Composition 2 (Sun Comp 2) contained flexible cellulose derived capsules containing 4.5% octylmethoxy cinnamate and 0.2% Nile Red fluorescent dye.

Previously frozen (−80° C.) deidentified human breast skin (n=5) from a common donor were prepared by cleaning the skin surface with 70% ethanol and air dried for 5 minutes to remove superficial fluids that might impact absorption. Each sunscreen composition was then applied to a separate region of the surface of the prepared samples by spreading the composition with a plastic pipet tip to form an even layer with a minimum 5 mm margin of untreated surface at the cut edges, Each skin sample received a total dose of 5 mg/cm$^2$ of each sunscreen composition. After dosing samples were incubated on a 35° C. flat surface with the inner sides of the samples kept hydrated with PBS buffer. Data was acquired for incubation times of 30 minutes and 90 minutes for each product type. Ager incubation, skin samples were blotted with absorbent paper to remove superficial sunscreen, then cleaned twice with fresh paper moistened with deionized water. Samples were mounted on a Vivascope 1500 fluorescence microscope fitted with a 658 nm, 531 nm, and 488 nm laser. Sample height and suitable topography were identified and imaged using 658 nm illumination in reflectance mode, and a co-registered fluorescence image stack was acquired at 10 µm depth steps using 488 nm illumination and a 607 nm filter set. Regions of Interest (ROI) of 100 by 100 pixels were identified in the 658 nm stack, confirmed in the 488 nm stack, and image intensity information was analyzed using ImageJ software (NIH) for each depth profile.

FIG. 1 indicates that dye penetration into skin is dramatically reduced (70%-80%) in the encapsulated formulation of Sunscreen Composition 2 relative to identically spiked commercial formulation of Sunscreen Composition 1, reflecting a strong reduction of octylmethoxy cinnamate absorption. In addition, no significant change in the overall concentration is observed between 30 and 90 minute time points, reflecting approximately steady-state flux, as the high surface concentration diffuses in to a relatively large volume of skin.

Figure 2:
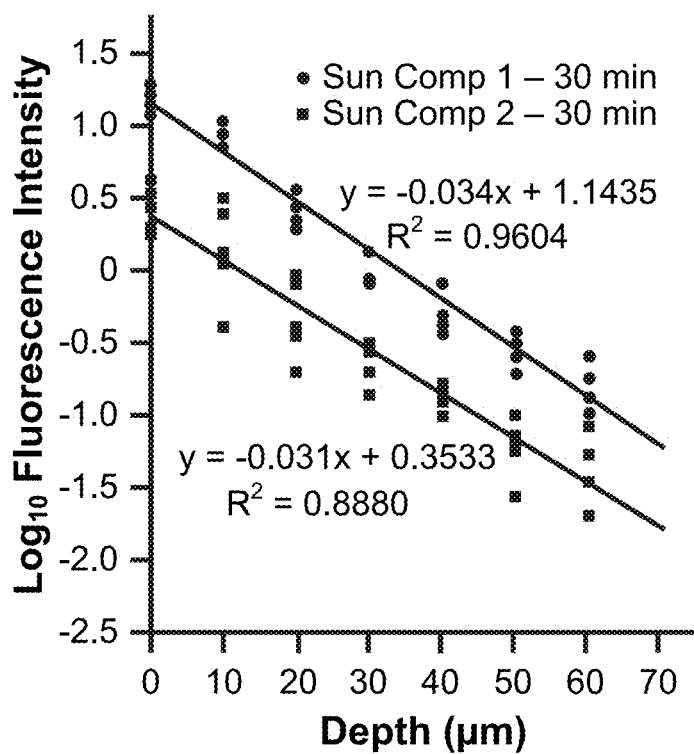
FIG. 2 shows a graph of dye penetration into human skin using $\log_{10}$ fluorescence intensity of dye versus penetration depth of dye. Data from the 30 minutes after application of a composition were used.

Replotting the fluorescence data using the 30 minute time point on a log scale indicated that the intensity drops with depth in an approximately linear fashion (FIG. 2). This is consistent with the idea that the diffusion rate for the octylmethoxy cinnamate/Nile Red dye solution should be constant in the skin independent of the formulation. The intercept however, shows that the penetration of the octylmethoxy cinnamate/Nile Red dye solution at the skin surface is substantially reduced for the encapsulated formulation of Sunscreen Composition 2. This finding indicates that encapsulated octylmethoxy cinnamate of the encapsulated formulation of Sunscreen Composition 2 prevented the skin from becoming saturated with this sunscreen active agent.

FIGS. 3A-C visually shows that the vast majority of the fluorescent dye containing cellulose derived capsules remained on the skin surface (compare 10 µm skin depth photograph of FIG. 3A with 50 µm skin depth photograph of FIG. 3B and 90 µm skin depth photograph of FIG. 3C). For example, at 10 µm the stratum corneum is high reflective and appears bright. However, in deep locations, there is no bright appearance. Quantitation of the fluorescence indicate that very little penetration of the fluorescent dye occurred below 10 µm from the skin surface (FIG. 3D). In comparison to the commercial formulation of Sunscreen Composition 1, these results indicate that there is an 80% reduction in skin penetration of the florescent dye when using Sunscreen Composition 2.

Thus, in summary, these experimental results show that the encapsulated formulation of Sunscreen Composition 2 reduced the concentration of sunscreen at the skin surface by 80%, reduced the sunscreen active agent dose absorbed into the live layers of the epidermis by 80% and reduced sunscreen active agent availability to the skin surface so that SPF cannot diffuse into the skin.

Example 8: Product Comparison

An assessment was conducted to determine the amount of active sunscreen agent needed in a sunscreen compositions to achieve an average SPF value of 50. Six sunscreen compositions were assessed. Composition 1 was a sunscreen lotion composition disclosed herein comprising about 0.15% of a cellulose encapsulate comprising a silicone oil, about 0.2% of a cellulose encapsulate comprising a shea oil, about 11% of a cellulose encapsulate comprising about 65% of an octocrylene and about 35% of avobenzone, about 8% of a cellulose encapsulate comprising octinoxate, about 3% of an acrylate copolymer (DERMACRYL® AQF), about 3.5% capryllic capric triglyceride, and about 2% dimethicone-vinyldimethyl trimethylsiloxysilicate-dimethicone crosspolymer and about 2.5% acrylate-sodium acryloyldimethyl taurate copolymer-based thickening agent including isohexadecane and polysorbate 80 (SIMLGEL® EG). Compositions 2-6 were commercially available sunscreen products having an SPF 50 value. Analysis of all six compositions revealed that to achieve an SPF 50, Composition 1 required about 13% by weight active sunscreen agents in an encapsulated form (FIG. 4). On the other hand, Compositions 2-6 required from about 22% to about 29% by weight active sunscreen agents to achieve a SPF value of 50 (FIG. 4). These results indicate that the sunscreen composition disclosed herein increases the efficacy of a UV absorber by at least 70%.

Example 9: Arachnid and Insect Repellency Assay

Experiments were conducted to assess the mosquito repellency of compositions disclosed herein using two different assays.

To conduct a tick repellent assay, a 4 cm×8 cm basket with a 4 cm×4 cm opening in the bottom is suspended over a petri dish containing 10 *Rhipicephalus sanguineus* (Brown Dog Tick). A 4 cm×4 cm filer paper is attached to a 4 cm×8 cm paper and placed at the bottom of the basket so that the 4 cm×4 cm filer paper cover the 4 cm×4 cm opening located in the basket's bottom. A sample of blood is placed within the 4 cm×4 cm area of the filter paper. For the control composition, the filter paper is moistened with water and the number and of ticks attached to the bottom of the basket and the location distance from the 4 cm×4 cm filter paper was assessed during a 10 minute time period at 3 minutes, 5 minutes and 10 minutes. For the test compositions, the filter paper is treated by gently applying a roll-on applicator containing the test composition and the number and of ticks attached to the bottom of the basket and the location distance from the 4 cm×4 cm filter paper was assessed during a 10 minute time period at 3 minutes, 5 minutes and 10 minutes. Test composition 110216 is a lotion composition comprising about 14% of a cellulose encapsulate comprising about 94% Lemon *Eucalyptus* oil and about 6% of a polymer, 20% geraniol, 3% of a film former (DERMACRYL® E), about 1% fragrance and about 32% water. The data is shown in Table 17. The test composition shows a significant repellent activity compared to the control. Alternatively, tick repellency testing can be done using Test composition 100316 or Test composition 113016Z discussed below.

TABLE 17

Tick Repellent Assay

| Composition | N | 3 min | 5 min | 10 min | Mean |
| --- | --- | --- | --- | --- | --- |
| | | Repellency | | | |
| Control | 7 | 63% | 42% | 47% | 51% |
| Test 110216 | 7 | 94% | 95% | 96% | 95% |

Assay for each compsition was repeated four times.

To conduct an AEDSAE 16 assay, a mosquito cage is set up with 25 female *Aedes aegypti* mosquitos. The top lid of the cage has a 2.5" by 6" opening in the center. A collagen membrane is place over the opening and is used as the test surface because it mimics human skin. A test subject's forearm is then positioned over the opening. Mesh is placed on the top side of the test surface to prevent direct contact of the test surface with the test subject's arm and disposable wood spacers are placed on top of the top cover to elevate the test subject's arm from the test substance and to prevent the mosquitos from being able to feed on the test subject. Pre-treatment landing and probing numbers were obtained by counting the number of mosquitos that landed and probed the collagen membrane during a 5 minute time period. Treatment landing and probing numbers were obtained as follows: for the control composition, the collagen membrance is moistened with water and landing and probing numbers were obtained by counting the number of mosquitos that landed and probed the treated collagen membrane during a 5 minute time period; for the test compositions, the collagen membrane is treated by gently applying a roll-on applicator containing the test composition and landing and probing numbers were obtained by counting the number of mosquitos that landed and probed the treated collagen membrane during a 5 minute time period. Test composition 100316 is a lotion composition comprising about 20% of a cellulose encapsulate comprising about 47% Lemon *Eucalyptus* oil, about 47% IR3535 and about 6% of a polymer, 3% of a film former (DERMACRYL® AQF), about 3% fragrance and about 40% water. Test composition 113016Z is a lotion composition comprising about 20% of a cellulose encapsulate comprising about 94% Lemon *Eucalyptus* oil and about 6% of a polymer, 3% of a film former (DERMACRYL® AQF), about 1% fragrance and about 44% water. Landing and probing numbers were collected at 1 hour, 2 hours and 4 hours after treatment of the collagen membrane. The percent landing and probing numbers were calculated by comparing the number of landing and probes during the pre-treatment evaluation to the number of landing and probes during the treatment evaluation at all three time intervals. The data is shown in Table 18. Both test compositions show a significant repellent activity compared to the control. Alternatively, mosquito repellency testing can be done using Test composition 110216 discussed above.

TABLE 18

Mosquito Repellent Assay

| Composition | Post-Treatment Time (1 hr) | | Post-Treatment Time (2 hr) | | Post-Treatment Time (4 hr) | |
| --- | --- | --- | --- | --- | --- | --- |
| | Landings | Probes | Landings | Probes | Landings | Probes |
| Control | −13% | −10% | −25% | −14% | −13% | −11% |
| Test 100316 | 100% | 100% | 99% | 100% | 91% | 99% |
| Test 113016Z | 100% | 100% | 94% | 99% | 96% | 100% |

Assay for each test composition was repeated four times. Assay for the control composition was repeated twice.

Alternatively, arachnid/insect repellency testing can be done on a sunscreen/insect repellent composition comprising about 15% of a cellulose encapsulate comprising about 25.5% homosalate, about 12% octyl salicylate, about 6.5% avobenzone, about 1.5% ethylhexyl methoxycrylene (SOLASTAY® S1), about 1.5% of a bis-methoxycrylene/octyldodecyl adipic acid/methylpropanediol copolymer (SOLASTAY® P1), about 23.5% Lemon *Eucalyptus* oil, about 23.5% IR3535 and about 3% of a polymer, 3% of a film former (DERMACRYL® AQF) and about 3% fragrance. Similar SPF and repellency results are expected.

Alternatively, arachnid/insect repellency testing can be done on a sunscreen sunscreen/insect repellent composition comprising about 15% of a cellulose encapsulate comprising about 25.5% homosalate, about 12% octyl salicylate, about 6.5% avobenzone, about 1.5% trimethoxybenzylidene pentanedione (SYNOXYL® HSS), about 1.5% ethylhexyl methoxycrylene (SOLASTAY® S1), about 1.5% of a bis-methoxycrylene/octyldodecyl adipic acid/methylpropanediol copolymer (SOLASTAY® P1), about 47% Lemon *Eucalyptus* oil and about 4.5% of a polymer, 3% of a film former (DERMACRYL® AQF) and about 1% fragrance. Similar SPF and repellency results are expected.

Alternatively, arachnid/insect repellency testing can be done on a sunscreen sunscreen/insect repellent composition comprising about 15% of a cellulose encapsulate comprising about 25.5% homosalate, about 12% octyl salicylate, about 6.5% avobenzone, about 1.5% trimethoxybenzylidene pentanedione (SYNOXYL® HSS), about 1.5% ethylhexyl methoxycrylene (SOLASTAY® S1), about 1.5% of a bis-methoxycrylene/octyldodecyl adipic acid/methylpropanediol copolymer (SOLASTAY® P1), about 47% Lemon *Eucalyptus* oil and about 3% of a polymer, 20% geraniol, 3% of a film former (DERMACRYL® E) and about 1% fragrance. Similar SPF and repellency results are expected.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A composition comprising one or more flexible capsules comprising one or more arachnid/insect repellents,
    wherein the one or more flexible capsules comprise a flexible shell, the flexible shell consisting of cellulose, or a salt thereof; or a cellulose derivative,
    wherein the cellulose derivative is selected from the group consisting of: hydroxypropylcellulose, hydroxypropylmethyl cellulose, ethyl cellulose and carboxymethyl cellulose, and any combination thereof; salts of hydroxypropylcellulose, hydroxypropylmethyl cellulose, and ethyl cellulose, and any combination thereof; or a derivative of hydroxypropylcellulose, hydroxypropylmethyl cellulose, and ethyl cellulose, and any combination thereof, and
    wherein the one or more flexible capsules have a mean diameter of about 200 nm to about 700 nm.

2. The composition of claim 1, wherein the one or more flexible capsules are in an amount of amount of 8% to about 20%, about 10% to about 18%, about 11% to about 17%, about 13% to about 15% or about 14% by weight of the total composition.

3. The composition of claim 1, wherein the one or more flexible capsules are in an amount of about 14% to about 26%, about 16% to about 24%, about 17% to about 23%, about 19% to about 21% or about 20% by weight of the total composition.

4. The composition of claim 1, wherein the one or more flexible capsules are in an amount of about 2% to about 40%, about 3% to about 38%, about 4% to about 36%, about 5% to about 36%, about 6% to about 34%, about 8% to about 32%, about 10% to about 30%, about 12% to about 28%, about 14% to about 26%, about 16% to about 24%, or about 18% to about 22%, by weight of the total composition.

5. The composition of claim 1, wherein the one or more flexible capsules comprises a first arachnid/insect repellent and a second arachnid/insect repellent.

6. The composition of claim 5, wherein the first arachnid/insect repellent is encapsulated in a first capsule and the second arachnid/insect repellent is encapsulated in a second capsule.

7. The composition of claim 5, wherein the first arachnid/insect repellent and the second arachnid/insect repellent are encapsulated in the same capsule.

8. The composition of claim 5, wherein the first arachnid/insect repellent is in an amount of about 1% to about 5% by weight of the total composition and the second arachnid/insect repellent is in an amount of about 95% to about 99% by weight of the total composition, or wherein the first arachnid/insect repellent is in an amount of about 6% to about 10% by weight of the total composition and the second arachnid/insect repellent is in an amount of about 90% to about 94% by weight of the total composition, or wherein the first arachnid/insect repellent is in an amount of about 11% to about 15% by weight of the total composition and the second arachnid/insect repellent is in an amount of about 85% to about 89% by weight of the total composition, or wherein the first arachnid/insect repellent is in an amount of about 16% to about 20% by weight of the total composition and the second arachnid/insect repellent is in an amount of about 80% to about 84% by weight of the total composition, or wherein the first arachnid/insect repellent is in an amount of about 21% to about 25% by weight of the total composition and the second arachnid/insect repellent is in an amount of about 75% to about 79% by weight of the total composition, or wherein the first arachnid/insect repellent is in an amount of about 26% to about 30% by weight of the total composition and the second arachnid/insect repellent is in an amount of about 70% to about 74% by weight of the total composition, or wherein the first arachnid/insect repellent is in an amount of about 31% to about 35% by weight of the total composition and the second arachnid/insect repellent is in an amount of about 65% to about 69% by weight of the total composition, or wherein the first arachnid/insect repellent is in an amount of about 36% to about 40% by weight of the total composition and the second arachnid/insect repellent is in an amount of about 60% to about 64% by weight of the total composition, or wherein the first arachnid/insect repellent is in an amount of about 41% to about 45% by weight of the total composition and the second arachnid/insect repellent is in an amount of about 55% to about 59% by weight of the total composition, or wherein the first arachnid/insect repellent is in an amount of about 46% to about 50% by weight of the total composition and the second arachnid/insect repellent is in an amount of about 50% to about 54% by weight of the total composition.

9. The composition of claim 1, further comprising one or more arachnid/insect repellents not encapsulated.

10. The composition of claim 1, wherein the one or more arachnid/insect repellents include one or more synthetic chemical compounds or one or more plant oils.

11. The composition of claim 10, wherein the one or more synthetic chemical compounds include N,N-Diethyl-m-toluamide (DEET), dimethyl phthalate, ethyl hexanediol, indalone, di-n-propylisocinchoronate, bicycloheptene, dicarboximide, dimethyl phthalate, indalone, tetrahydrofuraldehyde, or any combination thereof.

12. The composition of claim 10, wherein the one or more plant oils include a citronella oil, a lemon grass oil, a rosemary oil, an *eucalyptus* oil, or any combination thereof.

13. The composition of claim 10, wherein the one or more plant oils include citronella, limonene, eucalyptol, or any combination thereof.

14. The composition of claim 1, wherein the composition is a body wash, a shampoo, an after shower body lotion, a conditioner, a soap, a gel, a hand sanitizer, a cream, a spray, a mousse, a lotion, an ointment, a make-up product, a lip balm, a hair spray product, an arachnid/insect repellent or a medicinal product.

15. The composition of claim 1, further comprising one or more polyquaterniums, one or more surfactants, one or more film formers, one or more emollients, one or more thickening agents, one or more soap bases, one or more polymers, one or more fragrances, or any combination thereof.

16. The composition of claim 15, comprising one or more flexible capsules including one or more moisturizing agents, and one or more polyquaterniums.

17. The composition of claim 16, further comprising one or more surfactants and/or one or more soap bases, or further comprising one or more emollients and/or one or more thickening agents, or further comprising one or more film formers, or further comprising one or more emollients and/or one or more thickening agents.

18. The composition of claim 15, comprising one or more flexible capsules including one or more moisturizing agents, one or more emollients and one or more thickening agents.

19. The composition of claim 15, comprising one or more flexible capsules including one or more moisturizing agents, one or more polymers, one or more film formers and one or more fragrances.

* * * * *